United States Patent
Kapp et al.

(10) Patent No.: US 10,562,936 B2
(45) Date of Patent: Feb. 18, 2020

(54) LIGANDS FOR INTEGRIN αVβ6, SYNTHESIS AND USES THEREOF

(71) Applicant: Technische Universitat Munchen, Munich (DE)

(72) Inventors: Tobias Kapp, Lörrach (DE); Horst Kessler, Schwalbach a. T. (DE); Oleg Maltsev, Kufstein (AT)

(73) Assignee: Technische Universitat Munchen, Munich (DE)

( * ) Notice: Subject to any disclaimer, the term of this patent is extended or adjusted under 35 U.S.C. 154(b) by 0 days.

(21) Appl. No.: 15/760,119

(22) PCT Filed: Sep. 19, 2016

(86) PCT No.: PCT/EP2016/072144
§ 371 (c)(1),
(2) Date: Mar. 14, 2018

(87) PCT Pub. No.: WO2017/046416
PCT Pub. Date: Mar. 23, 2017

(65) Prior Publication Data
US 2018/0265548 A1    Sep. 20, 2018

(30) Foreign Application Priority Data
Sep. 18, 2015 (EP) .................................... 15185868

(51) Int. Cl.
*A61K 38/08* (2019.01)
*C07K 7/64* (2006.01)
*A61K 49/00* (2006.01)

(52) U.S. Cl.
CPC ................ *C07K 7/64* (2013.01); *A61K 38/08* (2013.01); *A61K 49/0056* (2013.01)

(58) Field of Classification Search
None
See application file for complete search history.

(56) References Cited

PUBLICATIONS

DiCara, Danielle et al, "Structure-function analysis of arg-gly-asp helix motifs in avb6 integrin ligands." J. Biol. Chem. (2007) 282(13) p. 9657-9665.*
Bandyopadhyay, A. and Raghavan, S.; "Defining the role if integrin avb6 in cancer." Curr. Drug Targets (2009) 19(7) p. 645-652.*
International Search Report and Written Opinion dated Nov. 11, 2016 in connection with PCT/EP2016/072144.
Kapp et al., Small Cause, Great Impact: Modification of the Guanidine Group in the RGD Motif Controls Integrin Subtype Selectivity. Angew Chem Int Ed Engl. Jan. 22, 2016;55(4):1540-3. doi: 10.1002/anie.201508713. Epub Dec. 9, 2015.
Kraft et al., Definition of an unexpected ligand recognition motif for αvβ6 integrin. J Biol Chem. Jan. 22, 1999;274(4):1979-85.
Maltsev et al., Stable Peptides Instead of Stapled Peptides: Highly Potent αvβ6-Selective Integrin Ligands. Angew Chem Int Ed Engl. Jan. 22, 2016;55(4):1535-9. doi: 10.1002/anie.201508709. Epub Dec. 9, 2015.

* cited by examiner

*Primary Examiner* — Fred H Reynolds
(74) *Attorney, Agent, or Firm* — Wolf, Greenfield & Sacks, P.C.

(57) ABSTRACT

Disclosed are compound exhibiting highly active and selective binding to αvβ6 integrin, which are represented by the following general formula (I): Cyclo-(Arg-$X^1$-Asp-$X^2$-$X^3$-$X^4$-$X^5$-$X^6$-$X^7$) (I) wherein the variables groups X to X have the following meanings $X^1$: Ser, Gly, Thr, $X^2$: Leu, Ile, Nle, Val, Phe, $X^3$: Gly, Ala, $X^4$: Leu, Ile, Nle, Val, Phe, Lys, Tyr, Trp, Arg, $X^5$: D-Pro, N-Me-D-lipophilic amino acids, $X^6$: Pro, N-Me-amino acids, N-Me-Lys, N-Me-Lys(Ac), and $X^7$: Ala, Leu, Ile, Nle, Val, Phe, Tyr, Trp or wherein the sub-sequence -$X^5$-$X^6$- represents a β-turn mimetic differing from the meanings above, or pharmaceutically acceptable salts, esters, solvates, polymorphs or modified forms thereof represented by the following general formula (II): $(X^0)_{n1}L(X^8)_{n2}$ wherein $X^0$ represents the compound of the general formula (I) as specified above (excluding one hydrogen atom to allow bonding to the linker), L represents a linker, $X^8$ represents the effector moiety and wherein n1 and n2 are each independently selected from the range of 1 to 5, wherein n1+n2 represents the number of valencies of the linker and is preferably in the range of from 2 to 6, more preferably 3-5, with the proviso that each of n1 and n2 is at least 1, as well as uses therefore in therapy and imaging.

19 Claims, 4 Drawing Sheets

Specification includes a Sequence Listing.

LIGANDS FOR INTEGRIN αVβ6, SYNTHESIS AND USES THEREOF

CROSS REFERENCE TO RELATED APPLICATIONS

The present application is the National Phase under 35 U.S.C. § 371 of PCT International Application No. PCT/EP2016/072144, filed Sep. 19, 2016, which claims priority to European Application No. 15185868.5, filed Sep. 18, 2015, which applications are incorporated herein by reference in their entirety.

1. TECHNICAL FIELD

The present invention pertains to the field of peptide-based pharmaceuticals. In particular, the present invention provides peptides and modified peptides, which bind to αvβ6 integrin with high activity and selectivity. Due to these binding properties, the inventive compounds are useful in a variety of applications including use as therapeutic agent, diagnostic agent, targeting moiety and biomolecular research tool.

2. BACKGROUND OF THE INVENTION

The family of human heterodimeric integrin receptors consists of 24 members, which differ from each other in α and β subunits. Eight integrins of this superfamily (αvβ1, αvβ3, αvβ5, αvβ6, αvβ8, α5β1, αβ1 and αIIbβ3) are able to recognize the RGD tripeptide fragment in natural and artificial ligands with varying activity and selectivity. The role of individual integrin subtypes and their cross-talks are only partially investigated due to lack of active and highly selective ligands, which are able to interact with only one single integrin subtype.

Nevertheless, already now the significance of distinct integrin subtypes in different diseases is established. That makes integrins of great interest from medical point of view. For example, integrin αvβ6 is used by the Foot-and-Mouth-Disease virus (FMDV) to enter host cells and is highly up-regulated in the course of multiple types of cancer and fibrosis.

Only few ligands are known so far that are highly active for αvβ6 integrin and at the same time possess no binding affinity toward other RGD-recognizing integrins. Unfortunately, their metabolic instability, their high molecular weight and the complexity of their structures limit their medical application.

It was shown that FMDV possesses the RXDLXXL(SEQ ID NO: 1) motif, which is responsible for selective interaction with αvβ6-integrin in an α-helical structure. Attempts to obtain selective αvβ6 ligands via incorporation of RXDLXXL (SEQ ID NO: 1) motif into cyclic peptides resulted in 10-12 mer peptides (WO 01/05810 by Merck-Serono). The best compound of this family, cyclo(RT-DLdALR-Abu-Abu) (SEQ ID NO: 2), had an αvβ6 IC50 activity of ca. 1 nM. However, its selectivity against αvβ3 integrin was reported without exact values and the information about its selectivity against other integrin subtypes is completely missing.

3. SUMMARY OF THE INVENTION

Having regard to the above situation, there is a need for novel functionalized or non-functionalized αvβ6-ligands that can be used as drugs or as tools for molecular imaging and diagnosis (PET/SPECT/UV-Vis tracers), for coating of medicinal relevant surfaces or for biophysical investigations of the function of this integrin subtype.

It was surprisingly found that low molecular weight 9-mer cyclic peptides of general formula (I) possess sub-nanomolar activity for αvβ6 integrin and show high selectivity against other RGD-binding integrins. One structural feature of the compounds of the invention is the presence of a dipeptide sequence, which may be D-Pro-L-Pro or a related sequence, which induces an optimal conformation of the amino acids responsible for binding to the αvβ6 receptor.

In contrast to the peptides disclosed in WO 01/05810, the compounds of the present invention have shorter amino acid sequence (nonapeptides). It was found that the RGDLXXL sequence, previously reported as an essential motif of linear αvβ6 selective ligands, is not required for accomplishing binding to αvβ6 with high selectivity. The compounds of the present invention are thus characterized by the general formula (I)

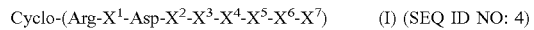

Cyclo-(Arg-$X^1$-Asp-$X^2$-$X^3$-$X^4$-$X^5$-$X^6$-$X^7$)    (I) (SEQ ID NO: 4)

The variable groups in general formula (I) have the meanings specified in appended claim 1. Preferred embodiments of the compounds of the present invention are characterized in appended dependent claims 2 to 6.

The highly active and selective binding to αvβ6 integrin allows using the compounds of the present invention as a drug for the treatment of medical indications wherein expression of αvβ6 integrin is up-regulated and/or wherein αvβ6 integrin is involved in the molecular mechanism of the indication. Such therapeutic uses of the compounds of the present invention are specified in appended claims 8 to 10.

The substitution of L-proline by N-methyl-L-lysine is possible and allows to functionalize ligands for instance with fluorescent dyes or other labeling groups without any loss of activity or selectivity. The fluorescent labeled ligands can be applied for diagnostic applications. Such applications are specified in appended claim 11.

The present invention also provides pharmaceutical compositions as specified in appended claims 7 and 12. Finally, it provides methods for the synthesis of the compounds of the present invention. Such methods are specified in appended claims 13 and 14.

The suitability for diagnostic applications has been demonstrated successfully for the cancer cell-line HN possessing high levels of αvβ6-integrin expression. Under the same conditions, OVMZ6 cancer cells with low αvβ6- and high αvβ3-integrin expression were undetectable. A complete profile of ligand activity toward six RGD-binding integrins (αvβ3, αvβ5, αvβ6, αvβ8, αIIbβ3, α5β1) was established. It shows that the compounds of the present invention possess αvβ6 selectivity (at least two orders of magnitude) both in solid-phase binding assays and cellular experiments.

4. DESCRIPTION OF FIGURES

Figure 2A:
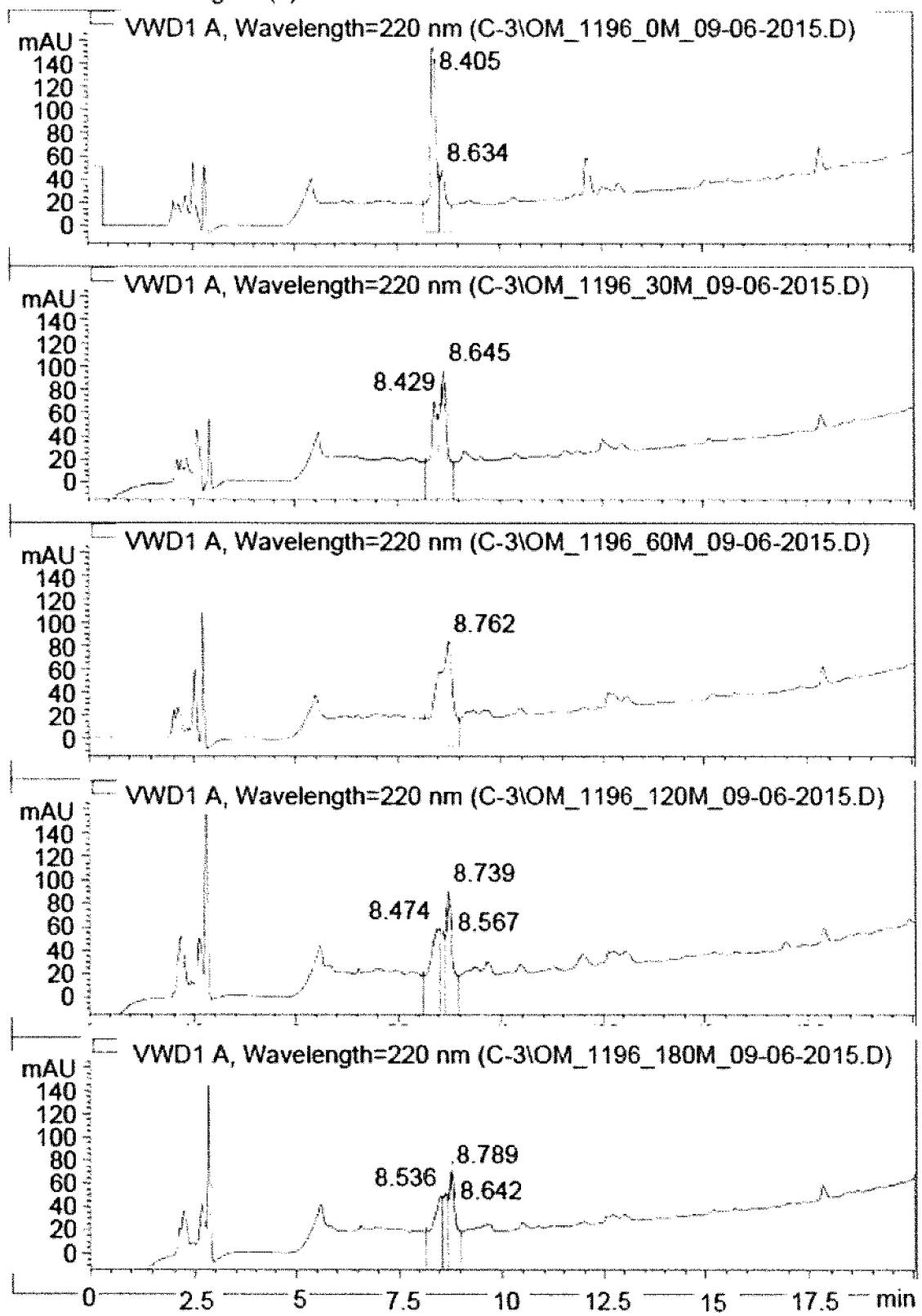
FIG. 2a shows HPLC chromatograms of RTDLDSLRT (SEQ ID NO: 3) peptide (comparative compound) after different intervals of incubation with human plasma. HPLC chromatograms are shown for time points 0 min, 30 min, 60 min, 120 min and 180 min (from top to bottom).
Figure 2B:
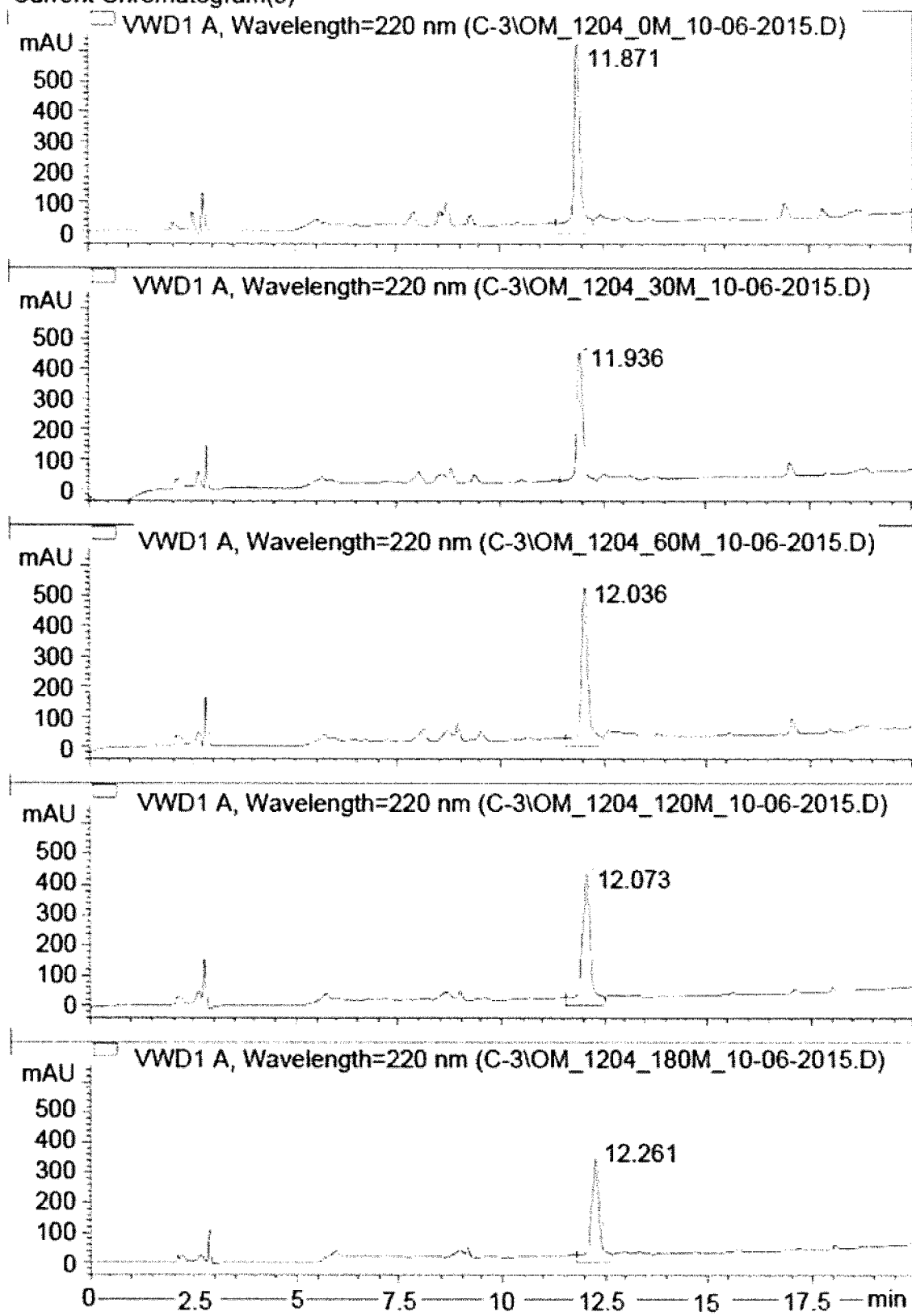

FIG. 2b shows HPLC chromatograms of exemplified compound 18 after different intervals of incubation with human plasma. HPLC chromatograms are shown for time points 0 min, 30 min, 60 min, 120 min and 180 min (from top to bottom).

Figure 2C:
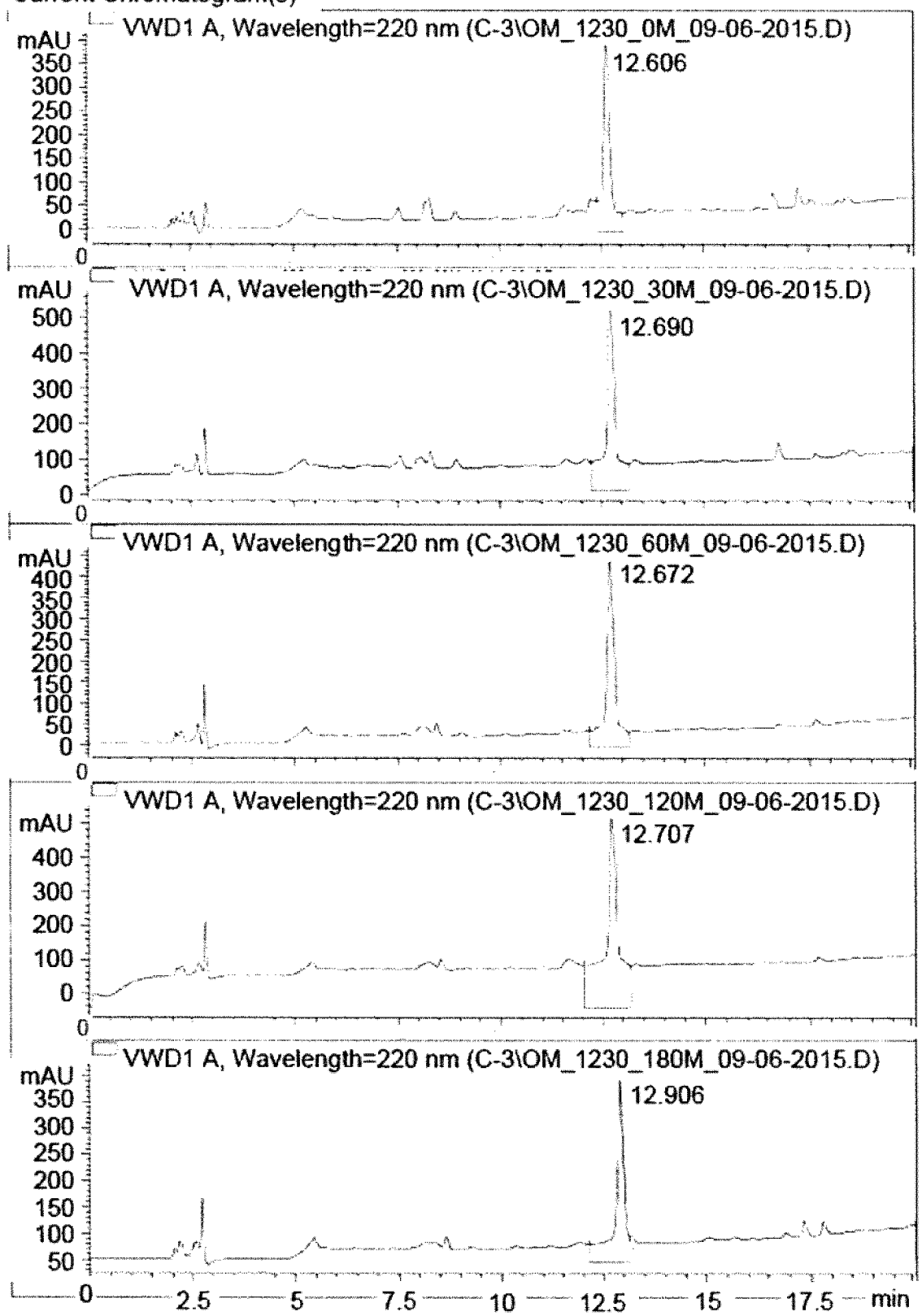

FIG. 2c shows HPLC chromatograms of exemplified compound 23 after different intervals of incubation with human plasma. HPLC chromatograms are shown for time points 0 min, 30 min, 60 min, 120 min and 180 min (from top to bottom).

5. DETAILED DESCRIPTION

5.1. Definitions

Unless specified otherwise, standard amino acid nomenclature is used. Unless specified otherwise, amino acids are L-stereoisomers. Unless specified otherwise, amino acid moieties are linked to each other via peptide bonds.

Sar refers to Sarcosine.

Nle refers to Norleucine.

Me refers to a methyl group.

N-Me-amino acid refers to a group, wherein the α-amino group carries a methyl group.

Lys(Ac) refers to a lysine residue, wherein the ω-amino group carries an acetyl group.

Unless the context dictates otherwise, references to the "compound of the invention" are to be understood as references not only to the compound of the present invention according to general formula (I) described hereinbelow, but also as references to the pharmaceutically acceptable salts, esters, solvates, polymorphs or modified forms thereof as represented by the general formula (II) described hereinbelow.

The term "amino acid" generally refers to an organic compound comprising both a carboxylic acid group and an amine group. Unless specified otherwise, the term "amino acid" is meant to cover both natural and synthetic amino acids, but wherein the use of natural amino acids is preferred. The term "natural amino acid" and equivalent expressions refer to amino acids commonly found in naturally occurring proteins. Examples of natural amino acids include, without limitation, alanine (Ala), cystein (Cys), aspartic acid (Asp), glutamic acid (Glu), phenylalanine (Phe), glycine (Gly), histidine (His), isoleucine (Ile), lysine (Lys), leucine (Leu), methionine (Met), asparagine (Asp), proline (Pro), glutamine (Gln), arginine (Arg), serine (Ser), threonine (Thr), valine (Val), tryptophan (Trp), and tyrosine (Tyr).

It will be understood that "substitution" or "substituted with" includes the implicit proviso that such substitution is in accordance with the permitted valence of the substituted atom and the substituent, and that the substitution results in a stable compound, e.g., which does not spontaneously undergo transformation such as by rearrangement, cyclization, elimination, etc.

As used herein, the term "substituted" is meant to include all permissible substituents of organic compounds. In a broad aspect, the permissible substituents include acyclic and cyclic, branched and unbranched, carbocyclic and heterocyclic, aromatic and nonaromatic substituents of organic compounds. The permissible substituents can be one or more. Unless specified otherwise, the term "substituted", when in association with any of the below groups refers to a group substituted at one or more position with substituents such as alkyl, alkenyl, alkynyl, alkoxy, acyl, amino (including simple amino, mono and dialkylamino, mono and diarylamino, and alkylarylamino), acylamino (including carbamoyl, and ureido), alkylcarbonyloxy, arylcarbonyloxy, alkoxycarbonyloxy, alkoxycarbonyl, carboxy, carboxylate, aminocarbonyl, mono and dialkylaminocarbonyl, cyano, azido, halogen, hydroxyl, nitro, trifluoromethyl, thio, alkylthio, arylthio, alkylthiocarbonyl, thiocarboxylate, cycloalkyl, heterocycloalkyl, aryl, heteroaryl, aryloxy, aryloxycarbonyloxy, benzyloxy, benzyl, sulfinyl, alkylsulfinyl, sulfonyl, sulfate, sulfonate, sulfonamide, phosphate, phosphonato, phosphinato, oxo, guanidine, imino, formyl and the like. Any of the above substituents can be further substituted if permissible, e.g. if the group contains an alkyl group, an aryl group, or other.

Unless specified otherwise, all abbreviations are intended to have their commonly used meaning as represented, for instance, by the IUPAC-IUP Commission on Biochemical Nomenclature in Biochemistry 11, 1972, 942-944.

Unless specified otherwise, compounds of the present invention are "pharmaceutically acceptable" which means that the respective compounds are suitable for use with humans and/or animals without causing adverse effects (such as irritation or toxicity), commensurate with a reasonable benefit/risk ratio.

The term "or" is generally employed in its sense including "and/or" unless the content clearly dictates otherwise.

The chemical structures herein are drawn according to the conventional standards known in the art. Thus, where an atom, such as a carbon atom, as drawn appears to have an unsatisfied valency, then that valency is assumed to be satisfied by a hydrogen atom even though that hydrogen atom is not necessarily explicitly drawn. Hydrogen atoms should be inferred to be part of the compound.

The symbol "-" in general represents a bond between two atoms in the chain. In addition, the symbol "-" also represents the point of attachment of the substituent to a compound. Thus for example aryl($C_1$-$C_6$)alkyl- indicates an arylalkyl group, such as benzyl, attached to the compound through the alkyl moiety.

Where multiple substituents are indicated as being attached to a structure, it is to be understood that the substituent can be the same or different.

As used herein, the term "alkyl" refers to saturated hydrocarbons having from one to sixteen carbon atoms, more preferably from one to six carbon atoms, including linear or branched alkyl groups. Examples of alkyl groups include, without limitation, methyl, ethyl, propyl, butyl, pentyl, hexyl, heptyl, octyl, nonyl, decyl, isopropyl, tert-butyl, sec-butyl, isobutyl, and the like. The term "$C_1$-$C_n$alkyl" refers to an alkyl group having from 1 to the indicated "n" number of carbon atoms. The term "alkylene" group refers to a group derived from an alkyl group as defined above, but having two valencies instead of the single valency of the alkyl group. Preferably, the two free valencies are at opposing termini of the alkylene group.

As used herein, the term "alkenyl" refers to unsaturated hydrocarbons having from two to sixteen carbon atoms, more preferably from two to six carbon atoms, including linear or branched alkenyl groups, and comprising between one and six carbon-carbon double bonds. Examples of alkenyl groups include, without limitation, vinyl, allyl, 1-propen-2-yl, 1-buten-3-yl, 1-buten-4-yl, 2-buten-4-yl, 1-penten-5-yl, 1,3-pentadien-5-yl, and the like. The term alkenyl includes both unsubstituted alkenyl groups and substituted alkenyl groups. The term "$C_2$-$C_n$alkenyl" refers to an alkenyl group having from 2 to the indicated "n" number of carbon atoms. The term "alkenylene" group refers to a group derived from an alkenyl group as defined above, but having two valencies instead of the single valency of the alkenyl group. Preferably, the two free valencies are at opposing termini of the alkenylene group.

As used herein, the term "alkynyl" refers to unsaturated hydrocarbons having from two to twelve carbon atoms, more preferably from two to six carbon atoms, including linear or branched alkynyl groups, and comprising between one to six carbon-carbon triple bond. Examples of alkynyl groups include, without limitation, ethynyl, 1-propyn-3-yl, 1-butyn-4-yl, 2-butyn-4-yl, 1-pentyn-5-yl, 1,3-pentadiyn-5-yl, and the like. The term alkynyl includes both unsubstituted alkynyl groups and substituted alkynyl groups. The term "$C_2$-$C_n$alkynyl" refers to an alkynyl group having from 2 to the indicated "n" number of carbon atoms. The term "alkynylene" group refers to a group derived from an alkynyl group as defined above, but having two valencies instead of the single valency of the alkynyl group. Preferably, the two free valencies are at opposing termini of the alkynylene group.

The terms "cycloalkyl", "carbocyclic" and equivalent expressions refer to a group comprising a saturated or partially unsaturated (non aromatic) carbocyclic ring in a monocyclic or polycyclic ring system, including spiro (sharing one atom) or fused (sharing at least one bond) carbocyclic ring systems, having from three to fifteen ring members. Examples of cycloalkyl groups include, without limitation, cyclopropyl, cyclobutyl, cyclopentyl, cyclopenten-1-yl, cyclopenten-2-yl, cyclopenten-3-yl, cyclohexyl, cyclohexen-1-yl, cyclohexen-2-yl, cyclohexen-3-yl, cycloheptyl, bicyclo[4,3,0]nonanyl, norbornyl, and the like. The term cycloalkyl includes both unsubstituted cycloalkyl groups and substituted cycloalkyl groups. The term "$C_3$-$C_n$cycloalkyl" refers to a cycloalkyl group having from 3 to the indicated "n" number of carbon atoms in the ring structure.

The term "heterocycloalkyl" and equivalent expressions refer to a group comprising a saturated or partially unsaturated (non aromatic) carbocyclic ring in a monocyclic or polycyclic ring system, including spiro (sharing one atom) or fused (sharing at least one bond) carbocyclic ring systems, having from three to fifteen ring members, where one or more (up to six) ring members are substituted or unsubstituted heteroatoms (e.g. N, O, S, P) or groups containing such heteroatoms (e.g. NH, $NR_x$ ($R_x$ is alkyl, acyl, aryl, heteroaryl or cycloalkyl), $PO_2$, SO, $SO_2$, and the like). Heterocycloalkyl groups may be C-attached or heteroatom-attached (e.g. via a nitrogen atom) where such is possible. Examples of heterocycloalkyl groups include, without limitation, pyrrolidino, tetrahydrofuranyl, tetrahydrodithienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3,1,0]hexanyl, 3-azabicyclo[4,1,0]heptanyl, quinolizinyl, and sugars, and the like. The term heterocycloalkyl includes both unsubstituted heterocycloalkyl groups and substituted heterocycloalkyl groups. The term "$C_3$-$C_n$heterocycloalkyl" refers to a heterocycloalkyl group having from 3 to the indicated "n" number of atoms (carbon or heteroatom or group) in the ring structure, including at least one hetero group or atom as defined above.

The terms "aryl" and "aryl ring" refer to aromatic groups having 4n+2 n(pi) electrons, wherein n is an integer from 1 to 3, in a conjugated monocyclic or polycyclic system (fused or not) and having six to fourteen ring atoms. A polycyclic ring system includes at least one aromatic ring. Aryl may be directly attached, or connected via a $C_1$-$C_3$alkyl group (also referred to as arylalkyl or aralkyl). Examples of aryl groups include, without limitation, phenyl, benzyl, phenetyl, 1-phenylethyl, tolyl, naphthyl, biphenyl, terphenyl, indenyl, benzocyclooctenyl, benzocycloheptenyl, azulenyl, acenaphthylenyl, fluorenyl, phenanthernyl, anthracenyl, and the like. The term aryl includes both unsubstituted aryl groups and substituted aryl groups. The term "$C_6$-$C_n$aryl" refers to an aryl group having from 6 to the indicated "n" number of carbons in the ring structure.

The terms "heteroaryl" and "heteroaryl ring" refer to aromatic groups having 4n+2 n(pi) electrons, wherein n is an integer from 1 to 3, in a conjugated monocyclic or polycyclic system (fused or not) and having five to fourteen ring members, including one to six substituted or unsubstituted heteroatoms (e.g. N, O, S) or groups containing such heteroatoms (e.g. NH, $NR_x$ ($R_x$ is alkyl, acyl, aryl, heteroaryl or cycloalkyl), SO, and the like). A polycyclic ring system includes at least one heteroaromatic ring. Heteroaryls may be directly attached, or connected via a $C_1$-$C_3$alkyl group (also referred to as heteroarylalkyl or heteroaralkyl). Heteroaryl groups may be C-attached or heteroatom-attached (e.g. via a nitrogen atom), where such is possible. Examples of heteroaryl groups include, without limitation, pyridyl, imidazolyl, pyrimidinyl, pyrazolyl, triazolyl, tetrazolyl, furyl, thienyl; isooxazolyl, thiazolyl, oxazolyl, isothiazolyl, pyrrolyl, quinolinyl, isoquinolinyl, indolyl, 3H-indolyl, indolinyl, isoindolyl, chromenyl, isochromenyl, benzimidazolyl, benzofuranyl, cinnolinyl, indazolyl, indolizinyl, phthalazinyl, pyridazinyl, pyrazinyl, triazinyl, isoindolyl, pteridinyl, purinyl, oxadiazolyl, thiadiazolyl, furazanyl, benzofurazanyl, benzothiophenyl, benzothienyl, benzothiazolyl, benzoxazolyl, quinazolinyl, quinolizinyl, quinolonyl, isoquinolonyl, quinoxalinyl, naphthyridinyl, furopyridinyl, carbazolyl, phenanthridinyl, acridinyl, perimidinyl, phenanthrolinyl, phenazinyl, phenothiazinyl, phenoxazinyl, dibenzofurnayl, and the like. The term heteroaryl includes both unsubstituted heteroaryl groups and substituted heteroaryl groups. The term "$C_5$-$C_n$heteroaryl refers to an heteroaryl group having from 5 to the indicated "n" number of atoms (carbon or heteroatom or group) in the ring structure, including at least one hetero group or atom as defined above.

The terms "heterocycle" or "heterocyclic" or "heterocyclyl" include heterocycloalkyl and heteroaryl groups. Examples of heterocycles include, without limitation, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4αH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl, and the like. The term heterocycle includes both unsubstituted heterocyclic groups and substituted heterocyclic groups.

The term "amine" or "amino," as used herein, refers to an unsubstituted or substituted moiety of the formula —$NR^aR^b$, in which $R^a$ and $R^b$ are each independently hydrogen, alkyl, aryl, or heterocyclyl, or $R^a$ and $R^b$, taken together with the nitrogen atom to which they are attached, form a heterocyclic ring. The term "amide" or "aminocarbonyl" includes compounds or moieties which contain a nitrogen atom which is bound to the carbon of a carbonyl or a thiocarbonyl group. The term acylamino refers to an amino group directly attached to an acyl group as defined herein.

The term "nitro" means —$NO_2$; the term "halogen" refers to bromine, chlorine, fluorine or iodine substituents; the term "thiol" means SH; and the term "hydroxyl" or "hydroxy" means —OH. The term "alkylthio" refers to an alkyl group, having a sulfhydryl group attached thereto. Suitable alkylthio groups include groups having 1 to about 12 carbon atoms, preferably from 1 to about 6 carbon atoms. The term "alkylcarboxyl" as used herein means an alkyl group having a carboxyl group attached thereto.

The term "alkoxy" as used herein means an alkyl group having an oxygen atom attached thereto. Representative alkoxy groups include groups having 1 to about 6 carbon atoms, e.g., methoxy, ethoxy, propoxy, tert-butoxy and the like. Examples of alkoxy groups include methoxy, ethoxy, isopropyloxy, propoxy, butoxy, pentoxy, fluoromethoxy, difluoromethoxy, trifluoromethoxy, chloromethoxy, dichloromethoxy, trichloromethoxy groups and the like.

The term alkoxy includes both unsubstituted or substituted alkoxy groups, etc., as well as halogenated alkyloxy groups. The term "carbonyl" or "carboxy" includes compounds and moieties which contain a carbon connected with a double bond to an oxygen atom. Examples of moieties which contain a carbonyl include aldehydes, ketones, carboxylic acids, amides, esters, anhydrides, etc. The term "acyl" refers to a carbonyl group that is attached through its carbon atom to a hydrogen (i.e., formyl), an aliphatic group ($C_1$-$C_n$alkyl, $C_1$-$C_n$alkenyl, $C_1$-$C_n$alkynyl, wherein n is an integer from 2 to 10; e.g. acetyl, a cycloalkyl group (e.g. $C_3$-$C_8$cycloalkyl), a heterocyclic group (e.g. $C_3$-$C_8$heterocycloalkyl and $C_5$-$C_6$heteroaryl), an aromatic group (e.g. $C_6$aryl, e.g., benzoyl), and the like. Acyl groups may be unsubstituted or substituted acyl groups (e.g. salicyloyl).

The term "solvate" refers to a physical association of a compound of this invention with one or more solvent molecules, whether organic or inorganic. This physical association includes hydrogen bonding. In certain instances, the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, hemiethanolates, and the like, preferably hydrates.

A "pharmaceutically acceptable salt" of a compound means a salt of a compound that is pharmaceutically acceptable. Desirable are salts of a compound that retain or improve the biological effectiveness and properties of the free acids and bases of the parent compound as defined herein or that takes advantage of an intrinsically basic, acidic or charged functionality on the molecule and that is not biologically or otherwise undesirable. Example of pharmaceutically acceptable salts are also described, for example, in Berge et al., "Pharmaceutical Salts", *J. Pharm. Sci.* 66, 1-19 (1977). Such salts include: (1) acid addition salts, formed on a basic or positively charged functionality, by the addition of inorganic acids such as hydrochloric acid, hydrobromic acid, hydroiodic acid, sulfuric acid, sulfamic acid, nitric acid, phosphoric acid, carbonate forming agents, and the like; or formed with organic acids such as acetic acid, propionic acid, lactic acid, oxalic, glycolic acid, pivalic acid, t-butylacetic acid, β-hydroxybutyric acid, valeric acid, hexanoic acid, cyclopentanepropionic acid, pyruvic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, cyclohexylaminosulfonic acid, benzenesulfonic acid, sulfanilic acid, 4-chlorobenzenesulfonic acid, 2-napthalenesulfonic acid, 4-toluenesulfonic acid, camphorsulfonic acid, 3-phenyl propionic acid, lauryl sulphonic acid, lauryl sulfuric acid, oleic acid, palmitic acid, stearic acid, lauric acid, embonic (pamoic) acid, palmoic acid, pantothenic acid, lactobionic acid, alginic acid, galactaric acid, galacturonic acid, gluconic acid, glucoheptonic acid, glutamic acid, naphthoic acid, hydroxynapthoic acid, salicylic acid, ascorbic acid, stearic acid, muconic acid, and the like; (2) base addition salts, formed when an acidic proton present in the parent compound either is replaced by a metal ion, including, an alkali metal ion (e.g. lithium, sodium, potassium), an alkaline earth ion (e.g. magnesium, calcium, barium), or other metal ions such as aluminum, zinc, iron and the like; or coordinates with an organic base such as ammonia, ethylamine, diethylamine, ethylenediamine, N,N'-dibenzylethylenediamine, ethanolamine, diethanolamine, triethanolamine, tromethamine, N-methylglucamine, piperazine, chloroprocain, procain, choline, lysine and the like.

Pharmaceutically acceptable salts may be synthesized from the parent compound that contains a basic or acidic moiety, by conventional chemical methods. Generally, such salts are prepared by reacting the free acid or base forms of these compounds with a stoichiometric amount of the appropriate base or acid in water or in an organic solvent, or in a mixture of the two. Salts may be prepared in situ, during the final isolation or purification of the agent or by separately reacting a purified compound of the invention in its free acid or base form with the desired corresponding base or acid, and isolating the salt thus formed. The term "pharmaceutically acceptable salts" also include zwitterionic compounds containing a cationic group covalently bonded to an anionic group, as they are "internal salts".

All acid, salt, base, and other ionic and non-ionic forms of the compounds described are included as compounds of the invention. For example, if a compound is shown as an acid herein, the salt forms of the compound are also included. Likewise, if a compound is shown as a salt, the acid and/or basic forms are also included.

"Pharmaceutically acceptable vehicle" or "pharmaceutically acceptable carrier" refers to a diluent, adjuvant, excipient, or carrier with which a compound is administered.

"Pharmaceutical composition" refers to at least one compound and at least one pharmaceutically acceptable vehicle or carrier, with which the compound is administered to a patient.

5.2. Compounds of the Invention

The compounds of the present invention are characterized by the following general formula (I):

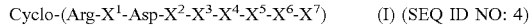
Cyclo-(Arg-X$^1$-Asp-X$^2$-X$^3$-X$^4$-X$^5$-X$^6$-X$^7$)    (I) (SEQ ID NO: 4)

wherein the variables groups X$^1$ to X$^7$ have the following meanings
X$^1$: Ser, Gly, Thr
X$^2$: Leu, Ile, Nle, Val, Phe
X$^3$: Gly, Ala
X$^4$: Leu, Ile, Nle, Val, Phe, Lys, Tyr, Trp, Arg
X$^5$: D-Pro, N-Me-D-lipophilic amino acids
X$^6$: Pro, N-Me-amino acids, N-Me-Lys, N-Me-Lys(Ac)
X$^7$: Ala, Leu, Ile, Nle, Val, Phe, Tyr, Trp The sub-sequence -X$^5$-X$^6$- may also represent a β-turn mimetic differing from the meanings above, such as disclosed, for instance, in U. Nagai, K. Sato, Tetr. Lett. 1985, 26, 647; Feigel et. al. JACS 1986, 108, 181; H. Diaz, J. W. Kelly, Tetr. Lett. 1991, 32, 5725; Feigel et. al. Helv. Chem. Acta 1994, 77, 70; J. A. Robinson et. al. Angew. Chem. 2004, 116, 2161; and Kessler et. al. J. Am. Chem. Soc. 1996, 118, 7881.

The compounds of the present invention may also be in the form of a pharmaceutically acceptable salts, esters, solvates, polymorphs or modified forms thereof. Pharmaceutically acceptable salt may include, for instance, salts formed by reaction of acidic residues with inorganic or organic alkaline substances as well as salts formed by reaction of basic residues with inorganic or organic acids. Preferred salts are sulfates, nitrates, chlorides, bromides, phosphates, sulfonates, tartrates, formates, maleates, malates, citrates, benzoates, ascorbates, etc. Pharmaceutically acceptable esters may be esters formed by reaction of side chain hydroxyl groups in Tyr residues with suitable carboxylic acids typically having from 2 to 20 carbon atoms. Solvates may be formed by crystallizing the compounds of the invention with any pharmaceutically acceptable solvent including, for instance, water and ethanol. As regards polymorphs, there is no particular limitation. The amorphous form can also be used. Modified forms of the compound of the present invention include the specific modified compounds described below by reference to general formula (II). Further modified forms of the compound of the present invention may include compounds of the present invention that have been modified by covalently attaching pharmaceutically acceptable moieties such as C$_{1-20}$ alkyl groups via hydrolyzable groups to generate a prodrug form of the compounds of the present invention. Such suitable modifications are described, for instance, on page 11 in lines 10 to 25 of WO 01/05810.

Preferred compounds of the present invention are characterized by the above general formula (I), wherein the variable groups X$^1$ to X$^7$ have the following more specific meanings.

Embodiment 1 (SEQ ID NO: 5)

X$^1$: Gly
X$^2$: Leu, Ile, Nle, Val, Phe
X$^3$: Gly, Ala
X$^4$: Leu, Ile, Nle, Val, Phe, Lys, Tyr, Trp, Arg
X$^5$: D-Pro, N-Me-D-lipophilic Amino acids
X$^6$: Pro, N-Me-Amino acids, N-Me-Lys, N-Me-Lys(Ac)
X$^7$: Ala, Leu, Ile, Nle, Val, Phe, Tyr, Trp Embodiment 2 (SEQ ID NO: 6)

X$^1$: Ser, Gly, Thr
X$^2$: Leu, Nle
X$^3$: Gly, Ala
X$^4$: Leu, Ile, Nle, Val, Phe, Lys, Tyr, Trp, Arg
X$^5$: D-Pro, N-Me-D-lipophilic Amino acids
X$^6$: Pro, N-Me-Amino acids, N-Me-Lys, N-Me-Lys(Ac)
X$^7$: Ala, Leu, Ile, Nle, Val, Phe, Tyr, Trp Embodiment 3 (SEQ ID NO: 7)

X$^1$: Ser, Gly, Thr
X$^2$: Leu
X$^3$: Gly, Ala
X$^4$: Leu, Ile, Nle, Val, Phe, Lys, Tyr, Trp, Arg
X$^5$: D-Pro, N-Me-D-lipophilic Amino acids
X$^6$: Pro, N-Me-Amino acids, N-Me-Lys, N-Me-Lys(Ac)
X$^7$: Ala, Leu, Ile, Nle, Val, Phe, Tyr, Trp Embodiment 4 (SEQ ID NO: 8)

X$^1$: Ser, Gly, Thr
X$^2$: Leu, Ile, Nle, Val, Phe
X$^3$: Gly
X$^4$: Leu, Ile, Nle, Val, Phe, Lys, Tyr, Trp, Arg
X$^5$: D-Pro, N-Me-D-lipophilic Amino acids
X$^6$: Pro, N-Me-Amino acids, N-Me-Lys, N-Me-Lys(Ac)
X$^7$: Ala, Leu, Ile, Nle, Val, Phe, Tyr, Trp Embodiment 5 (SEQ ID NO: 9)

X$^1$: Ser, Gly, Thr
X$^2$: Leu, Ile, Nle, Val, Phe
X$^3$: Gly, Ala
X$^4$: Leu, Phe, Lys, Tyr, Trp, Arg
X$^5$: D-Pro, N-Me-D-lipophilic Amino acids
X$^6$: Pro, N-Me-Amino acids, N-Me-Lys, N-Me-Lys(Ac)
X$^7$: Ala, Leu, Ile, Nle, Val, Phe, Tyr, Trp Embodiment 6 (SEQ ID NO: 10)

X$^1$: Ser, Gly, Thr
X$^2$: Leu, Ile, Nle, Val, Phe
X$^3$: Gly, Ala
X$^4$: Leu, Ile, Nle, Val, Phe, Lys, Tyr, Trp, Arg
X$^5$: D-Pro
X$^6$: Pro, N-Me-Amino acids, N-Me-Lys, N-Me-Lys(Ac)
X$^7$: Ala, Leu, Ile, Nle, Val, Phe, Tyr, Trp Embodiment 7 (SEQ ID NO: 11)

X$^1$: Ser, Gly, Thr
X$^2$: Leu, Ile, Nle, Val, Phe
X$^3$: Gly, Ala
X$^4$: Leu, Ile, Nle, Val, Phe, Lys, Tyr, Trp, Arg
X$^5$: D-Pro, N-Me-D-lipophilic Amino acids
X$^6$: Pro, Sar, N-Me-Lys, N-Me-Lys(Ac)
X$^7$: Ala, Leu, Ile, Nle, Val, Phe, Tyr, Trp Embodiment 8 (SEQ ID NO: 12)

X$^1$: Ser, Gly, Thr
X$^2$: Leu, Ile, Nle, Val, Phe

X³: Gly, Ala
X⁴: Leu, Ile, Nle, Val, Phe, Lys, Tyr, Trp, Arg
X⁵: D-Pro, N-Me-D-lipophilic Amino acids
X⁶: Pro, N-Me-Amino acids, N-Me-Lys, N-Me-Lys(Ac)
X⁷: Ala, Phe, Tyr, Trp Embodiment 1.1 (SEQ ID NO: 13)

X¹: Gly
X²: Leu
X³: Gly, Ala
X⁴: Leu, Ile, Nle, Val, Phe, Lys, Tyr, Trp, Arg
X⁵: D-Pro, N-Me-D-lipophilic Amino acids
X⁶: Pro, N-Me-Amino acids, N-Me-Lys, N-Me-Lys(Ac)
X⁷: Ala, Leu, Ile, Nle, Val, Phe, Tyr, Trp Embodiment 1.2 (SEQ ID NO: 14)

X¹: Gly
X²: Leu
X³: Ala
X⁴: Leu, Ile, Nle, Val, Phe, Lys, Tyr, Trp, Arg
X⁵: D-Pro, N-Me-D-lipophilic Amino acids
X⁶: Pro, N-Me-Amino acids, N-Me-Lys, N-Me-Lys(Ac)
X⁷: Ala, Leu, Ile, Nle, Val, Phe, Tyr, Trp Embodiment 1.3 (SEQ ID NO: 15)

X¹: Gly
X²: Leu
X³: Ala
X⁴: Leu, Phe, Lys, Tyr, Trp, Arg
X⁵: D-Pro, N-Me-D-lipophilic Amino acids
X⁶: Pro, N-Me-Amino acids, N-Me-Lys, N-Me-Lys(Ac)
X⁷: Ala, Leu, Ile, Nle, Val, Phe, Tyr, Trp Embodiment 1.4 (SEQ ID NO: 16)

X¹: Gly
X²: Leu
X³: Ala
X⁴: Leu, Phe, Lys, Tyr, Trp, Arg
X⁵: D-Pro
X⁶: Pro, N-Me-Amino acids, N-Me-Lys, N-Me-Lys(Ac)
X⁷: Ala, Leu, Ile, Nle, Val, Phe, Tyr, Trp Embodiment 1.5 (SEQ ID NO: 17)

X¹: Gly
X²: Leu
X³: Ala
X⁴: Leu, Phe, Lys, Tyr, Trp, Arg
X⁵: D-Pro
X⁶: Pro, Sar, N-Me-Lys, N-Me-Lys(Ac)
X⁷: Ala, Leu, Ile, Nle, Val, Phe, Tyr, Trp

Embodiment 1.6 (SEQ ID NO: 18)

X¹: Gly
X²: Leu
X³: Ala
X⁴: Leu, Phe, Lys, Tyr, Trp, Arg
X⁵: D-Pro
X⁶: Pro, Sar, N-Me-Lys, N-Me-Lys(Ac)
X⁷: Ala, Phe, Tyr, Trp

Embodiment 1.7 (SEQ ID NO: 19)

X¹: Gly
X²: Leu

X³: Ala
X⁴: Leu, Ile, Nle, Val, Phe, Lys, Tyr, Trp, Arg
X⁵: D-Pro
X⁶: Pro, N-Me-Amino acids, N-Me-Lys, N-Me-Lys(Ac)
X⁷: Ala, Leu, Ile, Nle, Val, Phe, Tyr, Trp Embodiment 1.8 (SEQ ID NO: 20)

X¹: Gly
X²: Leu
X³: Ala
X⁴: Leu, Ile, Nle, Val, Phe, Lys, Tyr, Trp, Arg
X⁵: D-Pro
X⁶: Pro, Sar, N-Me-Lys, N-Me-Lys(Ac)
X⁷: Ala, Leu, Ile, Nle, Val, Phe, Tyr, Trp

Embodiment 1.9 (SEQ ID NO: 21)

X¹: Gly
X²: Leu, Nle
X³: Gly, Ala
X⁴: Leu, Ile, Nle, Val, Phe, Lys, Tyr, Trp, Arg
X⁵: D-Pro, N-Me-D-lipophilic Amino acids
X⁶: Pro, N-Me-Amino acids, N-Me-Lys, N-Me-Lys(Ac)
X⁷: Ala, Leu, Ile, Nle, Val, Phe, Tyr, Trp Embodiment 1.10 (SEQ ID NO: 22)

X¹: Gly
X²: Leu, Nle
X³: Ala
X⁴: Leu, Ile, Nle, Val, Phe, Lys, Tyr, Trp, Arg
X⁵: D-Pro, N-Me-D-lipophilic Amino acids
X⁶: Pro, N-Me-Amino acids, N-Me-Lys, N-Me-Lys(Ac)
X⁷: Ala, Leu, Ile, Nle, Val, Phe, Tyr, Trp Embodiment 1.11 (SEQ ID NO: 23)

X¹: Gly
X²: Leu, Nle
X³: Ala
X⁴: Leu, Phe, Lys, Tyr, Trp, Arg
X⁵: D-Pro, N-Me-D-lipophilic Amino acids
X⁶: Pro, N-Me-Amino acids, N-Me-Lys, N-Me-Lys(Ac)
X⁷: Ala, Leu, Ile, Nle, Val, Phe, Tyr, Trp Embodiment 1.12 (SEQ ID NO: 24)

X¹: Gly
X²: Leu, Nle
X³: Ala
X⁴: Leu, Phe, Lys, Tyr, Trp, Arg
X⁵: D-Pro
X⁶: Pro, N-Me-Amino acids, N-Me-Lys, N-Me-Lys(Ac)
X⁷: Ala, Leu, Ile, Nle, Val, Phe, Tyr, Trp Embodiment 1.13 (SEQ ID NO: 25)

X¹: Gly
X²: Leu, Nle
X³: Ala
X⁴: Leu, Phe, Lys, Tyr, Trp, Arg
X⁵: D-Pro
X⁶: Pro, Sar, N-Me-Lys, N-Me-Lys(Ac)
X⁷: Ala, Leu, Ile, Nle, Val, Phe, Tyr, Trp

Embodiment 1.14 (SEQ ID NO: 26)

X¹: Gly
X²: Leu, Nle $X^3$: Ala
$X^4$: Leu, Phe, Lys, Tyr, Trp, Arg
$X^5$: D-Pro
$X^6$: Pro, Sar, N-Me-Lys, N-Me-Lys(Ac)
$X^7$: Ala, Phe, Tyr, Trp

Embodiment 1.15 (SEQ ID NO: 27)

$X^1$: Gly
$X^2$: Leu, Nle
$X^3$: Gly, Ala
$X^4$: Leu, Ile, Nle, Val, Phe, Lys, Tyr, Trp, Arg
$X^5$: D-Pro
$X^6$: Pro, N-Me-Amino acids, N-Me-Lys, N-Me-Lys(Ac)
$X^7$: Ala, Leu, Ile, Nle, Val, Phe, Tyr, Trp Embodiment 1.16 (SEQ ID NO: 28)

$X^1$: Gly
$X^2$: Leu, Nle
$X^3$: Gly, Ala
$X^4$: Leu, Ile, Nle, Val, Phe, Lys, Tyr, Trp, Arg
$X^5$: D-Pro
$X^6$: Pro, Sar, N-Me-Lys, N-Me-Lys(Ac)
$X^7$: Ala, Leu, Ile, Nle, Val, Phe, Tyr, Trp

Embodiment 1.17 (SEQ ID NO: 29)

$X^1$: Gly
$X^2$: Leu, Nle
$X^3$: Ala
$X^4$: Leu, Ile, Nle, Val, Phe, Lys, Tyr, Trp, Arg
$X^5$: D-Pro
$X^6$: Pro, Sar, N-Me-Lys, N-Me-Lys(Ac)
$X^7$: Ala, Leu, Ile, Nle, Val, Phe, Tyr, Trp

Embodiment 1.18 (SEQ ID NO: 30)

$X^1$: Gly
$X^2$: Leu, Nle
$X^3$: Ala
$X^4$: Leu, Ile, Nle, Val, Phe, Lys, Tyr, Trp, Arg
$X^5$: D-Pro
$X^6$: Pro, Sar, N-Me-Lys, N-Me-Lys(Ac)
$X^7$: Ala, Phe, Tyr, Trp

Embodiment 2.1 (SEQ ID NO: 31)

$X^1$: Ser, Gly, Thr
$X^2$: Leu, Nle
$X^3$: Ala
$X^4$: Leu, Ile, Nle, Val, Phe, Lys, Tyr, Trp, Arg
$X^5$: D-Pro, N-Me-D-lipophilic Amino acids
$X^6$: Pro, N-Me-Amino acids, N-Me-Lys, N-Me-Lys(Ac)
$X^7$: Ala, Leu, Ile, Nle, Val, Phe, Tyr, Trp Embodiment 2.2 (SEQ ID NO: 32)

$X^1$: Ser, Gly, Thr
$X^2$: Leu, Nle
$X^3$: Ala
$X^4$: Leu, Phe, Lys, Tyr, Trp, Arg
$X^5$: D-Pro, N-Me-D-lipophilic Amino acids
$X^6$: Pro, N-Me-Amino acids, N-Me-Lys, N-Me-Lys(Ac)
$X^7$: Ala, Leu, Ile, Nle, Val, Phe, Tyr, Trp Embodiment 2.3 (SEQ ID NO: 33)

$X^1$: Ser, Gly, Thr
$X^2$: Leu, Nle $X^3$: Ala
$X^4$: Leu, Phe, Lys, Tyr, Trp, Arg
$X^5$: D-Pro
$X^6$: Pro, N-Me-Amino acids, N-Me-Lys, N-Me-Lys(Ac)
$X^7$: Ala, Leu, Ile, Nle, Val, Phe, Tyr, Trp Embodiment 2.4 (SEQ ID NO: 34)

$X^1$: Ser, Gly, Thr
$X^2$: Leu, Nle
$X^3$: Ala
$X^4$: Leu, Phe, Lys, Tyr, Trp, Arg
$X^5$: D-Pro
$X^6$: Pro, Sar, N-Me-Lys, N-Me-Lys(Ac)
$X^7$: Ala, Leu, Ile, Nle, Val, Phe, Tyr, Trp

Embodiment 2.5 (SEQ ID NO: 35)

$X^1$: Ser, Gly, Thr
$X^2$: Leu, Nle
$X^3$: Ala
$X^4$: Leu, Phe, Lys, Tyr, Trp, Arg
$X^5$: D-Pro
$X^6$: Pro, Sar, N-Me-Lys, N-Me-Lys(Ac)
$X^7$: Ala, Phe, Tyr, Trp

Embodiment 2.6 (SEQ ID NO: 36)

$X^1$: Ser, Gly, Thr
$X^2$: Leu, Nle
$X^3$: Ala
$X^4$: Leu, Ile, Nle, Val, Phe, Lys, Tyr, Trp, Arg
$X^5$: D-Pro
$X^6$: Pro, N-Me-Amino acids, N-Me-Lys, N-Me-Lys(Ac)
$X^7$: Ala, Leu, Ile, Nle, Val, Phe, Tyr, Trp Embodiment 2.7 (SEQ ID NO: 37)

$X^1$: Ser, Gly, Thr
$X^2$: Leu, Nle
$X^3$: Ala
$X^4$: Leu, Ile, Nle, Val, Phe, Lys, Tyr, Trp, Arg
$X^5$: D-Pro
$X^6$: Pro, Sar, N-Me-Lys, N-Me-Lys(Ac)
$X^7$: Ala, Leu, Ile, Nle, Val, Phe, Tyr, Trp

Embodiment 2.8 (SEQ ID NO: 38)

$X^1$: Ser, Gly, Thr
$X^2$: Leu, Nle
$X^3$: Ala
$X^4$: Leu, Ile, Nle, Val, Phe, Lys, Tyr, Trp, Arg
$X^5$: D-Pro
$X^6$: Pro, Sar, N-Me-Lys, N-Me-Lys(Ac)
$X^7$: Ala, Phe, Tyr, Trp

Embodiment 2.9 (SEQ ID NO: 39)

$X^1$: Ser, Gly, Thr
$X^2$: Leu
$X^3$: Ala
$X^4$: Leu, Ile, Nle, Val, Phe, Lys, Tyr, Trp, Arg
$X^5$: D-Pro, N-Me-D-lipophilic Amino acids
$X^6$: Pro, N-Me-Amino acids, N-Me-Lys, N-Me-Lys(Ac)
$X^7$: Ala, Leu, Ile, Nle, Val, Phe, Tyr, Trp Embodiment 2.10 (SEQ ID NO: 40)

$X^1$: Ser, Gly, Thr
$X^2$: Leu

X³: Ala
X⁴: Leu, Phe, Lys, Tyr, Trp, Arg
X⁵: D-Pro, N-Me-D-lipophilic Amino acids
X⁶: Pro, N-Me-Amino acids, N-Me-Lys, N-Me-Lys(Ac)
X⁷: Ala, Leu, Ile, Nle, Val, Phe, Tyr, Trp Embodiment 2.11 (SEQ ID NO: 41)

X¹: Ser, Gly, Thr
X²: Leu
X³: Ala
X⁴: Leu, Phe, Lys, Tyr, Trp, Arg
X⁵: D-Pro
X⁶: Pro, N-Me-Amino acids, N-Me-Lys, N-Me-Lys(Ac)
X⁷: Ala, Leu, Ile, Nle, Val, Phe, Tyr, Trp Embodiment 2.12 (SEQ ID NO: 42)

X¹: Ser, Gly, Thr
X²: Leu
X³: Ala
X⁴: Leu, Phe, Lys, Tyr, Trp, Arg
X⁵: D-Pro
X⁶: Pro, Sar, N-Me-Lys, N-Me-Lys(Ac)
X⁷: Ala, Leu, Ile, Nle, Val, Phe, Tyr, Trp

Embodiment 2.13 (SEQ ID NO: 43)

X¹: Ser, Gly, Thr
X²: Leu
X³: Ala
X⁴: Leu, Phe, Lys, Tyr, Trp, Arg
X⁵: D-Pro
X⁶: Pro, Sar, N-Me-Lys, N-Me-Lys(Ac)
X⁷: Ala, Phe, Tyr, Trp

Embodiment 2.14 (SEQ ID NO: 44)

X¹: Ser, Gly, Thr
X²: Leu
X³: Ala
X⁴: Leu, Ile, Nle, Val, Phe, Lys, Tyr, Trp, Arg
X⁵: D-Pro
X⁶: Pro, N-Me-Amino acids, N-Me-Lys, N-Me-Lys(Ac)
X⁷: Ala, Leu, Ile, Nle, Val, Phe, Tyr, Trp Embodiment 2.15 (SEQ ID NO: 45)

X¹: Ser, Gly, Thr
X²: Leu
X³: Ala
X⁴: Leu, Ile, Nle, Val, Phe, Lys, Tyr, Trp, Arg
X⁵: D-Pro
X⁶: Pro, Sar, N-Me-Lys, N-Me-Lys(Ac)
X⁷: Ala, Leu, Ile, Nle, Val, Phe, Tyr, Trp

Embodiment 2.16 (SEQ ID NO: 46)

X¹: Ser, Gly, Thr
X²: Leu
X³: Ala
X⁴: Leu, Ile, Nle, Val, Phe, Lys, Tyr, Trp, Arg
X⁵: D-Pro
X⁶: Pro, Sar, N-Me-Lys, N-Me-Lys(Ac)
X⁷: Ala, Phe, Tyr, Trp

Embodiment 3.1 (SEQ ID NO: 47)

X¹: Ser, Gly, Thr
X²: Leu, Ile, Nle, Val, Phe

X³: Gly
X⁴: Leu, Phe, Lys, Tyr, Trp, Arg
X⁵: D-Pro, N-Me-D-lipophilic Amino acids
X⁶: Pro, N-Me-Amino acids, N-Me-Lys, N-Me-Lys(Ac)
X⁷: Ala, Leu, Ile, Nle, Val, Phe, Tyr, Trp Embodiment 3.2 (SEQ ID NO: 48)

X¹: Ser, Gly, Thr
X²: Leu, Ile, Nle, Val, Phe
X³: Gly
X⁴: Leu, Phe, Lys, Tyr, Trp, Arg
X⁵: D-Pro
X⁶: Pro, N-Me-Amino acids, N-Me-Lys, N-Me-Lys(Ac)
X⁷: Ala, Leu, Ile, Nle, Val, Phe, Tyr, Trp Embodiment 3.3 (SEQ ID NO: 49)

X¹: Ser, Gly, Thr
X²: Leu, Ile, Nle, Val, Phe
X³: Gly
X⁴: Leu, Phe, Lys, Tyr, Trp, Arg
X⁵: D-Pro
X⁶: Pro, Sar, N-Me-Lys, N-Me-Lys(Ac)
X⁷: Ala, Leu, Ile, Nle, Val, Phe, Tyr, Trp

Embodiment 3.4 (SEQ ID NO: 50)

X¹: Ser, Gly, Thr
X²: Leu, Ile, Nle, Val, Phe
X³: Gly
X⁴: Leu, Phe, Lys, Tyr, Trp, Arg
X⁵: D-Pro
X⁶: Pro, Sar, N-Me-Lys, N-Me-Lys(Ac)
X⁷: Ala, Phe, Tyr, Trp

Embodiment 3.5 (SEQ ID NO: 51)

X¹: Ser, Gly, Thr
X²: Leu, Ile, Nle, Val, Phe
X³: Gly
X⁴: Leu, Ile, Nle, Val, Phe, Lys, Tyr, Trp, Arg
X⁵: D-Pro
X⁶: Pro, N-Me-Amino acids, N-Me-Lys, N-Me-Lys(Ac)
X⁷: Ala, Leu, Ile, Nle, Val, Phe, Tyr, Trp Embodiment 3.6 (SEQ ID NO: 52)

X¹: Ser, Gly, Thr
X²: Leu, Ile, Nle, Val, Phe
X³: Gly
X⁴: Leu, Ile, Nle, Val, Phe, Lys, Tyr, Trp, Arg
X⁵: D-Pro
X⁶: Pro, Sar, N-Me-Lys, N-Me-Lys(Ac)
X⁷: Ala, Leu, Ile, Nle, Val, Phe, Tyr, Trp

Embodiment 3.7 (SEQ ID NO: 53)

X¹: Ser, Gly, Thr
X²: Leu, Ile, Nle, Val, Phe
X³: Gly
X⁴: Leu, Ile, Nle, Val, Phe, Lys, Tyr, Trp, Arg
X⁵: D-Pro
X⁶: Pro, Sar, N-Me-Lys, N-Me-Lys(Ac)
X⁷: Ala, Phe, Tyr, Trp

Embodiment 4.1 (SEQ ID NO: 54)

X¹: Ser, Gly, Thr
X²: Leu, Ile, Nle, Val, Phe

X³: Gly, Ala
X⁴: Leu, Phe, Lys, Tyr, Trp, Arg
X⁵: D-Pro
X⁶: Pro, N-Me-Amino acids, N-Me-Lys, N-Me-Lys(Ac)
X⁷: Ala, Leu, Ile, Nle, Val, Phe, Tyr, Trp Embodiment 4.2 (SEQ ID NO: 55)

X¹: Ser, Gly, Thr
X²: Leu, Ile, Nle, Val, Phe
X³: Gly, Ala
X⁴: Leu, Phe, Lys, Tyr, Trp, Arg
X⁵: D-Pro
X⁶: Pro, Sar, N-Me-Lys, N-Me-Lys(Ac)
X⁷: Ala, Leu, Ile, Nle, Val, Phe, Tyr, Trp

Embodiment 4.3 (SEQ ID NO: 56)

X¹: Ser, Gly, Thr
X²: Leu, Ile, Nle, Val, Phe
X³: Gly, Ala
X⁴: Leu, Phe, Lys, Tyr, Trp, Arg
X⁵: D-Pro
X⁶: Pro, Sar, N-Me-Lys, N-Me-Lys(Ac)
X⁷: Ala, Phe, Tyr, Trp

Embodiment 4.4 (SEQ ID NO: 57)

X¹: Ser, Gly, Thr
X²: Leu, Ile, Nle, Val, Phe
X³: Gly, Ala
X⁴: Leu, Phe, Lys, Tyr, Trp, Arg
X⁵: D-Pro
X⁶: Pro, N-Me-Amino acids, N-Me-Lys, N-Me-Lys(Ac)
X⁷: Ala, Phe, Tyr, Trp Embodiment 5.1 (SEQ ID NO: 58)

X¹: Ser, Gly, Thr
X²: Leu, Ile, Nle, Val, Phe
X³: Gly, Ala
X⁴: Leu, Ile, Nle, Val, Phe, Lys, Tyr, Trp, Arg
X⁵: D-Pro
X⁶: Pro, Sar, N-Me-Lys, N-Me-Lys(Ac)
X⁷: Ala, Leu, Ile, Nle, Val, Phe, Tyr, Trp

Embodiment 5.2 (SEQ ID NO: 59)

X¹: Ser, Gly, Thr
X²: Leu, Ile, Nle, Val, Phe
X³: Gly, Ala
X⁴: Leu, Ile, Nle, Val, Phe, Lys, Tyr, Trp, Arg
X⁵: D-Pro
X⁶: Pro, Sar, N-Me-Lys, N-Me-Lys(Ac)
X7: Ala, Phe, Tyr, Trp

Embodiment 5.3 (SEQ ID NO: 60)

X¹: Ser, Gly, Thr
X²: Leu, Ile, Nle, Val, Phe
X³: Gly, Ala
X⁴: Leu, Ile, Nle, Val, Phe, Lys, Tyr, Trp, Arg
X⁵: D-Pro
X⁶: Pro, N-Me-Amino acids, N-Me-Lys, N-Me-Lys(Ac)
X⁷: Ala, Phe, Tyr, Trp Embodiment 6.1 (SEQ ID NO: 61)

X¹: Ser, Gly, Thr
X²: Leu, Ile, Nle, Val, Phe

X³: Gly, Ala
X⁴: Leu, Ile, Nle, Val, Phe, Lys, Tyr, Arg
X⁵: D-Pro, N-Me-D-lipophilic Amino acids
X⁶: Pro, Sar, N-Me-Lys, N-Me-Lys(Ac)
X⁷: Ala, Phe, Tyr, Trp

5.3. Modified Compounds of the Invention

The present invention also pertains to modified compounds. These are compounds of the present invention, as specified above, wherein at least one effector moiety X⁸ is bonded to the peptide via a suitable linker L. The linker may also be multivalent to allow for the bonding of two or more compounds of the present invention and/or two or more effector moieties X⁸. Preferably, the linker according to this embodiment has a total of 3-6 valencies and more preferably 3-5 valencies. The additional one or more valencies of the linker may be used for bonding additional compounds of the invention and/or additional effector moieties.

Specific embodiments of the present invention may thus be characterized by the following general formula (II):

$$(X^0)_{n1}L(X^8)_{n2} \qquad (II)$$

wherein X⁰ represents the peptide compound of the invention as specified above (excluding one hydrogen atom to allow bonding to the linker), L represents the linker, X⁸ represents the effector moiety and wherein n1 and n2 are each independently selected from the range of 1 to 5 wherein n1+n2 represents the number of valencies of the linker and is preferably in the range of from 2 to 6, more preferably 3-5 with the proviso that each of n1 and n2 is at least 1. A preferred modified compound of the present invention is the compound, wherein n1=1 and n2=1, i.e. compounds of the following general formula (IIa):

$$X^0\text{-}L\text{-}X^8 \qquad (IIa)$$

wherein the meanings of X⁰, L and X⁸ are the same as described above.

5.3.1 Position of Modification

In principle, the position of the modification is not particularly restricted, provided that said modification does not significantly affect strength and selectivity of the compound's binding to the αvβ6 integrin. Within the scope of this condition, modified compounds of the invention may be derived from the above specified peptide compounds by replacing any hydrogen atom by -L-X⁸. This includes all of the compounds of the invention described above, wherein the compounds described above as preferred are also preferred in the context of this modification.

Considering that the stretch of amino acids R—X¹-D is believed to be most significant for binding to αvβ6 integrin, it is a preferred embodiment of this aspect of the present invention to modify the inventive peptide compound in the position of one of the remaining residues X², X³, X⁴, X⁵, X⁶ or X⁷. It is even more preferred to modify one of residues X⁴, X⁵, X⁶ or X⁷. Most preferably, residue X⁶ is modified.

Within the scope of this most preferred embodiment, it is particularly advantageous to use N-Me-Lys as residue X⁶ and to bind the modifying moiety -L-X⁸ via the ω-amino group. Hence, it is particularly preferred in the context of this embodiment to use the above-mentioned compounds of the present invention, wherein X⁶ represents N-Me-Lys.

Bonding of the modifying moiety -L-X⁸ can, for instance, be done by formation of an amide bond by reacting said ω-amino group with an activated carboxyl group forming a terminal group of the linker L. Of course, other functional groups may also be used for attaching the linker to the target amino acid residue and preferably the amino group of residue $X^6$ being N-Me-Lys.

5.3.2 Linker

The linker group L can be any bivalent atomic group wherein the shortest distance between the two valences is from 3 to 60 covalent bonds, preferably from 5 to 40 covalent bonds, more preferably from 8 to 30 covalent bonds.

The linker may consist of or contain linear, branched and/or cyclic structural elements typically consisting of atoms selected from C, H, N, O, S and P. The total number of heavy atoms (i.e atoms other than hydrogen) in the linker (including optionally present substituents) may be within the range of 2 and 250, preferably 4 to 100 and more preferably 7 to 60.

The linker may also carry one or more substituents. Such substituents are preferably selected from the substituents defined above and more preferably from the group consisting of amino, halogen, cyano, nitro, carboxylic acid, carboxylic ester, $C_1$-$C_{20}$ alkyl, $C_2$-$C_{20}$ alkenyl, $C_3$-$C_{20}$ alkynyl, $C_3$-$C_{20}$ cycloalkyl, $C_4$-$C_{20}$ cycloalkenyl, $C_8$-$C_{20}$ cycloalkynyl, $C_6$-$C_{20}$ aryl, $C_1$-$C_6$ alkyl-$C_6$-$C_{20}$ aryl, heteroaryl, 5-7-membered heterocycle having one or more heteroatoms selected from the group consisting of N, O, S and P.

Preferred structural elements contained in the linker are selected from ethylene glycol, polyethylene glycol (PEG) such as PEG with 2-15 ethylene glycol repeating units, propylene glycol, poly propylene glycol (PPG) such as PPG with 2-15 propylene glycol repeating units, amino acids, oligopeptides such as $(Gly)_m$ with m=2-15, saccharides such as galactose and oligosaccharides such as saccharose and other oligosaccharides with 2-15 monsaccharide repeating units. Further structural elements that may be contained in the linker are alkylene groups, alkenylene groups or alkynylene groups, each of them preferably having 2-20 carbon atoms and each of them optionally having incorporated therein one or more carbonyl groups and/or optionally being substituted as explained above. Said structural elements advantageously carry functional groups at their termini to allow bonding to $X^0$, $X^8$ or to other linker structural elements. Said functional groups are preferably derived from hydroxyl groups, amino groups, and carboxyl groups.

Of course, these structural elements can also be combined. Preferred linkers are disclosed in "Ligands for Mapping αvβ3-Integrin Expression in Vivo" by M. Schottelius et al. in *Acc. Chem. Res.* 2009, 42, 969-980, especially the linkers forming part of the structures shown in FIGS. 12 and 14.; "Dimerization of a Phage-Display Selected Peptide for Imaging of αvβ6-Integrin: Two Approaches to the Multivalent Effect" by A. N. Singh et al. in Theranostics 214, 4, 756-760, especially as shown in Scheme 1. A further linker is shown in "Synthesis and biological evaluation of a peptide-paclitaxel conjugate which targets the integrin αvβ6" by S. Li et al. in *Bioorganic & Medicinal Chemistry* 2011, 19, 5480-5489, and especially the compounds of FIG. 1. Of course, it is also possible to combine two or more different structural elements mentioned above to form a linker.

At its termini, the linker may contain active functional groups to facilitate bonding to the cyclic peptide compound of the invention and bonding to the effector moiety $X^8$.

According to another preferred embodiment, a linker is used, which contains a hydrolysable group that allows to cleave the two linked moieties. The use of such a cleavable linker may be advantageous, e.g. when the peptide compound $X^0$ is used in order to target a therapeutically active effector moiety $X^8$ (e.g. a cytotoxic agent) to a cell which expresses the αvβ6 integrin (see below). Suitable hydrolysable groups can be selected from ester such as —C(O)—O— and —O—C(O)—, amide (peptide) such as —C(O)—NH— and —NH—C(O)—, carbamate such as —NH—C(O)—O— and —O—C(O)—NH—, urea such as —NH—C(O)—NH— and anhydride such as —C(O)—O—C(O)—. It is of course possible to combine two or more of these hydrolysable groups and/or to combine one or more of these hydrolysable groups with one or more of the optionally substituted linker groups specified above.

5.3.3 Effector Moiety $X^8$

The effector moiety can be a moiety suitable for labelling the compound of the invention, for instance in labelling for imaging purposes such as fluorescence labelling, positron emission tomography (PET), single-photon emission computed tomography (SPECT), optical imaging or magnetic resonance imaging (MRI), X-ray based CT imaging, scintigraphy, ultrasonography and thermography.

Suitable effector moieties for labeling the compounds of the invention are disclosed, for instance, in "Instrumentation and probes for molecular and cellular imaging" by Lecchi et al. in The Quarterly Journal of Nuclear Medicine and Molecular Imaging 2007, 51, 111-26, in "Ligands for Mapping αvβ3-Integrin Expression in Vivo" by M. Schottelius et al. in Acc. Cem. Res. 2009, 42, 969-980, in Scheme 1 of "Dimerization of a Phage-Display Selected Peptide for Imaging of αvβ6-Integrin: Two Approaches to the Multivalent Effect" by A. N. Singh et al. in Theranostics 214, 4, 756-760, in WO 01/05810 especially on page 12, lines 1 to 19 and the reference "The Molecular Probes® Handbook-A Guide to Fluorescent Probes and Labeling Technologies", 11$^{th}$ Edition, 2010 by Molecular Probes, Inc./ThermoFisher Scientific.

Effector moieties that can be used as labels for SPECT or PET imaging include various radioisotopes and atomic groups containing one or more of such radioisotopes. If the radioisotope is a metal atom, it is preferred to bind it in the form of a chelate complex. Suitable chelating groups can be selected from 1,10-phenanthroline, ethylene diamine tetraacetic acid, 2,2'-bipyridine, DOTA, NODAGA (see e.g. S. Neubauer et al. *Angew. Chem. Int. Ed.* 2013, 52, 11656-9), or NOPO (J. Šimeček, J. Notni, T. G. Kapp, H. Kessler, H.-J. Wester, *Molecular Pharmaceutics* 2014, 11, 1687-95), TRAP (J. Notni, J. Šimeček, P. Hermann, H.-J. Wester. "TRAP, a Powerful and Versatile Framework for Gallium-68 Radiopharmaceuticals" *Chem. Eur. J.* 2011, 17, 14718-14722.) Suitable chelate complexes of $^{99m}Tc$ are disclosed in "$^{99m}$Tc-Labeled Cystine Knot Peptide Targeting Integrin αvβ6 for Tumor SPECT Imaging" by X. Zhu et al. in *Molecular Pharmaceutics* 2014, 11, 1208-1217. Non-metal radioisotopes are preferably bonded in a covalent manner to organic groups. Suitable atomic groups carrying non-metal radioisotopes are disclosed in the Wikipedia entry "List of PET radiotracers" (version of Sep. 16, 2015).

Effector moieties that can be used for radio imaging may thus include various radioisotopes and atomic groups (such as chelate complexes) containing the same. Suitable radioisotopes include $^{11}C$, $^{13}N$, $^{15}O$, $^{18}F$, $^{64}Cu$, $^{68}Ga$, $^{88}Y$, $^{89}Zr$, $^{90}Y$, $^{99m}Tc$, $^{111}In$, $^{123}I$, $^{124}I$, $^{131}I$ and $^{177}Lu$. Among these radioisotopes, it is advantageous to use $^{99m}Tc$, $^{111}In$, $^{123}I$ or $^{131}I$ for SPECT imaging and to use $^{11}C$, $^{13}N$, $^{15}O$, $^{18}F$, $^{68}Ga$, $^{82}$Rb or $^{89}$Zr for PET imaging. Materials suitable for use as effector moieties (after bonding to the linker L) are listed in the Wikipedia entries for "Single-photon emission computed tomography", "List of PET radiotracers" (in their versions of Sep. 16, 2015). The Wikipedia entry "Medicinal radiocompounds" (version of Sep. 16, 2015) provides further information on such compounds.

Imaging with the MRI technique can be effected by using a suitable contrast agent as the effector moiety $X^8$. Most preferred are Gd(III) chelate complexes. A description of suitable contrast agents is found, for instance, in the Wikipedia entry "MRI Contrast Agent" (version of Sep. 16, 2015) and documents cited therein. Chelate complexes may be the same as discussed above for the effector moieties for use in SPECT or PET imaging.

Effector moieties that can be used for fluorescence labeling include labels by ThermoFisher commercially available as Cy® series such as CY® 3, 5, 5.5, 7, 7.5 and the AlexaFluor® series such as AlexaFluor® 350, 405, 488, 532, 546, 555, 568, 594, 647, 680, and 750 as well as Fluorescein, Pyren, Rhodamin, BODIPY dyes and their analogues.

Effector moieties and that can be used for imaging by X-ray-based technology may include, for instance, iodine and atomic groups containing iodine. Materials suitable for use as effector moieties (after bonding to the linker L) are listed in the Wikipedia entry "Radiocontrast agent" (version of Sep. 16, 2015).

The effector moiety can also be a moiety having therapeutic activity. For instance, the effector can also represent a toxic reagent for a selective killing of αvβ6 carrying cells (personalized medicine).

Suitable effector moieties for use as therapeutic agents can be any active drug molecule suitable for the treatment of a medical indication or condition wherein αvβ6 integrin is upregulated or involved in the pathologic mechanism in another way. Preferably it is a drug for the treatment of cancer, a virus disease or fibrosis.

More specifically, the therapeutic drug against cancer may be selected from therapeutic drugs suitable for treating cancer. For instance, the anticancer drug may be selected from the group consisting of alkylating agents, anti-metabolites, anthracyclines, plant alkaloids, topoisomerase inhibitors and other anti-tumor drugs. More specifically, the following can be mentioned: platinum based compounds, antibiotics with anti-cancer activity, anthracyclines, anthracenediones, alkylating agents, antimetabolites, Antimitotic agents, taxanes, taxoids, microtubule inhibitors, Vinca alkaloids, folate antagonists, topoisomerase inhibitors, antiestrogens, antiandrogens, aromatase inhibitors, GnRh analogs, inhibitors of 5α-reductase, bisphosphonates, a metabolic inhibitor, preferably a mTOR inhibitor; an epigenetic inhibitor, preferably a DNMT inhibitor; an anthracycline antibiotic; a camptotheca; an anthracycline; histone deacetylase (HDAC) inhibitors, proteasome inhibitors, JAK2 inhibitors, tyrosine kinase inhibitors (TKIs), PI3K inhibitors, Protein kinase inhibitors, Inhibitors of serine/threonine kinases, inhibitors of intracellular signaling, inhibitors of Ras/Raf signaling, MEK inhibitors, AKT inhibitors, inhibitors of survival signaling proteins, cyclin dependent kinase inhibitors, therapeutic monoclonal antibodies, TRAIL pathway agonists, anti-angiogenic agents, metalloproteinase inhibitors, cathepsin inhibitors, inhibitors of urokinase plasminogen activator receptor function, immunoconjugates, antibody drug conjugates, antibody fragments, bispecfic antibodies, bispecific T cell engagers (BiTEs). Said anticancer drug is preferably selected from the group consisting of 5-fluorouracil, cisplatin, irinotecan hydrochloride, epirubicin, paclitaxel, docetaxel, camptothecin, doxorubicin, rapamycin, 5-azacytidine, doxorubicin irinotecan, topotecan (type 1 topoisomerase inhibitors), amsacrin, etoposide, etoposide phosphate and teniposide (topoisomerase-type 2 inhibitors); UFT, capecitabine, CPT-II, oxaliplatin, cyclophosphamide, methotrexate, navelbine, epirubicin, mitoxantrone, raloxifen, mitomycin, carboplatinum, gemcitabine, etoposide and topotecan.

The therapeutic drug may also be an antibody selected from cetuximab, panitumumab, nimotuzumab, trastuzumab, pertuzumab, rituximab, ofatumumab, veltuzumab, alemtuzumab, labetuzumab, adecatumumab, oregovomab, onartuzumab; apomab, mapatumumab, lexatumumab, conatumumab, tigatuzumab, catumaxomab, blinatumomab, ibritumomab triuxetan, tositumomab, brentuximab vedotin, gemtuzumab ozogamicin, clivatuzumab tetraxetan, pemtumomab, trastuzumab emtansine, bevacizumab, etaracizumab, volociximab, ramucirumab, aflibercept.

Yet another possibility is to use an atomic group containing a radioisotope for use in radiotherapy. Suitable radioisotopes and atomic groups containing the same as well as their applications are described in the German language Wikipedia entry "Radionuklidtherapie" (version of Sep. 16, 2015). These substances can be used in the context of the present invention by covalently bonding to the peptide compound $X^0$ of the present invention via linker L.

Such therapeutic drugs are disclosed, for instance, in "Cancer Drugs" by Judith Matray-Devoti, Chelsea House, 2006; "Physicians' Cancer Chemotherapy Drug Manual 2015" by Edward Chu, Vincent T DeVita, Jr., Jones & Bartlett Learning 2015; "Cancer Chemotherapy and Biotherapy: Principles and Practice" by Bruce A. Chabner, Dan L. Longo, Wolters Kluwer, 2011; "Drugs in Cancer Care" by Rachel Midgley, Mark R. Middleton, Andrew Dickman, David Kerr (Eds.), Oxford University Press 2013. The drugs disclosed in these books can be used as therapeutic agents when practicing the present invention. The disclosures of therapeutic drugs in these references is therefore incorporated herein.

The therapeutic drug for treatment of a virus disease may be a therapeutic drug suitable for treatment of a virus disease selected from the group consisting of antiviral drugs for suppressing HCMV proliferation such as ganciclovir, foscarnet, valganciclovir; virus neuraminidase inhibitors such as tamiflu (oseltamivir) and relenza (zanamivir); interferon-alpha; in Hepatitis B, oral anti-viral agents such as lamivudine or adefovir can be used; in Hepatitis C, ribavirin, sofosbuvir, ledipasvir, faldaprevir can be used; in influenza substances destroying influenza virus M2 protein ion channel activity such as amantadine and rimantadine. Further antiviral drugs can be used such as arbidol. Such therapeutic drugs are disclosed, for instance, in "Antiviral Drugs" by John S. Driscoll, Wiley, 2002, "Antiviral Drug Strategies" by Erik De Clercq, Wiley VCH, 2011, "Antiviral Strategies" by Hans-Georg Krausslich, Ralf Bartenschlager, Springer 2009; "Current Trends in Antiviral Drug Development; Antivirals: latest developments and future progress" Henry Stewart Talks, 2013; "A Practical Guide to Clinical Virology" by L. R. Haaheim, John R. Pattison, Richard J. Whitley, Wiley, 2002.

The therapeutic drug for the treatment of fibrosis may be selected from therapeutic drugs suitable for the treatment of fibrosis. Such therapeutic drugs are disclosed, for instance, in "Cystic Fibrosis in the 21st Century" by Andrew Bush (Ed.), S. Karger, 2006; "Liver Fibrosis: New Insights for the Healthcare Professional: 2013 Edition" by Q. Ahton Acton, ScholarlyEditions, 2013; "Idiopathic Pulmonary Fibrosis: A Comprehensive Clinical Guide" by Keith C. Meyer, Steven D. Nathan, Springer, 2014; "New Insights into the Pathogenesis and Treatment of Idiopathic Pulmonary Fibrosis: A Potential Role for Stem Cells in the Lung Parenchyma and Implications for Therapy" by M. Gharaee-Kermani et al. in Pharmaceutical Research, 2007, 24, 819-841; "Pulmonary Fibrosis: pathogenesis, etiology and regulation" by M. S. Wilson and T. A. Wynn in Mucosal Immunol. 2009, 2, 103-121. Specific preferred therapeutic drugs are preferably selected from the drugs and drug classes disclosed listed in Table II of the review article by Gharaee-Kermani et al. cited above.

In addition to the above-mentioned drugs, it is also possible to use a nucleic acid-based drug. This can be, for instance, siRNA drugs, antisense nucleic acid drugs, ribozymes, plasmid DNA for gene therapy. Suitable drugs of this type are disclosed, for instance, in "Nucleic Acid-Based Drugs" by J. P. Wong (Ed.), Future Science Ltd. 2013 and "From Nucleic Acids Sequences to Molecular Medicine" by V. A. Erdmann and J. Barciszewski (Eds.) Springer 2012. Such nucleic acid-based drug concepts can be applied to the treatment of any one of the medical indications mentioned herein, including cancer, virus diseases and fibrosis.

When attaching the effector moieties $X^8$ listed above to the linker L, it is advantageous to covalently bind the linker to a position within the effector moiety, such that the binding of the linker does not interfere with the therapeutic activity of the effector moiety.

Alternatively, the effector moiety can be an anchor group that allows to attach the compound of the invention to a surface of a greater entity such as the surface of a medical device such as a stent for prevention of proliferation and/or restenosis. The compound of the invention may also be attached to the surface of a diagnostic device to allow testing for cells and associated pathologies, wherein the αvβ6 integrin is upregulated. Yet another possible use is the attachment of the compound of the invention to a chromatography column carrier material to thereby allow isolating and/or purifying the αvβ6 integrin or biological materials containing the same. Suitable anchor groups for these possible applications are disclosed as "organic anchoring groups" in WO2007/065691 A, for instance in Embodiment 5 of this patent document.

The anchor group can also be used for attaching the compound of the invention to a liposome or other vesicle, for instance for using the compound of the present invention in drug targeting. Suitable liposome compositions and related vesicles as well as their synthesis are disclosed, for instance in WO2010/113984, EP2153820 A1, WO2008/120736, WO2014/065245, US2013/136790 A1, WO2014/025042, US2014/112979 A1, WO2004/091578 A2, WO2004/047802 A2 and on page 22 of WO 01/05810 A2 and also in "Lipid Nanoparticles: Production, Characterization and Stability" by R. Shah, Springer 2015. Attachment can be accomplished via covalent or non-covalent (such as ionic, hydrogen-bonding or hydrophobic) interactions. Suitable anchor groups can be selected taking the surface chemistry of the target surface into account. If the anchor group is to be attached to a liposome or other lipid-based vesicle, preferred interactions are ionic interactions and even more preferably hydrophobic interactions between the hydrophobic parts of the liposome-forming lipids (typically phospholipids) and the anchor group. Suitable anchor groups for this purpose are groups derived from lipid molecules wherein the lipid molecules are the same as the lipid molecules forming the liposome or are lipid molecules capable of being incorporated into the liposome lipid bilayer.

The anchor group may also be used for covalently bonding the compound of the invention to a carrier such as polymeric nanoparticles or viral nanoparticles. Suitable anchor groups therefore include functional groups that can react with functional groups present on the carrier. These can be functional groups suitable for ester or amide bond formation as well as functional groups suitable for "click chemistry" as disclosed in the Wikipedia entry "Click chemistry" (version of Sep. 16, 2015) and references cited therein. For instance, it is advantageous to use azide groups and alkyne groups for copper catalyzed [3+2]cycloadditions. This approach is described by M. L. Hovlid et al. in "Guiding plant virus particles to integrin-displaying cells" in *Nanoscale* 2012, 4, 3698 and in "A shortcut to high-affinity Ga-68 and Cu-64 radiopharmaceuticals: one-pot click chemistry trimerisation on the TRAP platform" by Z. Baranyai et al. in *Dalton Trans.*, 2015, 44, 11137. The synthetic approaches taken in these articles may be adapted to the use of the compound of the present invention. In a preferred embodiment of the compound of the above formula (IIa), the linker and effector together are represented by one of the moieties —(C=O)—(CH$_2$)$_n$—C≡CH and —(C=O)—(CH$_2$CH$_2$O)$_m$—C≡CH, with n and m being individually selected from the group 1, 2, 3, 4, 5, 6, 7, 8, 9 and 10, which is bonded to the terminal amino group of the N-methyl-lysine residue of $X^6$ by amide bond formation. It is similarly preferred if an azide group is bonded to this residue, for instance via amide bonding of one of the following moieties —(C=O)—(CH$_2$)$_n$—N3 and —(C=O)—(CH$_2$CH$_2$O)$_m$—C≡CH, with n and m being again selected from the group 1, 2, 3, 4, 5, 6, 7, 8, 9 and 10. Of course, the above-mentioned Click chemistry may also be used for forming a 5-membered N-containing heterocyclic group as mentioned in Section 5.3.2 above as a linker element for attaching other effector moieties as listed above.

Attaching the compound of the invention to a liposome or other vesicle may allow to use the compound of the invention as a targeting moiety for specifically delivering the liposome or other vesicle and their respective contents to a target cell. The resulting increase in local concentration in the vicinity of the target cell may permit to accomplish increased therapeutic efficacy without concomitant increase in side effects. It may even be possible to accomplish internalization of the active agent by the target cell via active transport mechanisms in analogy to S. Lucie et al. "Clustering and Internalization of Integrin αvβ3 With a Tetrameric RGD-synthetic Peptide" in *Molecular Therapy* 2009, 17, 837-843.

The effector moiety together with the linker may also be suitably selected to create a functional chimeric T cell antigen receptor that can be used for immunotherapy applications e.g. in the treatment of cancer. Suitable methods and materials may be adapted from "Conversion of a tumor-binding peptide identified by phage display to a functional chimeric T cell antigen receptor" by C. R. J. Pameijer et al. in Cancer Gene Therapy 2007, 14, 91-97.

The effector moiety encompasses not only the active atom or atom group (e.g. a radioactive atom in case of radiolabeling) but also the additional atoms or atomic groups used for bonding of the active atom or atomic group. For instance, the effector moiety may encompass the ligands and chelators shown in FIGS. 4 and 7 of "Ligands for Mapping αvβ3-Integrin Expression in Vivo" by M. Schottelius et al. in *Acc. Chem. Res.* 2009, 42, 969-980 (together with suitably selected active atoms) and also the complexes of active atom and ligand as shown in FIGS. 4, 6, 10, 11, 12 and 14 of this article. In case of doubt, if it is not clear which atoms form part of the linker and which atoms form part of the effector moiety, the effector moiety is to be understood as comprising only the active atom or atomic group, the smallest atomic group (functional group) required for bonding the active atom or atomic group and the atom or atomic group (functional group) required for bonding the effector moiety to a terminus of the linker.

5.4. Synthesis of Compounds of the Invention

The compounds of the invention can be synthesized using standard peptide methodology such as solid phase peptide synthesis using Fmoc as a protective group. The available techniques are described for instance in J. Chatterjee, B. Laufer, H. Kessler, *Nat. Protoc.* 2012, 7, 432-444.

Cyclization of the peptide can be effected using standard techniques. For instance, cyclization can be accomplished on the solid support or in solution using HBTU/HOBt/DIEA, PyBop/DIEA or PyClock/DIEA reagents. The available cyclization methods are described for instance in J. Chatterjee, B. Laufer, H. Kessler, *Nat. Protoc.* 2012, 7, 432-444 and references cited therein.

5.5. Pharmaceutical Compositions

The compounds of the present invention can be formulated with excipients to yield pharmaceutical compositions. These can be pharmaceutical compositions for oral or parenteral administration including for instance intravenous administration, intramuscular administration, transdermal administration, transmucosal administration, pulmonary administration, intranasal administration, as well as any other administration form that allows to present the compound of the present invention to the target cells wherein the αvβ6 integrin is upregulated or involved in the pathologic mechanism in another way.

Pharmaceutical compositions for parenteral administration including intravenous administration, intramuscular administration, transdermal administration, transmucosal administration, pulmonary administration, and intranasal administration can be made using the methods and materials disclosed in "Pharmaceutical Dosage Forms: Parenteral Medications" by Kenneth E. Avis, Herbert A. Lieberman, Leon Lachman, M. Dekker, 1993 and in "Remington The Science and Practice of Pharmacy" Edited by Allen, Loyd V., Jr, Pharmaceutical Press, 22$^{nd}$ Ed. 2012; "Pharmazeutische Technologie: Moderne Arzneiformen" by R. H. Müller and G. E. Hildebrand, WVG, 2$^{nd}$ Ed. 1998, "Arzneiformen richtig anwenden" by Kircher, Wolfgang, Deutscher Apotheker Verlag, 3$^{rd}$ Ed. 2007; "Lehrbuch der Pharmazeutischen Technologie: Mit einer Einführung in die Biopharmazie" by Kurt H. Bauer, Karl-Heinz Frömming, Claus Führer, W V G 2012; "Pharmazeutische Technologie: Für Studium und Beruf (Wissen und Praxis)" by Alfred Fahr, Rudolf Voigt, Deutscher Apotheker Verlag, 12$^{th}$ Ed. 2015.

Pharmaceutical compositions for oral administration can be made using the methods and materials disclosed in Pharmaceutical Dosage Forms: Tablets, Second Edition, Volume 3 by Herbert A. Lieberman et al., Taylor & Francis 1990; "Die Tablette" by A. Bauer-Brandl, W. A. Ritschel, Editio Cantor Verlag, 3$^{rd}$ Ed. 2011 as well as the documents cited above in relation to parenteral administration forms.

Further available formulation strategies are described and discussed, for instance, in Ther. Deliv. 2015 February; 6(2):149-63 *"Challenges in the delivery of peptide drugs: an industry perspective"* by Lewis A L1, Richard J.; Biotechnol. Adv. 2015 Feb. 14. pii: S0734-9750(15)00023-3. doi: 10.1016/j.biotechadv.2015.01.010. [Epub ahead of print] *"Recent advances in topical delivery of proteins and peptides mediated by soft matter nanocarriers"* by Witting, Obst, Friess, Hedtrich; Protein Pept Lett. 2014; 21(11):1087-101, *"Novel non-invasive protein and peptide drug delivery approaches"* by Wallis L, Kleynhans E, Toit T D, Gouws C, Steyn D, Steenekamp J, Viljoen J, Hamman J; Protein Pept Lett. 2014; 21(11): 1102-20, *"Recent advances in protein and Peptide drug delivery: a special emphasis on polymeric nanoparticles"* by Patel A, Patel M, Yang X, Mitra A K; and Curr Drug Deliv. 2007 April; 4(2):141-51, *"Recent advances in protein and peptide drug delivery systems"* by Malik DK1, Baboota S, Ahuja A, Hasan S, Ali J; and ACS Symposium Series Vol. 567 *"Formulation and Delivery of Proteins and Peptides"* by American Chemical Society 1994, Cleland J L and Langer R (Eds.).

5.6. Use as therapeutic Drug

5.6.1. Treatment of Cancer

Due to their highly active and selective binding to αvβ6 integrin, the compounds of the present invention can be used for treating those types of cancer, wherein αvβ6 integrin is upregulated or otherwise involved in the pathologic mechanism. Such types of cancer include head and neck squamous cell carcinoma such as oral squamous cell carcinoma, laryngeal squamous cell carcinoma, oropharyngeal squamous cell carcinoma, nasopharyngeal squamous cell carcinoma, hypopharyngeal squamous cell carcinoma. Other types of cancer that can be treated with the compounds of the invention include colon cancer, ovarian carcinoma, non-small cell lung cancer (NSCLC) and gastric cancer. Such cancers may be treated in any mammal and preferably in humans.

The compounds of the present invention may be administered to the patient for instance by intravenous, transmucosal, transdermal, intranasal administration. Suitable dosages may be in the range of 0.1 to 2000 mg/day, preferably 1 to 1000 mg/day. The compounds of the present invention may be administered once daily, twice a day, three times a day, etc. for any period of time, wherein multiple periods of time may be interrupted by one or more periods of time where the compounds of the present invention are not administered.

The compounds of the present invention may also be used as a component in combination therapy. They may be combined with one or more other therapeutic agents effective in the treatment of cancer such as the therapeutic agents listed above and/or below. Such combination therapy may be carried out by simultaneously or sequentially administering the two or more therapeutic agents.

5.6.2. Treatment of Fibrosis

The compounds of the present invention may also be used for treating fibrosis and in particular where αvβ6 integrin is upregulated, e.g. among others, pulmonary fibrosis, cystic fibrobis, idiopatic pulmonary fibrosis, endomyocardial fibrosis, Crohn's disease, and arthofibrosis.

The compounds of the present invention may be used for the treatment of fibrosis by any suitable administration form including intravenous, transmucosal, pulmonary, and intranasal administration. Dosages and administration schemes can be the same as specified above for the treatment of cancer. Combination therapy is also possible, wherein the one or more other therapeutic agents is selected from other therapeutic agents suitable for the treatment of fibrosis, for instance as cited above by cross-reference to the review article by Gharaee-Kermani et al. The compounds of the present invention as well as the one or more other therapeutic agents can be administered simultaneously or sequentially.

5.6.3. Treatment of Virus Diseases

The $\alpha v \beta 6$ integrin is used by certain types of viruses to enter the host cells. These are, for instance, Foot-and-Mouth-Disease Virus, human parechovirus 1 and coxsackievirus A9, which is causative for meningitis and other medical conditions. The compounds of the present invention can be used for treating such virus diseases by blocking entry of the virus into the host cell.

The compounds of the present invention may be used for the treatment of such virus diseases by any suitable administration form including intravenous, transmucosal, pulmonary, intranasal and intramuscular administration. Dosage and administration schemes can be the same as described above with respect to the treatment of cancer. Combination therapy involving the compounds of the present invention as well as one or more other antiviral drugs is feasible, too. In this case, the compounds of the present invention and the one or more other antiviral drugs, e.g. as listed above, can be administered simultaneously or sequentially.

5.6.4. Treatment of Other Medical Conditions

In addition to the above-mentioned medical conditions, the compounds of the present invention are also suitable for the treatment of medical conditions and selected from cornea dysfunctions, interstitial lung disease, thrombosis, myocardial infarction, coronary myocardial disease, arteriosclerosis, osteoporosis, inflammation, psoriasis, and open wounds.

Suitable dosages, administration forms, administration schemes, patient groups, etc. can be identified by the person skilled in the art relying on common general knowledge and routine procedure.

5.7. Use as Diagnostic Agent

Compounds of the present invention are also suitable for use as diagnostic agent. In this case, compounds of the present invention of general formula (II) are advantageously used, wherein the effector moiety $X^8$ is a labeling group as described above. Depending on the chosen analytical/diagnostic method to be used, a suitable labeling group is selected. The chosen analytical/diagnostic method also determines the dosage, form and timing of the administration of the diagnostic agent of the present invention.

The diagnostic agents of the present invention are suitable for virtually any analytical/diagnostic method that involves the use of diagnostic agents. The diagnostic agents of the present invention are particularly suitable for imaging methods such as fluorescence-based imaging, positron emission tomography (PET), single-photon emission computed tomography (SPECT), optical imaging or magnetic resonance imaging (MRI), X-ray based CT imaging, scintigraphy, ultrasonography and thermography.

5.8. Use for Drug Targeting

The compounds of the present invention may also be used as targeting agents together with other therapeutic agents and suitable carriers. Typically, the other therapeutic agent is contained within a suitable carrier whereas the compounds of the present invention are attached to the surface of the carrier. Selective binding of the compounds of the present invention to the $\alpha v \beta 6$ integrin gives rise to an increased local concentration of the targeting complex including the other therapeutic agent in the vicinity of the target cells. This local increase in concentration of the other therapeutic agent may favorably improve the ratio of beneficial therapeutic effects to undesired side effects.

Suitable carriers for drug targeting may be selected from liposomes, nanoparticles including polymeric nanoparticles and viral nanoparticles, micelles, microspheres made of biodegradable polymer, etc. Materials and methods that can be used in the present invention are discussed in US2015/0202316 A1, US2014/178296 A1, CN103446053 A, CN103520207 A, TW201121573 A, "Guiding plant virus particles to integrin-displaying cells" by M. L. Hovlid et al. in *Nanoscale* 2012, 4, 3698, "Solid-phase-assisted synthesis of targeting peptide-PEG-oligo(ethane amino)amides for receptor-mediated gene delivery" by I. Martin et al., *Org. Biomol. Chem.* 2012, 10, 3258 and "Advanced targeted therapies in cancer: Drug nanocarriers, the future of chemotherapy" by Pérez-Herrero E., Fernández-Medarde A., *Eur. J. Pharm. Biopharm.* 2015, 93, 52-79 and references cited therein. Of course, it will be necessary to substitute the targeting moieties and possibly also drug agents described in these documents by the compound of the present invention. Depending on the intended use, it may also be appropriate to replace the therapeutic agents and/or imaging agents of these documents by the therapeutic agents and/or imaging agents appropriate for the intended use.

The other therapeutic agent to be targeted is not particularly limited. It is, of course, reasonable to use the drug targeting approach for treating a medical condition, wherein $\alpha v \beta 6$ integrin is upregulated or otherwise involved in the pathologic mechanism. Hence, the other therapeutic agent is advantageously selected among therapeutic agents that are suitable for treating a medical condition of this type including especially the drugs disclosed above.

Suitable drug targeting concepts are described by U. Kiran Marelli et al. in "Tumor targeting via integrin ligands" in Frontiers in Oncology, 2013, 3, 1-12. The drug targeting concepts and especially the carrier systems and drugs disclosed in this review article and the documents cited therein may also be used in the context of the present invention.

5.9. Use for Biomolecular Research

The compounds of the present invention may also be used for obtaining additional information on molecular mechanisms underlying particular medical conditions of interest, as ligands for purifying $\alpha v \beta 6$ integrin in affinity chromatography columns, or for FACS analysis. The compounds of the present invention can also be used for investigating individual integrin functions and/or cross talk between different integrin types. The present invention thus pertains also to devices for use in these techniques, wherein the modified compound of the present invention (or its salts or esters) is bonded covalently or non-covalently via effector moiety $X^8$ to the respective devices such as a chromatography stationary phase support material. When using the compounds of the present invention in FACS analysis, it is appropriate to use the compound of the invention in the form of a modified compound, wherein the effector moiety $X^8$ is or contains a fluorescence label.

6. EXAMPLES

6.1. General Information

Chemicals: All reagents and solvents were obtained from commercial suppliers and used without further purification.

Chromatography: Analytical HPLC-ESI-MS was performed on a Hewlett-Packard Series HP 1100 equipped with a Finnigan LCQ mass spectrometer using a YMC-Hydrosphere C18 column (12 nm pore size, 3 μm particle size, 125 mm×2.1 mm) or YMC-Octyl C8 column (20 nm pore size, 5 μm particle size, 250 mm×2.1 mm) and $H_2O$ (0.1% v/v formic acid)/MeCN (0.1% v/v formic acid) as eluents. Semi-preparative HPLC was performed using a Beckmann instrument (system gold, solvent delivery module 126, UV detector 166), an YMC ODS-A column (20×250 mm, 5 μm), flow rate: 8 mL/min, linear gradients of $H_2O$ (0.1% v/v TFA) and MeCN (0.1% v/v TFA).

NMR: $^1$H-NMR and $^{13}$C NMR spectra were recorded at 295 K on a 500 MHz Bruker DMX, 360 MHz Bruker AV or a 250 MHz Bruker AV spectrometer (Bruker, Karlsruhe, Germany). Chemical shifts (δ) are given in parts per million (ppm). The following solvent peaks were used as internal standards: DMSO-$d_5$: 2.50 ppm ($^1$H-NMR) and 39.52 ppm ($^{13}$C-NMR); CHCl$_3$: 7.26 ppm ($^1$H-NMR) and 77.16 ppm ($^{13}$C-NMR). [Gottlieb, H. E.; Kotlyar, V.; Nudelman, A. NMR Chemical Shifts of Common Laboratory Solvents as Trace Impurities. *J. Org. Chem.* 1997, 62, 7512-7515.]

6.2. Example 1: Synthesis of Peptide Compounds

Cyclic peptides were prepared according to the standard Fmoc-Solid Phase Peptide Synthesis (Fmoc-SPPS) using a tritylchloride polystyrene (TCP) resin followed by cyclization in solution. N-Methylation was performed on a resin according to the previously reported method[1] with one exception: N-Nosyl protection was performed in dichloromethane (DCM) instead of N-methylpyrrolidine (NMP).

Following acid labile groups were used for protection of side-chains of amino acids: Pbf for Arginine; tBu for Threonine, Aspartic acid, and Tyrosine; Boc for Lysine and Tryptophan. They were removed using a mixture of trifluoroacetic acid (TFA)/DCM/triisopropylsilane (TIPS)/water (80:10:5:5) for 1.5 h at r.t. Dde protection of side-chain of Lysine was used in the case of large synthesis of cyclic peptide 18 and its functionalized derivatives 23 and 24. The selective deprotection of Dde was performed using 2 vol.-% solution of hydrazine hydrate in dimethylformamide (DMF) for 30 min at r.t. without any effect on Pbf or tBu protective groups.

The synthesis of 24 was performed using HPLC purified 18-$^{Lys}$NH—C(O)CH$_2$CH$_2$CH$_2$CH$_2$CH$_2$NH$_2$ conjugate (1 equiv.; prepared by usual peptide coupling of Dde deprotected 18 with Fmoc-6-aminohexanoic acid followed by deprotection with TFA/DCM/TIPS/water (80:10:5:5) for 1.5 h), Cyanine-5.5 NHS ester (1.1 equiv.), DIPEA (10 equiv.) in DMF for 1 h (HPLC-MS monitoring) followed by evaporation, deprotection with TFA/DCM/TIPS/water (80:10:5:5) for 1.5 h and purification with semi-preparative HPLC.

6.3. Example 2: Integrin Binding Assay

The activity and selectivity of integrin ligands were determined by a solid-phase binding assay according to the previously reported protocols using coated extracellular matrix proteins and soluble integrins: Fibronectin (Fn) for α5β1, latent activating protein (LAP) for αvβ6 and αvβ8, Vitronectin (Vn) for αvβ3 and αvβ5, Fibrinogen (Fbg) for αIIbβ3.

The following compounds were used as internal standards: Cilengitide, c(-RGDf(NMe)V-) (SEQ ID: NO 62) (αvβ3—0.54 nM, α5β1—8 nM),[3] linear peptide RTDLD-SLRT[4] (SEQ ID: NO 63) (αvβ6—33 nM; αvβ8—100 nM) and tirofiban[5] (αIIbβ3—1.2 nM).

The results obtained in the integrin binding assay are summarized in Table 1 below.

TABLE 1

Structure optimization of cyclic peptides.

| Compound | SEQ ID NO: | Amino acid sequence | αvβ6, IC$_{50}$ [nM] | αvβ3, IC$_{50}$ [nM] | Ratio | m/z[a] | $t_R$[b] mi |
|---|---|---|---|---|---|---|---|
| 1* | 64 | A R G D L A A L p P | 8.3 | 76.7 | 1:9.2 | 962.7 | 5.14 |
| 2* | 65 | A R G D A A A L p P | 320 | — | — | 920.6 | 5.91[c] |
| 3* | 66 | A R G D L A A A p P | 15.4 | — | — | 920.6 | 5.55[c] |
| 4 | 67 | A R G D L A L p P | 3.0 | 106 | 1:35 | 891.6 | 6.74[c] |
| 5* | 68 | A R G D L L p P | 292 | — | — | 820.6 | 6.41[c] |
| 6* | 69 | A R G D L p P | 417 | — | — | 707.5 | 5.64[c] |
| 7* | 70 | A R G D L d L p P | 148 | >1000 | — | 935.7 | 4.81 |
| 8* | 71 | A R G D L D L p P | 14.7 | 2.4 | 6.1:1 | 935.7 | 5.00 |
| 9* | 72 | A R G D F A L p P | 63.4 | 65.2 | 1:1 | 925.5 | 5.03 |
| 10 | 73 | A R G D L A F p P | 0.67 | 104 | 1:155 | 925.7 | 5.06 |
| 11 | 74 | A R G D L A K p P | 1.51 | 302 | 1:200 | 906.6 | 3.00[d] |
| 12 | 75 | F R G D L A L p P | 1.25 | >1000 | 1:>1000 | 967.6 | 5.77 |
| 13 | 76 | A R G D L A L p Sar | 8.1 | 87.7 | 1:11 | 865.6 | 4.70[d] |
| 14* | 77 | A R G D L A L Sar P | 24.2 | 85.1 | 1:3.5 | 865.6 | 4.62[d] |
| 15 | 78 | A R G D L A L p (NMe)K | 4.3 | 415 | 1:97 | 936.6 | 4.54[d] |
| 16* | 79 | A R G D L A L (NMe)k P | 11.4 | 50.4 | 1:4.4 | 936.6 | 4.02[d] |
| 17 | 80 | A R G D L A F p (NMe)K | 0.70 | 143 | 1:204 | 970.5 | 3.71[d] |
| 18 | 81 | F R G D L A F p (NMe)K | 0.26 | 632 | 1:2431 | 1046.5 | 4.53[d] |
| 19 | 82 | F R G D L A Y p (NMe)K | 0.39 | 685 | 1:1756 | 1062.5 | 3.77[d] |
| 20 | 83 | F R G D L A W p (NMe)K | 0.12 | 204 | 1:1700 | 1085.5 | 4.40[d] |

TABLE 1-continued

Structure optimization of cyclic peptides.

| Com pound | SEQ ID NO: | Amino acid sequence | αvβ6, IC$_{50}$ [nM] | αvβ3, IC$_{50}$ [nM] | Ratio | m/z[a] | t$_R$[b] mi |
|---|---|---|---|---|---|---|---|
| 21 | 84 | Y R G D L A F p (NMe)K | 0.40 | 432 | 1:1080 | 1062.5 | 3.95[d] |
| 22 | 85 | W R G D L A F p (NMe)K | 0.52 | 645 | 1:1240 | 1085.5 | 4.43[d] |
| 23 | 86 | F R G D L A F p (NMe)K[f] | 0.30 | 640 | 1:2133 | 1088.5 | 5.69 |

[a]Found ESI-MS. [M + H]+,
[b]Retention time, analytical HPLC (5-90%, 15 min),
[c]Retention time, analytical HPLC (5-50%, 15 min),
[d]Retention time, analytical HPLC (0-70%, 10 min),
[e]Retention time, analytical HPLC (5-95%, 10 min),
[f]Lys(Ac),
*Comparative compound.

A complete profile of selected cyclic peptides is provided in Table 2.

TABLE 2

| Cpd. | SEQ ID NO: | Amino acid sequence | αvβ6, IC$_{50}$ [nM] | αvβ3, IC$_{50}$ [nM] | α5β1, IC$_{50}$ [nM] | αvβ8, IC$_{50}$ [nM] | αIIbβ3, IC$_{50}$ [nM] | αvβ5, IC$_{50}$ [nM] |
|---|---|---|---|---|---|---|---|---|
| 1 | 64 | ARGDLAALpP | 8.3 | 76.7 1:9.2 | 454 1:55 | 115 1:14 | >1000 | >1000 |
| 4 | 67 | ARGDLALpP | 3.0 | 106 1:35 | 266 1:89 | 42.9 1:14 | >1000 | >1000 |
| 12 | 75 | FRGDLALpP | 1.25 | >1000 1:>1000 | 254 1:203 | 127 1:102 | >1000 | >1000 |
| 10 | 73 | ARGDLAFpP | 0.67 | 104 1:155 | 38.4 1:57 | 10.4 1:16 | >1000 | >1000 |
| 11 | 74 | ARGDLAKpP | 1.51 | 302 1:200 | 831 1:550 | 49.3 1:33 | >1000 | >1000 |
| 18 | 81 | FRGDLAFp(NMe)K | 0.26 | 632 1:2431 | 72.9 1:280 | 23.6 1:91 | >1000 | >1000 |
| 23 | 86 | FRGDLAFp(NMe)K[a] | 0.30 | 640 1:2133 | 74.0 1:247 | 21.1 1:70 | >1000 | >1000 |

[a]Lys(Ac).

6.4. Example 3: Bioimaging of Cancer Cells

Methods and Materials:

Cell Lines and Culture Conditions

The human oral squamous cell carcinoma (OSCC) cell line HN were purchased from the German Collection of Microorganisms and Cell Cultures, Braunschweig, Germany (DSMZ no. ACC 417). HN cells derived from a cervical lymph node metastasis of a highly aggressive and invasive OSCC of the soft palate.[9] As control cells, we used the human ovarian cancer cell line OVMZ6 with low integrin αvβ6 and high integrin αvβ3 expression.[10] All cells were cultivated in Dulbecco's Modified Eagle's Medium (DMEM) (Sigma-Aldrich, St. Louis, Mo., USA), supplemented with 10% (v/v) fetal calf serum (FCS) (Gibco, LifeTechnologies™, Carlsbad, Calif., USA).

Immunocytochemical Detection of Cellular Integrin αvβ6

HN and OVMZ6 cells were grown on fibronectin-coated microchamber slides (Nunc® Lab-Tek® Chamber Slide™ system, Sigma-Aldrich), fixed in 2% (w/v) paraformaldehyde (PFA) for 15 min at room temperature (RT), once washed in PBS and then blocked for 1 h at r.t. in phosphate-buffered saline (PBS), 2% (w/v) bovine serum albumin (BSA). Monoclonal antibodies directed to integrin αvβ6 (1.6 µg/mL) were incubated on the cells in PBS, 1% (w/v) BSA, for 2 h at r.t., followed by the addition a secondary Alexa-488-labeled goat-anti-mouse IgG (0.6 g/ml) for 45 min at r.t. Slides were mounted in PBS and fluorescence intensity evaluated by the Zeiss LSM 700 (Zeiss, Jena, Germany). In order to convert fluorescence staining intensity into colors of a glow scale, the look-up table (LUT) "orange-to-white" provided with the LSM scanning software Zen (Zeiss) was applied: low intensity (red), medium intensity (yellow), and high intensity (white).

Cell Binding Experiments of Integrin αvβ6-Targeting 9-Cy5.5 Conjugate

HN and OVMZ6 cells were cultivated for 24 h on fibronectin-coated microchamber slides at a density of 25×10³/well, thereafter fixed in 2% (w/v) PFA for 15 min at r.t. and washed in PBS. The Cy5.5-conjugated compound 18-Cy5.5, dissolved in PBS, 5% (v/v) dimethyl sulfoxide (DMSO), was applied at a final concentration of 10 M for 1 h at r.t., followed by 3 washes in PBS. In order to prove binding specificity of 18-Cy5.5 to integrin αvβ6, its unlabeled analogue 18 was incubated on cells at a 10-fold molar excess for 1 h at r.t. prior to the addition of 18-Cy5.5 (10 M). As control peptide served the non-binding cycl(R$^{beta}$ADfK) labelled via lysine side-chain NH$_2$ group with Cy5.5 fluorescent dye. After the incubation period, cells were washed 6 times in PBS and slides mounted. Fluorescence signal intensity was detected by the microscope Zeiss LSM 700 (Zeiss) as described above.

Results

Figure 1:
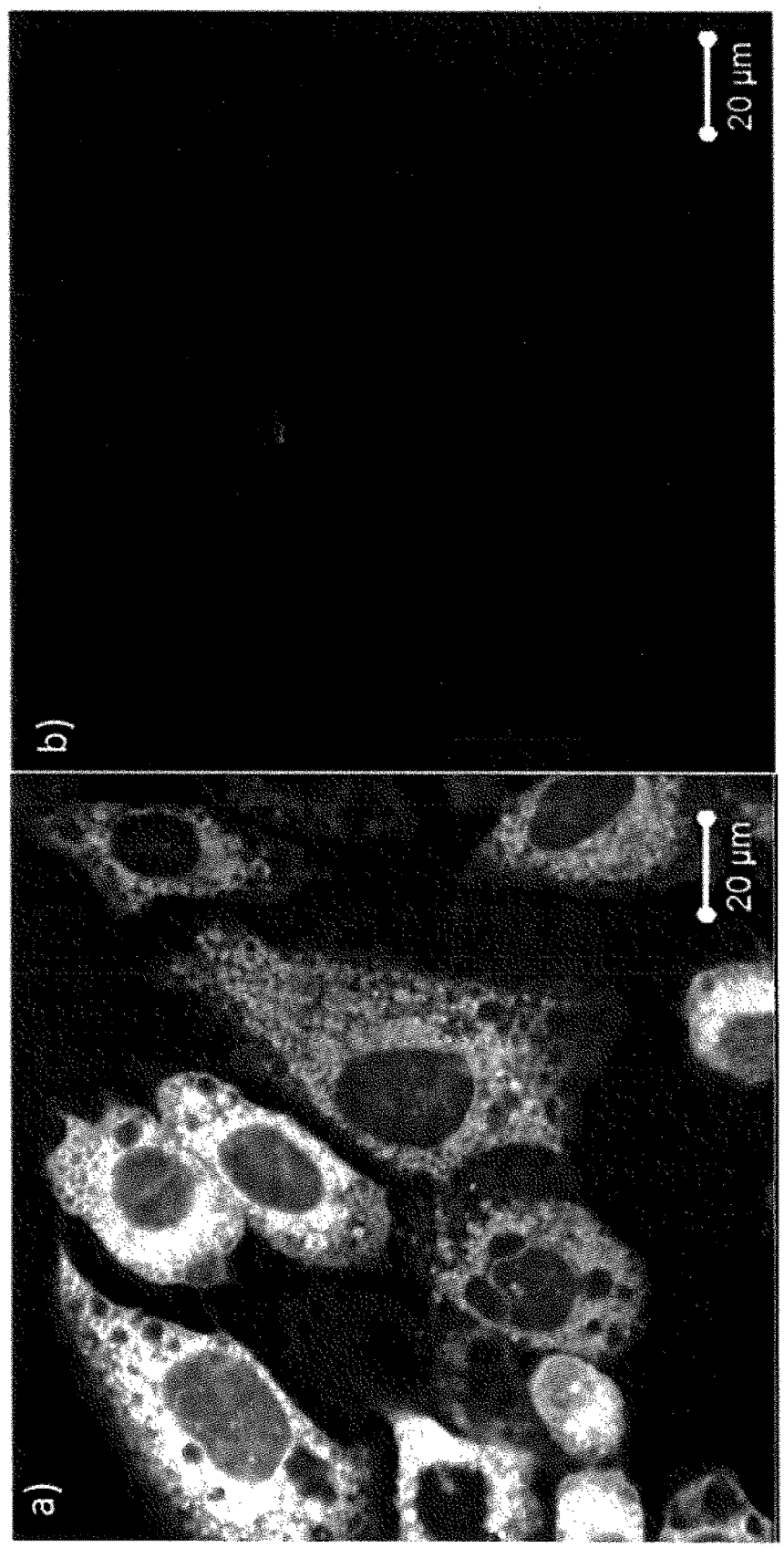
FIG. 1 shows the results of Fluorescence bioimaging with Cy5.5-labelled 10 of the human oral squamous cell carcinoma (OSCC) cell line HN with high level of αvβ6-intergin expression (a) and of human ovarian cancer cell line OVMZ6 with low αvβ6-high αvβ3-integrin expression (b).

Results are shown in FIG. 1. Expression levels of integrin αvβ6 were verified in the OSCC cell line HN[9] by immunocytochemical staining, revealing high expression levels of this integrin, which was located at cellular membranes. As a control cell line, we used human ovarian OVMZ6 cancer cells with low endogenous integrin αvβ6 levels which, however, displayed elevated integrin αvβ3 levels upon stable cell transfection.[10] Incubation of HN cells with 18-Cy5.5 resulted in strong fluorescence signal intensity on cell membranes, whereas the peptide did not bind to OVMZ6 cells. These data indicated that binding intensity of 18-Cy5.5 correlated with integrin αvβ6 expression levels and that 18-Cy5.5 did not recognize cellular integrin αvβ3, proving its strong discrimination capacity between different members of the same integrin subfamily. Specificity of 18-Cy5.5 binding activity on cells was proven by pre-incubating cells with a 10-fold molar excess of the unlabeled analogue of 18-Cy5.5 prior to the addition of 18-Cy5.5. Binding competition experiments by adding first unlabeled analogue of 18-Cy5.5, followed by incubation of cells with its 9-Cy5.5 resulted in a strong reduction in fluorescence signal intensity. This competition capacity proved highly specific integrin αvβ6 targeting of the compound. As a further control, the non-binding cycl($R^{beta}$ADfK)-ahx-Cy5.5 was administered, which did not result in fluorescence signal intensity.

6.5. Example 4: Plasma Stability Assays

Materials

Human plasma was collected from healthy adults with their informed written consent. Water and ACN were obtained from commercial suppliers and used without further purification. Analytical HPLC-ESI-MS was performed on an Agilent Technologies 1200 Series equipped with an Agilent Technologies 6110 Quadrupole LC/MS using a Phenomenex Luna C18 column (5 m, 4.6×150 mm) and H$_2$O (0.1% v/v TFA)/MeCN (0.1% v/v TFA) as eluents.

Methods

A solution of 1 mg/ml of each peptide (control peptide, compound 18 and compound 23) was prepared in water, and 150 µl aliquots were mixed with 150 µl of pre-warmed (37° C.) plasma. At selected time points (0, 30, 60, 120 and 240 min), samples (50 µl) were collected and mixed with 1% TFA in acetonitrile (75 µl) to precipitate plasma proteins which were removed by centrifugation at 13,000 rpm for 10 minutes. The supernatant was analysed by HPLC-ESI-MS using a Phenomenex Luna C18 column (5 µm, 4.6×150 mm) and an elution gradient of 10%-90% solvent B over 20 min (Solvent A: 0.1% TFA in water; solvent B: 0.1% TFA in ACN) at a flow rate of 1 ml/min.

The results are shown in FIGS. 2a to 2c. They are also summarized in Table 3 below.

TABLE 3

ESI-MS characterizations of control peptide, compounds 18 and 23 at different intervals of incubation

| Compound | SEQ ID NO: | Amino acid sequence | m/z[a] | | | | |
|---|---|---|---|---|---|---|---|
| | | | 0 min | 30 min | 60 min | 120 min | 180 min |
| reference | 63 | RTDLDSLRT | 1076.6 | 1076.6[c] 819.5[d] 920.5[d] | 819.5 920.5 | 819.5 | 819.5 |
| 18 | 81 | FRGDLAFp(NMe)K | 1046.6 | 1046.6 | 1046.6 | 1046.6 | 1046.6 |
| 23 | 86 | FRGDLAFp(NMe)K[b] | 1088.6 | 1088.6 | 1088.6 | 1088.6 | 1008.6 |

[a]Found ESI-MS, [M + H]+,
[b]Lys(Ac)
[c]peak at 8.429 min
[d]peak at 8.645 min

The above results reveal that the tested compounds of the invention are stable in human plasma for at least 180 min, which is the longest tested time interval.

The examples of the present invention are provided for illustrative purposes only. They are not meant to limit the present invention. The scope of the present invention is defined by the appended claims, which are to be interpreted in the light of the present description. Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. The contents of all references, issued patents, and published patent applications cited throughout this application are hereby incorporated by reference.

FURTHER REFERENCES

[1] J. Chatterjee, B. Laufer, H. Kessler, Nature protocols 2012, 7, 432-444.
[2] A. Bochen, U. K. Marelli, E. Otto, D. Pallarola, C. Mas-Moruno, F. S. Di Leva, H. Boehm, J. P. Spatz, E. Novellino, H. Kessler, L. Marinelli, Journal of medicinal chemistry 2013, 56, 1509-1519.
[3] C. Mas-Moruno, F. Rechenmacher, H. Kessler, Anti-cancer agents in medicinal chemistry 2010, 10, 753-768.
[4] S. Kraft, B. Diefenbach, R. Mehta, A. Jonczyk, G. A. Luckenbach, S. L. Goodman, The Journal of biological chemistry 1999, 274, 1979-1985.
[5] G. D. Hartman, M. S. Egbertson, W. Halczenko, W. L. Laswell, M. E. Duggan, R. L. Smith, A. M. Naylor, P. D. Manno, R. J. Lynch, G. Zhang, et al., Journal of medicinal chemistry 1992, 35, 4640-4642.
[6] T. F. Havel, Progress in biophysics and molecular biology 1991, 56, 43-78.
[7] G. N. Ramachandran, C. Ramakrishnan, V. Sasisekharan, Journal of molecular biology 1963, 7, 95-99.
[8] A. C. Gibbs, T. C. Bjorndahl, R. S. Hodges, D. S. Wishart, Journal of the American Chemical Society 2002, 124, 1203-1213.

[9] H. Kawamata, K. Nakashiro, D. Uchida, K. Harada, H. Yoshida, M. Sato, *Int J Cancer* 1997, 70, 120-127.
[10] M. A. Muller, J. Opfer, L. Brunie, L. A. Volkhardt, E. K. Sinner, D. Boettiger, A. Bochen, H. Kessler, K. E. Gottschalk, U. Reuning, *Journal of molecular biology* 2013, 425, 2988-3006.
[11] C. Mas-Moruno, F. Rechenmacher, H. Kessler, *Anti-cancer Agents Med. Chem.* 2010, 10, 753-768.
[12] J. C. Phillips, R. Braun, W. Wang, J. Gumbart, E. Tajkhorshid, E. Villa, C. Chipot, R. D. Skeel, L. Kale, K. Schulten, *J. Comput. Chem.* 2005, 26, 1781-1802.
[13] D. A. Case, J. T. Berryman, R. M. Betz, Q. Cai, D. S. Cerutti, T. E. Cheatham III, T. A. Darden, R. E. Duke, H. Gohlke, A. W. Goetz, S. Gusarov, N. Homeyer, P. Janowski, J. Kaus, I. Kolossvary, A. Kovalenko, T. S. Lee, S. LeGrand, T. Luchko, R. Luo, B. Madej, K. M. Merz, Jr., F. Paesani, D. R. Roe, A. Roitberg, C. Sagui, R. Salomon-Ferrer, G. Seabra, C. L. Simmerling, W. L. Smith, J. Swails, R. C. Walker, J. Wang, R. M. Wolf, X. Wu, P. A. Kollman, *AMBER 14 Reference Manual*, 2014, pp. 29-31.
[14] O. Allnér, L. Nilsson, A. Villa, *J. Chem. Theo. Comp.* 2012, 8, 1493-1502.
[15] J. Wang, W. Wang, P. A. Kollman, D. A. Case, *J. Mol. Graph. Model.* 2006, 25, 247-260.
[16] C. I. Bayly, P. Cieplak, W. Cornell, P. A. Kollman, *J. Phys. Chem.* 1993, 97, 10269-10280.
[17] M. J. Frisch, G. W. Trucks, H. B. Schlegel, G. E. Scuseria, M. A. Robb, J. R. Cheeseman, G. Scalmani, V. Barone, B. Mennucci, G. A. Petersson, H. Nakatsuji, M. Caricato, X. Li, H. P. Hratchian, A. F. Izmaylov, J. Bloino, G. Zheng, J. L. Sonnenberg, M. Hada, M. Ehara, K. Toyota, R. Fukuda, J. Hasegawa, M. Ishida, T. Nakajima, Y. Honda, O. Kitao, H. Nakai, T. Vreven, J. A. Montgomery, Jr., J. E. Peralta, F. Ogliaro, M. Bearpark, J. J. Heyd, E. Brothers, K. N. Kudin, V. N. Staroverov, R. Kobayashi, J. Normand, K. Raghavachari, A. Rendell, J. C. Burant, S. S. Iyengar, J. Tomasi, M. Cossi, N. Rega, J. M. Millam, M. Klene, J. E. Knox, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, R. L. Martin, K. Morokuma, V. G. Zakrzewski, G. A. Voth, P. Salvador, J. J. Dannenberg, S. Dapprich, A. D. Daniels, Ö. Farkas, J. B. Foresman, J. V. Ortiz, J. Cioslowski, D. J. Fox, *Gaussian 09, Revision D*.01, Gaussian, Inc., Wallingford Conn., 2009.
[18] W. L. Jorgensen, D. S. Maxwell, J. Tirado-Rives, *J. Am. Chem. Soc.* 1996, 118, 11225-11236.
[19] H. C. Andersen, *J. Comp. Phys.* 1983, 52, 24-34.

The invention claimed is:

1. Compound represented by the following general formula (I):

$$\text{Cyclo-}(Arg\text{-}X^1\text{-}Asp\text{-}X^2\text{-}X^3\text{-}X^4\text{-}X^5\text{-}X^6\text{-}X^7) \qquad (I)$$

wherein the variables groups $X^1$ to $X^7$ have the following meanings $X^1$: Ser, Gly, Thr,
$X^2$: Leu, Ile, Nle, Val, Phe,
$X^3$: Gly, Ala,
$X^4$: Leu, Ile, Nle, Val, Phe, Lys, Tyr, Trp, Arg,
$X^5$: D-Pro, N-Me-D-lipophilic amino acids,
$X^6$: Pro, N-Me-Amino acids, N-Me-Lys, N-Me-Lys(Ac), and
$X^7$: Ala, Leu, Ile, Nle, Val, Phe, Tyr, Trp or wherein the sub-sequence -$X^5$-$X^6$- represents a β-turn mimetic differing from the meanings above,
or pharmaceutically acceptable salts, esters, solvates, polymorphs or modified forms thereof represented by the following general formula (II):

$$(X^0)_{n1}L(X^8)_{n2}$$

wherein $X^0$ represents the compound of the general formula (I) as specified above (excluding one hydrogen atom to allow bonding to the linker), L represents a linker, $X^8$ represents the effector moiety and wherein n1 and n2 are each independently selected from the range of 1 to 5, preferably such that each of n1 and n2 represents 1, wherein n1+n2 represents the number of valencies of the linker and is preferably in the range of from 2 to 6, more preferably 2-5.

2. Compound or pharmaceutically acceptable salts, esters, solvates, polymorphs or modified forms thereof according to claim 1, wherein one or more of the variable groups $X^1$ to $X^7$ have the following specific meanings
   (a) $X^1$: Gly and/or
   (b) $X^2$: Leu, Ile, Nle, Val and/or
   (c) $X^3$: Ala and/or
   (d) $X^4$: Leu, Phe, Lys, Tyr, Trp, Arg and/or
   (e) $X^5$: D-Pro and/or
   (f) $X^6$: Pro, N-Me-Lys, Sar, N-Me-Lys(Ac) and/or
   (g) $X^7$: Ala, Phe, Tyr, Trp,
and the remaining variable groups $X^1$ to $X^7$ have the same meanings as specified in claim 1.

3. Compound or pharmaceutically acceptable salts, esters, solvates, polymorphs or modified forms thereof according to claim 1, wherein the compound is selected from:
   Cyclo-(Ala-Arg-Gly-Asp-Leu-Ala-Leu-D-Pro-Pro),
   Cyclo-(Ala-Arg-Gly-Asp-Leu-Ala-Phe-D-Pro-Pro),
   Cyclo-(Ala-Arg-Gly-Asp-Leu-Ala-Lys-D-Pro-Pro),
   Cyclo-(Phe-Arg-Gly-Asp-Leu-Ala-Leu-D-Pro-Pro),
   Cyclo-(Ala-Arg-Gly-Asp-Leu-Ala-Leu-D-Pro-Sar),
   Cyclo-(Ala-Arg-Gly-Asp-Leu-Ala-Leu-D-Pro-(NMe) Lys),
   Cyclo-(Ala-Arg-Gly-Asp-Leu-Ala-Phe-D-Pro-(NMe) Lys),
   Cyclo-(Phe-Arg-Gly-Asp-Leu-Ala-Phe-D-Pro-(NMe) Lys),
   Cyclo-(Phe-Arg-Gly-Asp-Leu-Ala-Tyr-D-Pro-(NMe) Lys),
   Cyclo-(Phe-Arg-Gly-Asp-Leu-Ala-Trp-D-Pro-(NMe) Lys),
   Cyclo-(Tyr-Arg-Gly-Asp-Leu-Ala-Phe-D-Pro-(NMe) Lys),
   Cyclo-(Trp-Arg-Gly-Asp-Leu-Ala-Phe-D-Pro-(NMe) Lys), and
   Cyclo-(Phe-Arg-Gly-Asp-Leu-Ala-Arg-D-Pro-(NMe) Lys).

4. Modified compound according to claim 1, wherein the linker is selected from the group consisting of ethylene glycol, polyethylene glycol (PEG), propylene glycol, polypropylene glycol (PPG), amino acids, oligopeptides, saccharides and oligosaccharides and combinations thereof.

5. Modified compound according to claim 1, wherein effector moiety $X^8$ is selected from
   (i) a group suitable for labelling the compound of the invention,
   (ii) a group having therapeutic activity or
   (iii) a group suitable for use as an anchor group to make the compound suitable for covalent or non-covalent bonding to other entities.

6. Modified compound according to claim 1, wherein the linker is attached to the compound of general formula (I) via a side chain of one of the A variable groups $X^4$, $X^5$, $X^6$ or $X^7$.

7. Pharmaceutical composition comprising a compound or pharmaceutically acceptable salts, esters, solvates, polymorphs or modified forms thereof according to claim 1 and one or more pharmaceutically acceptable excipients.

8. Pharmaceutical composition comprising a component obtainable by covalently bonding a compound or pharmaceutically acceptable salts, esters, solvates, polymorphs or modified forms thereof according to claim 1 via the effector moiety $X^8$ to a larger entity.

9. A method of treating a medical condition wherein the medical condition is selected from cancer, infections, fibrosis, interstitial lung disease, inflammation, psoriasis and open wounds, comprising administering a compound of claim 1 to a subject.

10. A method of treating a medical condition wherein the medical condition to be treated is cancer selected from oral squamous carcinoma, laryngeal squamous cell carcinoma, oropharyngeal squamous cell carcinoma, nasopharyngeal squamous cell carcinoma, hypopharyngeal squamous cell carcinoma, colon cancer, ovarian carcinoma, non-small cell lung cancer (NSCLC) and gastric cancer, or fibrosis selected from pulmonary fibrosis, cystic fibrosis, idiopatic pulmonary fibrosis, endomyocardial fibrosis, Crohn's disease, and arthofibrosis comprising administering a compound of claim 1 to a subject.

11. A method for performing diagnostic imaging in a subject comprising administration to the subject of a modified compound or pharmaceutically acceptable salts, esters, solvates, polymorphs or modified forms thereof according to claim 1.

12. Pharmaceutical composition according to claim 7, wherein the pharmaceutical composition is formulated to be administered by intravenous administration, intramuscular administration, transdermal administration, transmucosal administration, pulmonary administration, intranasal administration, or oral administration.

13. Process for preparing the compound or pharmaceutically acceptable salts, esters, solvates, polymorphs or modified forms thereof according to claim 1, wherein the process includes a first step of generating a linear precursor molecule using Fmoc-based solid phase peptide synthesis techniques, followed by a second step, wherein the linear precursor molecule is cyclized to yield a compound of general formula (I),
which optionally includes a further step of modifying the compound of general formula (I) to yield a compound of general formula (II).

14. A device comprising a compound or pharmaceutically acceptable salts, esters, solvates, polymorphs or modified forms thereof according to claim 1 covalently or non-covalently bonded via the effector moiety $X^8$ to a larger entity, wherein the larger entity is a diagnostic device, an analytical device or a device for purifying or separating chemical or biological substances.

15. Modified compound according to claim 5, wherein moiety $X^8$ is a group suitable for fluorescence labelling.

16. The method of claim 11, wherein the imaging method is selected from fluorescence labelling, positron emission tomography (PET), single-photon emission computed tomography (SPECT), optical imaging and magnetic resonance imaging (MRI).

17. A method for performing diagnostic imaging in a subject comprising administration to the subject of a composition according to claim 7.

18. A modified compound according to claim 5, wherein the labeling group is for use in fluorescence labeling, positron emission tomography (PET), single-photon emission computed tomography (SPECT), optical imaging or magnetic resonance imaging (MRI).

19. A modified compound according to claim 6, wherein the linker is attached to the compound of general formula (I) via a side chain of the variable group $X^6$.

* * * * *

SEQUENCE LISTING

```
<160> NUMBER OF SEQ ID NOS: 87

<210> SEQ ID NO 1
<211> LENGTH: 7
<212> TYPE: PRT
<213> ORGANISM: Unknown
<220> FEATURE:
<223> OTHER INFORMATION: Foot-and-mouth disease virus
<220> FEATURE:
<221> NAME/KEY: MISC_FEATURE
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (5)..(6)
<223> OTHER INFORMATION: Xaa can be any naturally occurring amino acid

<400> SEQUENCE: 1

Arg Xaa Asp Leu Xaa Xaa Leu
1               5

<210> SEQ ID NO 2
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (5)..(5)
<223> OTHER INFORMATION: Xaa is D-Asp
<220> FEATURE:
<221> NAME/KEY: MOD_RES
<222> LOCATION: (9)..(10)
<223> OTHER INFORMATION: Abu

<400> SEQUENCE: 2

Arg Thr Asp Leu Xaa Ala Leu Arg Xaa Xaa
1               5                   10

<210> SEQ ID NO 3
<211> LENGTH: 9
```

-continued

```
<212> TYPE: PRT
<213> ORGANISM: Artificial Sequence
<220> FEATURE:
<223> OTHER INFORMATION: Synthetic Polypeptide

<400> SEQUENCE: 3

Arg Thr Asp Leu Asp Ser Leu Arg Thr
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Ser, Gly or Thr
<220> FEATURE:
<221> NAME/KEY: MISC_FEATURE
<222> LOCATION: (4)..(4)
<223> OTHER INFORMATION: Xaa is Leu, Ile, Nle, Val or Phe
<220> FEATURE:
<221> NAME/KEY: MISC_FEATURE
<222> LOCATION: (5)..(5)
<223> OTHER INFORMATION: Xaa is Gly or Ala
<220> FEATURE:
<221> NAME/KEY: MISC_FEATURE
<222> LOCATION: (6)..(6)
<223> OTHER INFORMATION: Xaa is Leu, Ile, Nle, Val, Phe, Lys, Tyr, Trp
      or Arg
<220> FEATURE:
<221> NAME/KEY: MISC_FEATURE
<222> LOCATION: (7)..(7)
<223> OTHER INFORMATION: Xaa is D-Pro or N-Me-D-lipophilic amino acids;
      N-Me-amino acid refers to a group, wherein the alpha-amino group
      carries a methyl group
<220> FEATURE:
<221> NAME/KEY: MISC_FEATURE
<222> LOCATION: (8)..(8)
<223> OTHER INFORMATION: Xaa is Pro, N-Me-amino acids, N-Me-Lys or
      N-Me-Lys(Ac); N-Me-amino acid refers to a group, wherein the
      alpha-amino group carries a methyl group; Lys(Ac) refers to a
      lysine residue, wherein the omega-amino group carries an acetyl
      group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 4

Arg Xaa Asp Xaa Xaa Xaa Xaa Xaa Xaa
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Gly
<220> FEATURE:
<221> NAME/KEY: MISC_FEATURE
<222> LOCATION: (4)..(4)
<223> OTHER INFORMATION: Xaa is Leu, Ile, Nle, Val or Phe
<220> FEATURE:
<221> NAME/KEY: MISC_FEATURE
<222> LOCATION: (5)..(5)
<223> OTHER INFORMATION: Xaa is Gly or Ala
<220> FEATURE:
<221> NAME/KEY: MISC_FEATURE
```

```
<222> LOCATION: (6)..(6)
<223> OTHER INFORMATION: Xaa is Leu, Ile, Nle, Val, Phe, Lys, Tyr, Trp
      or Arg
<220> FEATURE:
<221> NAME/KEY: MISC_FEATURE
<222> LOCATION: (7)..(7)
<223> OTHER INFORMATION: Xaa is D-Pro or N-Me-D-lipophilic amino acids;
      N-Me-amino acid refers to a group, wherein the alpha-amino group
      carries a methyl group
<220> FEATURE:
<221> NAME/KEY: MISC_FEATURE
<222> LOCATION: (8)..(8)
<223> OTHER INFORMATION: Xaa is Pro, N-Me-amino acids, N-Me-Lys,
      N-Me-Lys(Ac); N-Me-amino acid refers to a group, wherein the
      alpha-amino group carries a methyl group; Lys(Ac) refers to a
      lysine residue, wherein the omega-amino group carries an acetyl
      group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 5

Arg Xaa Asp Xaa Xaa Xaa Xaa Xaa Xaa
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Ser, Gly or Thr
<220> FEATURE:
<221> NAME/KEY: MISC_FEATURE
<222> LOCATION: (4)..(4)
<223> OTHER INFORMATION: Xaa is Leu or Nle
<220> FEATURE:
<221> NAME/KEY: MISC_FEATURE
<222> LOCATION: (5)..(5)
<223> OTHER INFORMATION: Xaa is Gly or Ala
<220> FEATURE:
<221> NAME/KEY: MISC_FEATURE
<222> LOCATION: (6)..(6)
<223> OTHER INFORMATION: Xaa is Leu, Ile, Nle, Val, Phe, Lys, Tyr, Trp
      or Arg
<220> FEATURE:
<221> NAME/KEY: MISC_FEATURE
<222> LOCATION: (7)..(7)
<223> OTHER INFORMATION: Xaa is D-Pro or N-Me-D-lipophilic amino acids;
      N-Me-amino acid refers to a group, wherein the alpha-amino group
      carries a methyl group
<220> FEATURE:
<221> NAME/KEY: MISC_FEATURE
<222> LOCATION: (8)..(8)
<223> OTHER INFORMATION: Xaa is Pro, N-Me-amino acids, N-Me-Lys,
      N-Me-Lys(Ac); N-Me-amino acid refers to a group, wherein the
      alpha-amino group carries a methyl group; Lys(Ac) refers to a
      lysine residue, wherein the omega-amino group carries an acetyl
      group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 6

Arg Xaa Asp Xaa Xaa Xaa Xaa Xaa Xaa
1               5

<210> SEQ ID NO 7
<211> LENGTH: 9
<212> TYPE: PRT
```

```
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Ser, Gly or Thr
<220> FEATURE:
<221> NAME/KEY: MISC_FEATURE
<222> LOCATION: (4)..(4)
<223> OTHER INFORMATION: Xaa is Leu
<220> FEATURE:
<221> NAME/KEY: MISC_FEATURE
<222> LOCATION: (5)..(5)
<223> OTHER INFORMATION: Xaa is Gly or Ala
<220> FEATURE:
<221> NAME/KEY: MISC_FEATURE
<222> LOCATION: (6)..(6)
<223> OTHER INFORMATION: Xaa is Leu, Ile, Nle, Val, Phe, Lys, Tyr, Trp
     or Arg
<220> FEATURE:
<221> NAME/KEY: MISC_FEATURE
<222> LOCATION: (7)..(7)
<223> OTHER INFORMATION: Xaa is D-Pro or N-Me-D-lipophilic amino acids;
     N-Me-amino acid refers to a group, wherein the alpha-amino group
     carries a methyl group
<220> FEATURE:
<221> NAME/KEY: MISC_FEATURE
<222> LOCATION: (8)..(8)
<223> OTHER INFORMATION: Xaa is Pro, N-Me-amino acids, N-Me-Lys,
     N-Me-Lys(Ac); N-Me-amino acid refers to a group, wherein the
     alpha-amino group carries a methyl group; Lys(Ac) refers to a
     lysine residue, wherein the omega-amino group carries an acetyl
     group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 7

Arg Xaa Asp Xaa Xaa Xaa Xaa Xaa Xaa
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Ser, Gly or Thr
<220> FEATURE:
<221> NAME/KEY: MISC_FEATURE
<222> LOCATION: (4)..(4)
<223> OTHER INFORMATION: Xaa is Leu, Ile, Nle, Val or Phe
<220> FEATURE:
<221> NAME/KEY: MISC_FEATURE
<222> LOCATION: (5)..(5)
<223> OTHER INFORMATION: Xaa is Gly
<220> FEATURE:
<221> NAME/KEY: MISC_FEATURE
<222> LOCATION: (6)..(6)
<223> OTHER INFORMATION: Xaa is Leu, Ile, Nle, Val, Phe, Lys, Tyr, Trp
     or Arg
<220> FEATURE:
<221> NAME/KEY: MISC_FEATURE
<222> LOCATION: (7)..(7)
<223> OTHER INFORMATION: Xaa is D-Pro or N-Me-D-lipophilic amino acids;
     N-Me-amino acid refers to a group, wherein the alpha-amino group
     carries a methyl group
<220> FEATURE:
<221> NAME/KEY: MISC_FEATURE
<222> LOCATION: (8)..(8)
<223> OTHER INFORMATION: Xaa is Pro, N-Me-amino acids, N-Me-Lys,
     N-Me-Lys(Ac); N-Me-amino acid refers to a group, wherein the
```

```
      alpha-amino group carries a methyl group; Lys(Ac) refers to a
      lysine residue, wherein the omega-amino group carries an acetyl
      group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 8

Arg Xaa Asp Xaa Xaa Xaa Xaa Xaa Xaa
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Ser, Gly or Thr
<220> FEATURE:
<221> NAME/KEY: MISC_FEATURE
<222> LOCATION: (4)..(4)
<223> OTHER INFORMATION: Xaa is Leu, Ile, Nle, Val or Phe
<220> FEATURE:
<221> NAME/KEY: MISC_FEATURE
<222> LOCATION: (5)..(5)
<223> OTHER INFORMATION: Xaa is Gly or Ala
<220> FEATURE:
<221> NAME/KEY: MISC_FEATURE
<222> LOCATION: (6)..(6)
<223> OTHER INFORMATION: Xaa is Leu, Phe, Lys, Tyr, Trp or Arg
<220> FEATURE:
<221> NAME/KEY: MISC_FEATURE
<222> LOCATION: (7)..(7)
<223> OTHER INFORMATION: Xaa is D-Pro or N-Me-D-lipophilic amino acids;
      N-Me-amino acid refers to a group, wherein the alpha-amino group
      carries a methyl group
<220> FEATURE:
<221> NAME/KEY: MISC_FEATURE
<222> LOCATION: (8)..(8)
<223> OTHER INFORMATION: Xaa is Pro, N-Me-amino acids, N-Me-Lys,
      N-Me-Lys(Ac); N-Me-amino acid refers to a group, wherein the
      alpha-amino group carries a methyl group; Lys(Ac) refers to a
      lysine residue, wherein the omega-amino group carries an acetyl
      group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 9

Arg Xaa Asp Xaa Xaa Xaa Xaa Xaa Xaa
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Ser, Gly or Thr
<220> FEATURE:
<221> NAME/KEY: MISC_FEATURE
<222> LOCATION: (4)..(4)
<223> OTHER INFORMATION: Xaa is Leu, Ile, Nle, Val or Phe
<220> FEATURE:
<221> NAME/KEY: MISC_FEATURE
<222> LOCATION: (5)..(5)
<223> OTHER INFORMATION: Xaa is Gly or Ala
```

```
<220> FEATURE:
<221> NAME/KEY: MISC_FEATURE
<222> LOCATION: (6)..(6)
<223> OTHER INFORMATION: Xaa is Leu, Ile, Nle, Val, Phe, Lys, Tyr, Trp
      or Arg
<220> FEATURE:
<221> NAME/KEY: MISC_FEATURE
<222> LOCATION: (7)..(7)
<223> OTHER INFORMATION: Xaa is D-Pro
<220> FEATURE:
<221> NAME/KEY: MISC_FEATURE
<222> LOCATION: (8)..(8)
<223> OTHER INFORMATION: Xaa is Pro, N-Me-amino acids, N-Me-Lys,
      N-Me-Lys(Ac); N-Me-amino acid refers to a group, wherein the
      alpha-amino group carries a methyl group; Lys(Ac) refers to a
      lysine residue, wherein the omega-amino group carries an acetyl
      group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 10

Arg Xaa Asp Xaa Xaa Xaa Xaa Xaa Xaa
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Ser, Gly or Thr
<220> FEATURE:
<221> NAME/KEY: MISC_FEATURE
<222> LOCATION: (4)..(4)
<223> OTHER INFORMATION: Xaa is Leu, Ile, Nle, Val or Phe
<220> FEATURE:
<221> NAME/KEY: MISC_FEATURE
<222> LOCATION: (5)..(5)
<223> OTHER INFORMATION: Xaa is Gly or Ala
<220> FEATURE:
<221> NAME/KEY: MISC_FEATURE
<222> LOCATION: (6)..(6)
<223> OTHER INFORMATION: Xaa is Leu, Ile, Nle, Val, Phe, Lys, Tyr, Trp
      or Arg
<220> FEATURE:
<221> NAME/KEY: MISC_FEATURE
<222> LOCATION: (7)..(7)
<223> OTHER INFORMATION: Xaa is D-Pro or N-Me-D-lipophilic amino acids;
      N-Me-amino acid refers to a group, wherein the alpha-amino group
      carries a methyl group
<220> FEATURE:
<221> NAME/KEY: MISC_FEATURE
<222> LOCATION: (8)..(8)
<223> OTHER INFORMATION: Xaa is Pro, Sar, N-Me-Lys, N-Me-Lys(Ac);
      N-Me-amino acid refers to a group, wherein the alpha-amino group
      carries a methyl group; Lys(Ac) refers to a lysine residue,
      wherein the omega-amino group carries an acetyl group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 11

Arg Xaa Asp Xaa Xaa Xaa Xaa Xaa Xaa
1               5

<210> SEQ ID NO 12
<211> LENGTH: 9
<212> TYPE: PRT
<213> ORGANISM: Artificial Sequence
```

```
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Ser, Gly or Thr
<220> FEATURE:
<221> NAME/KEY: MISC_FEATURE
<222> LOCATION: (4)..(4)
<223> OTHER INFORMATION: Xaa is Leu, Ile, Nle, Val or Phe
<220> FEATURE:
<221> NAME/KEY: MISC_FEATURE
<222> LOCATION: (5)..(5)
<223> OTHER INFORMATION: Xaa is Gly or Ala
<220> FEATURE:
<221> NAME/KEY: MISC_FEATURE
<222> LOCATION: (6)..(6)
<223> OTHER INFORMATION: Xaa is Leu, Ile, Nle, Val, Phe, Lys, Tyr, Trp
      or Arg
<220> FEATURE:
<221> NAME/KEY: MISC_FEATURE
<222> LOCATION: (7)..(7)
<223> OTHER INFORMATION: Xaa is D-Pro or N-Me-D-lipophilic amino acids;
      N-Me-amino acid refers to a group, wherein the alpha-amino group
      carries a methyl group
<220> FEATURE:
<221> NAME/KEY: MISC_FEATURE
<222> LOCATION: (8)..(8)
<223> OTHER INFORMATION: Xaa is Pro, N-Me-amino acids, N-Me-Lys,
      N-Me-Lys(Ac); N-Me-amino acid refers to a group, wherein the
      alpha-amino group carries a methyl group; Lys(Ac) refers to
      a lysine residue, wherein the omega-amino group carries an acetyl
      group
<220> FEATURE:
<221> NAME/KEY: MISC_FEATURE
<222> LOCATION: (9)..(9)
<223> OTHER INFORMATION: Xaa is Ala, Phe, Tyr or Trp

<400> SEQUENCE: 12

Arg Xaa Asp Xaa Xaa Xaa Xaa Xaa Xaa
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Gly
<220> FEATURE:
<221> NAME/KEY: MISC_FEATURE
<222> LOCATION: (4)..(4)
<223> OTHER INFORMATION: Xaa is Leu
<220> FEATURE:
<221> NAME/KEY: MISC_FEATURE
<222> LOCATION: (5)..(5)
<223> OTHER INFORMATION: Xaa is Gly or Ala
<220> FEATURE:
<221> NAME/KEY: MISC_FEATURE
<222> LOCATION: (6)..(6)
<223> OTHER INFORMATION: Xaa is Leu, Ile, Nle, Val, Phe, Lys, Tyr, Trp
      or Arg
<220> FEATURE:
<221> NAME/KEY: MISC_FEATURE
<222> LOCATION: (7)..(7)
<223> OTHER INFORMATION: Xaa is D-Pro or N-Me-D-lipophilic amino acids;
      N-Me-amino acid refers to a group, wherein the alpha-amino group
      carries a methyl group
<220> FEATURE:
<221> NAME/KEY: MISC_FEATURE
<222> LOCATION: (8)..(8)
<223> OTHER INFORMATION: Xaa is Pro, N-Me-amino acids, N-Me-Lys,
      N-Me-Lys(Ac); N-Me-amino acid refers to a group, wherein the
      alpha-amino group carries a methyl group; Lys(Ac) refers to a
```

```
        lysine residue, wherein the omega-amino group carries an acetyl
        group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 13

Arg Xaa Asp Xaa Xaa Xaa Xaa Xaa Xaa
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Gly
<220> FEATURE:
<221> NAME/KEY: MISC_FEATURE
<222> LOCATION: (4)..(4)
<223> OTHER INFORMATION: Xaa is Leu
<220> FEATURE:
<221> NAME/KEY: MISC_FEATURE
<222> LOCATION: (5)..(5)
<223> OTHER INFORMATION: Xaa is Ala
<220> FEATURE:
<221> NAME/KEY: MISC_FEATURE
<222> LOCATION: (6)..(6)
<223> OTHER INFORMATION: Xaa is Leu, Ile, Nle, Val, Phe, Lys, Tyr, Trp
      or Arg
<220> FEATURE:
<221> NAME/KEY: MISC_FEATURE
<222> LOCATION: (7)..(7)
<223> OTHER INFORMATION: Xaa is D-Pro or N-Me-D-lipophilic amino acids;
      N-Me-amino acid refers to a group, wherein the alpha-amino group
      carries a methyl group
<220> FEATURE:
<221> NAME/KEY: MISC_FEATURE
<222> LOCATION: (8)..(8)
<223> OTHER INFORMATION: Xaa is Pro, N-Me-amino acids, N-Me-Lys,
      N-Me-Lys(Ac); N-Me-amino acid refers to a group, wherein the
      alpha-amino group carries a methyl group; Lys(Ac) refers to a
      lysine residue, wherein the omega-amino group carries an acetyl
      group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 14

Arg Xaa Asp Xaa Xaa Xaa Xaa Xaa Xaa
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Gly
<220> FEATURE:
<221> NAME/KEY: MISC_FEATURE
<222> LOCATION: (4)..(4)
<223> OTHER INFORMATION: Xaa is Leu
<220> FEATURE:
<221> NAME/KEY: MISC_FEATURE
<222> LOCATION: (5)..(5)
<223> OTHER INFORMATION: Xaa is Ala
```

```
<220> FEATURE:
<221> NAME/KEY: MISC_FEATURE
<222> LOCATION: (6)..(6)
<223> OTHER INFORMATION: Xaa is Leu, Phe, Lys, Tyr, Trp or Arg
<220> FEATURE:
<221> NAME/KEY: MISC_FEATURE
<222> LOCATION: (7)..(7)
<223> OTHER INFORMATION: Xaa is D-Pro or N-Me-D-lipophilic amino acids;
      N-Me-amino acid refers to a group, wherein the alpha-amino group
      carries a methyl group
<220> FEATURE:
<221> NAME/KEY: MISC_FEATURE
<222> LOCATION: (8)..(8)
<223> OTHER INFORMATION: Xaa is Pro, N-Me-amino acids, N-Me-Lys,
      N-Me-Lys(Ac); N-Me-amino acid refers to a group, wherein the
      alpha-amino group carries a methyl group; Lys(Ac) refers to a
      lysine residue, wherein the omega-amino group carries an acetyl
      group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 15

Arg Xaa Asp Xaa Xaa Xaa Xaa Xaa Xaa
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Gly
<220> FEATURE:
<221> NAME/KEY: MISC_FEATURE
<222> LOCATION: (4)..(4)
<223> OTHER INFORMATION: Xaa is Leu
<220> FEATURE:
<221> NAME/KEY: MISC_FEATURE
<222> LOCATION: (5)..(5)
<223> OTHER INFORMATION: Xaa is Ala
<220> FEATURE:
<221> NAME/KEY: MISC_FEATURE
<222> LOCATION: (6)..(6)
<223> OTHER INFORMATION: Xaa is Leu, Phe, Lys, Tyr, Trp or Arg
<220> FEATURE:
<221> NAME/KEY: MISC_FEATURE
<222> LOCATION: (7)..(7)
<223> OTHER INFORMATION: Xaa is D-Pro
<220> FEATURE:
<221> NAME/KEY: MISC_FEATURE
<222> LOCATION: (8)..(8)
<223> OTHER INFORMATION: Xaa is Pro, N-Me-amino acids, N-Me-Lys,
      N-Me-Lys(Ac); N-Me-amino acid refers to a group, wherein the
      alpha-amino group carries a methyl group; Lys(Ac) refers to a
      lysine residue, wherein the omega-amino group carries an acetyl
      group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 16

Arg Xaa Asp Xaa Xaa Xaa Xaa Xaa Xaa
1               5

<210> SEQ ID NO 17
<211> LENGTH: 9
<212> TYPE: PRT
<213> ORGANISM: Artificial Sequence
<220> FEATURE:
```

```
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Gly
<220> FEATURE:
<221> NAME/KEY: MISC_FEATURE
<222> LOCATION: (4)..(4)
<223> OTHER INFORMATION: Xaa is Leu
<220> FEATURE:
<221> NAME/KEY: MISC_FEATURE
<222> LOCATION: (5)..(5)
<223> OTHER INFORMATION: Xaa is Ala
<220> FEATURE:
<221> NAME/KEY: MISC_FEATURE
<222> LOCATION: (6)..(6)
<223> OTHER INFORMATION: Xaa is Leu, Phe, Lys, Tyr, Trp or Arg
<220> FEATURE:
<221> NAME/KEY: MISC_FEATURE
<222> LOCATION: (7)..(7)
<223> OTHER INFORMATION: Xaa is D-Pro
<220> FEATURE:
<221> NAME/KEY: MISC_FEATURE
<222> LOCATION: (8)..(8)
<223> OTHER INFORMATION: Xaa is Pro, Sar, N-Me-Lys, N-Me-Lys(Ac);
     N-Me-amino acid refers to a group, wherein the alpha-amino group
     carries a methyl group; Lys(Ac) refers to a lysine residue,
     wherein the omega-amino group carries an acetyl group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 17

Arg Xaa Asp Xaa Xaa Xaa Xaa Xaa Xaa
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Gly
<220> FEATURE:
<221> NAME/KEY: MISC_FEATURE
<222> LOCATION: (4)..(4)
<223> OTHER INFORMATION: Xaa is Leu
<220> FEATURE:
<221> NAME/KEY: MISC_FEATURE
<222> LOCATION: (5)..(5)
<223> OTHER INFORMATION: Xaa is Ala
<220> FEATURE:
<221> NAME/KEY: MISC_FEATURE
<222> LOCATION: (6)..(6)
<223> OTHER INFORMATION: Xaa is Leu, Phe, Lys, Tyr, Trp or Arg
<220> FEATURE:
<221> NAME/KEY: MISC_FEATURE
<222> LOCATION: (7)..(7)
<223> OTHER INFORMATION: Xaa is D-Pro
<220> FEATURE:
<221> NAME/KEY: MISC_FEATURE
<222> LOCATION: (8)..(8)
<223> OTHER INFORMATION: Xaa is Pro, Sar, N-Me-Lys, N-Me-Lys(Ac);
     N-Me-amino acid refers to a group, wherein the alpha-amino group
     carries a methyl group; Lys(Ac) refers to a lysine residue,
     wherein the omega-amino group carries an acetyl group
<220> FEATURE:
<221> NAME/KEY: MISC_FEATURE
<222> LOCATION: (9)..(9)
<223> OTHER INFORMATION: Xaa is Ala, Phe, Tyr or Trp

<400> SEQUENCE: 18
```

-continued

Arg Xaa Asp Xaa Xaa Xaa Xaa Xaa Xaa
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Gly
<220> FEATURE:
<221> NAME/KEY: MISC_FEATURE
<222> LOCATION: (4)..(4)
<223> OTHER INFORMATION: Xaa is Leu
<220> FEATURE:
<221> NAME/KEY: MISC_FEATURE
<222> LOCATION: (5)..(5)
<223> OTHER INFORMATION: Xaa is Ala
<220> FEATURE:
<221> NAME/KEY: MISC_FEATURE
<222> LOCATION: (6)..(6)
<223> OTHER INFORMATION: Xaa is Leu, Ile, Nle, Val, Phe, Lys, Tyr, Trp
      or Arg
<220> FEATURE:
<221> NAME/KEY: MISC_FEATURE
<222> LOCATION: (7)..(7)
<223> OTHER INFORMATION: Xaa is D-Pro
<220> FEATURE:
<221> NAME/KEY: MISC_FEATURE
<222> LOCATION: (8)..(8)
<223> OTHER INFORMATION: Xaa is Pro, N-Me-amino acids, N-Me-Lys,
      N-Me-Lys(Ac); N-Me-amino acid refers to a group, wherein the
      alpha-amino group carries a methyl group; Lys(Ac) refers to a
      lysine residue, wherein the omega-amino group carries an acetyl
      group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 19

Arg Xaa Asp Xaa Xaa Xaa Xaa Xaa Xaa
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Gly
<220> FEATURE:
<221> NAME/KEY: MISC_FEATURE
<222> LOCATION: (4)..(4)
<223> OTHER INFORMATION: Xaa is Leu
<220> FEATURE:
<221> NAME/KEY: MISC_FEATURE
<222> LOCATION: (5)..(5)
<223> OTHER INFORMATION: Xaa is Ala
<220> FEATURE:
<221> NAME/KEY: MISC_FEATURE
<222> LOCATION: (6)..(6)
<223> OTHER INFORMATION: Xaa is Leu, Ile, Nle, Val, Phe, Lys, Tyr, Trp
      or Arg
<220> FEATURE:
<221> NAME/KEY: MISC_FEATURE
<222> LOCATION: (7)..(7)
<223> OTHER INFORMATION: Xaa is D-Pro
<220> FEATURE:
<221> NAME/KEY: MISC_FEATURE
<222> LOCATION: (8)..(8)
<223> OTHER INFORMATION: Xaa is Pro, Sar, N-Me-Lys, N-Me-Lys(Ac);
     N-Me-amino acid refers to a group, wherein the alpha-amino group
     carries a methyl group; Lys(Ac) refers to a lysine residue,
     wherein the omega-amino group carries an acetyl group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 20

Arg Xaa Asp Xaa Xaa Xaa Xaa Xaa Xaa
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Gly
<220> FEATURE:
<221> NAME/KEY: MISC_FEATURE
<222> LOCATION: (4)..(4)
<223> OTHER INFORMATION: Xaa is Leu, Nle
<220> FEATURE:
<221> NAME/KEY: MISC_FEATURE
<222> LOCATION: (5)..(5)
<223> OTHER INFORMATION: Xaa is Gly or Ala
<220> FEATURE:
<221> NAME/KEY: MISC_FEATURE
<222> LOCATION: (6)..(6)
<223> OTHER INFORMATION: Xaa is Leu, Ile, Nle, Val, Phe, Lys, Tyr, Trp
     or Arg
<220> FEATURE:
<221> NAME/KEY: MISC_FEATURE
<222> LOCATION: (7)..(7)
<223> OTHER INFORMATION: Xaa is D-Pro or N-Me-D-lipophilic amino acids;
     N-Me-amino acid refers to a group, wherein the alpha-amino group
     carries a methyl group
<220> FEATURE:
<221> NAME/KEY: MISC_FEATURE
<222> LOCATION: (8)..(8)
<223> OTHER INFORMATION: Xaa is Pro, N-Me-amino acids, N-Me-Lys,
     N-Me-Lys(Ac); N-Me-amino acid refers to a group, wherein the
     alpha-amino group carries a methyl group; Lys(Ac) refers to a
     lysine residue, wherein the omega-amino group carries an acetyl
     group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 21

Arg Xaa Asp Xaa Xaa Xaa Xaa Xaa Xaa
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Gly
<220> FEATURE:
<221> NAME/KEY: MISC_FEATURE
<222> LOCATION: (4)..(4)
<223> OTHER INFORMATION: Xaa is Leu, Nle
<220> FEATURE:

```
<221> NAME/KEY: MISC_FEATURE
<222> LOCATION: (5)..(5)
<223> OTHER INFORMATION: Xaa is Ala
<220> FEATURE:
<221> NAME/KEY: MISC_FEATURE
<222> LOCATION: (6)..(6)
<223> OTHER INFORMATION: Xaa is Leu, Ile, Nle, Val, Phe, Lys, Tyr, Trp
      or Arg
<220> FEATURE:
<221> NAME/KEY: MISC_FEATURE
<222> LOCATION: (7)..(7)
<223> OTHER INFORMATION: Xaa is D-Pro or N-Me-D-lipophilic amino acids;
      N-Me-amino acid refers to a group, wherein the alpha-amino group
      carries a methyl group
<220> FEATURE:
<221> NAME/KEY: MISC_FEATURE
<222> LOCATION: (8)..(8)
<223> OTHER INFORMATION: Xaa is Pro, N-Me-amino acids, N-Me-Lys,
      N-Me-Lys(Ac); N-Me-amino acid refers to a group, wherein the
      alpha-amino group carries a methyl group; Lys(Ac) refers to a
      lysine residue, wherein the omega-amino group carries an acetyl
      group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 22

Arg Xaa Asp Xaa Xaa Xaa Xaa Xaa Xaa
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Gly
<220> FEATURE:
<221> NAME/KEY: MISC_FEATURE
<222> LOCATION: (4)..(4)
<223> OTHER INFORMATION: Xaa is Leu, Nle
<220> FEATURE:
<221> NAME/KEY: MISC_FEATURE
<222> LOCATION: (5)..(5)
<223> OTHER INFORMATION: Xaa is Ala
<220> FEATURE:
<221> NAME/KEY: MISC_FEATURE
<222> LOCATION: (6)..(6)
<223> OTHER INFORMATION: Xaa is Leu, Phe, Lys, Tyr, Trp or Arg
<220> FEATURE:
<221> NAME/KEY: MISC_FEATURE
<222> LOCATION: (7)..(7)
<223> OTHER INFORMATION: Xaa is D-Pro or N-Me-D-lipophilic amino acids;
      N-Me-amino acid refers to a group, wherein the alpha-amino group
      carries a methyl group
<220> FEATURE:
<221> NAME/KEY: MISC_FEATURE
<222> LOCATION: (8)..(8)
<223> OTHER INFORMATION: Xaa is Pro, N-Me-amino acids, N-Me-Lys,
      N-Me-Lys(Ac); N-Me-amino acid refers to a group, wherein the
      alpha-amino group carries a methyl group; Lys(Ac) refers to a
      lysine residue, wherein the omega-amino group carries an acetyl
      group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 23

Arg Xaa Asp Xaa Xaa Xaa Xaa Xaa Xaa
1               5
```

```
<210> SEQ ID NO 24
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Gly
<220> FEATURE:
<221> NAME/KEY: MISC_FEATURE
<222> LOCATION: (4)..(4)
<223> OTHER INFORMATION: Xaa is Leu, Nle
<220> FEATURE:
<221> NAME/KEY: MISC_FEATURE
<222> LOCATION: (5)..(5)
<223> OTHER INFORMATION: Xaa is Ala
<220> FEATURE:
<221> NAME/KEY: MISC_FEATURE
<222> LOCATION: (6)..(6)
<223> OTHER INFORMATION: Xaa is Leu, Phe, Lys, Tyr, Trp or Arg
<220> FEATURE:
<221> NAME/KEY: MISC_FEATURE
<222> LOCATION: (7)..(7)
<223> OTHER INFORMATION: Xaa is D-Pro
<220> FEATURE:
<221> NAME/KEY: MISC_FEATURE
<222> LOCATION: (8)..(8)
<223> OTHER INFORMATION: Xaa is Pro, N-Me-amino acids, N-Me-Lys,
      N-Me-Lys(Ac); N-Me-amino acid refers to a group, wherein the
      alpha-amino group carries a methyl group; Lys(Ac) refers to a
      lysine residue, wherein the omega-amino group carries an acetyl
      group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 24

Arg Xaa Asp Xaa Xaa Xaa Xaa Xaa Xaa
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Gly
<220> FEATURE:
<221> NAME/KEY: MISC_FEATURE
<222> LOCATION: (4)..(4)
<223> OTHER INFORMATION: Xaa is Leu, Nle
<220> FEATURE:
<221> NAME/KEY: MISC_FEATURE
<222> LOCATION: (5)..(5)
<223> OTHER INFORMATION: Xaa is Ala
<220> FEATURE:
<221> NAME/KEY: MISC_FEATURE
<222> LOCATION: (6)..(6)
<223> OTHER INFORMATION: Xaa is Leu, Phe, Lys, Tyr, Trp or Arg
<220> FEATURE:
<221> NAME/KEY: MISC_FEATURE
<222> LOCATION: (7)..(7)
<223> OTHER INFORMATION: Xaa is D-Pro
<220> FEATURE:
<221> NAME/KEY: MISC_FEATURE
<222> LOCATION: (8)..(8)
<223> OTHER INFORMATION: Xaa is Pro, Sar, N-Me-Lys, N-Me-Lys(Ac);
      N-Me-amino acid refers to a group, wherein the alpha-amino group
      carries a methyl group; Lys(Ac) refers to a lysine residue,
      wherein the omega-amino group carries an acetyl group
```

```
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 25

Arg Xaa Asp Xaa Xaa Xaa Xaa Xaa Xaa
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Gly
<220> FEATURE:
<221> NAME/KEY: MISC_FEATURE
<222> LOCATION: (4)..(4)
<223> OTHER INFORMATION: Xaa is Leu, Nle
<220> FEATURE:
<221> NAME/KEY: MISC_FEATURE
<222> LOCATION: (5)..(5)
<223> OTHER INFORMATION: Xaa is Ala
<220> FEATURE:
<221> NAME/KEY: MISC_FEATURE
<222> LOCATION: (6)..(6)
<223> OTHER INFORMATION: Xaa is Leu, Phe, Lys, Tyr, Trp or Arg
<220> FEATURE:
<221> NAME/KEY: MISC_FEATURE
<222> LOCATION: (7)..(7)
<223> OTHER INFORMATION: Xaa is D-Pro
<220> FEATURE:
<221> NAME/KEY: MISC_FEATURE
<222> LOCATION: (8)..(8)
<223> OTHER INFORMATION: Xaa is Pro, Sar, N-Me-Lys, N-Me-Lys(Ac);
      N-Me-amino acid refers to a group, wherein the alpha-amino group
      carries a methyl group; Lys(Ac) refers to a lysine residue,
      wherein the omega-amino group carries an acetyl group
<220> FEATURE:
<221> NAME/KEY: MISC_FEATURE
<222> LOCATION: (9)..(9)
<223> OTHER INFORMATION: Xaa is Ala, Phe, Tyr or Trp

<400> SEQUENCE: 26

Arg Xaa Asp Xaa Xaa Xaa Xaa Xaa Xaa
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Gly
<220> FEATURE:
<221> NAME/KEY: MISC_FEATURE
<222> LOCATION: (4)..(4)
<223> OTHER INFORMATION: Xaa is Leu, Nle
<220> FEATURE:
<221> NAME/KEY: MISC_FEATURE
<222> LOCATION: (5)..(5)
<223> OTHER INFORMATION: Xaa is Gly or Ala
<220> FEATURE:
<221> NAME/KEY: MISC_FEATURE
<222> LOCATION: (6)..(6)
<223> OTHER INFORMATION: Xaa is Leu, Ile, Nle, Val, Phe, Lys, Tyr, Trp
      or Arg
<220> FEATURE:
```

```
<221> NAME/KEY: MISC_FEATURE
<222> LOCATION: (7)..(7)
<223> OTHER INFORMATION: Xaa is D-Pro
<220> FEATURE:
<221> NAME/KEY: MISC_FEATURE
<222> LOCATION: (8)..(8)
<223> OTHER INFORMATION: Xaa is Pro, N-Me-amino acids, N-Me-Lys,
      N-Me-Lys(Ac); N-Me-amino acid refers to a group, wherein the
      alpha-amino group carries a methyl group; Lys(Ac) refers to a
      lysine residue, wherein the omega-amino group carries an acetyl
      group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 27

Arg Xaa Asp Xaa Xaa Xaa Xaa Xaa Xaa
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Gly
<220> FEATURE:
<221> NAME/KEY: MISC_FEATURE
<222> LOCATION: (4)..(4)
<223> OTHER INFORMATION: Xaa is Leu, Nle
<220> FEATURE:
<221> NAME/KEY: MISC_FEATURE
<222> LOCATION: (5)..(5)
<223> OTHER INFORMATION: Xaa is Gly or Ala
<220> FEATURE:
<221> NAME/KEY: MISC_FEATURE
<222> LOCATION: (6)..(6)
<223> OTHER INFORMATION: Xaa is Leu, Ile, Nle, Val, Phe, Lys, Tyr, Trp
      or Arg
<220> FEATURE:
<221> NAME/KEY: MISC_FEATURE
<222> LOCATION: (7)..(7)
<223> OTHER INFORMATION: Xaa is D-Pro
<220> FEATURE:
<221> NAME/KEY: MISC_FEATURE
<222> LOCATION: (8)..(8)
<223> OTHER INFORMATION: Xaa is Pro, Sar, N-Me-Lys, N-Me-Lys(Ac);
      N-Me-amino acid refers to a group, wherein the alpha-amino group
      carries a methyl group; Lys(Ac) refers to a lysine residue,
      wherein the omega-amino group carries an acetyl group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 28

Arg Xaa Asp Xaa Xaa Xaa Xaa Xaa Xaa
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Gly
<220> FEATURE:
<221> NAME/KEY: MISC_FEATURE
```

-continued

```
<222> LOCATION: (4)..(4)
<223> OTHER INFORMATION: Xaa is Leu, Nle
<220> FEATURE:
<221> NAME/KEY: MISC_FEATURE
<222> LOCATION: (5)..(5)
<223> OTHER INFORMATION: Xaa is Ala
<220> FEATURE:
<221> NAME/KEY: MISC_FEATURE
<222> LOCATION: (6)..(6)
<223> OTHER INFORMATION: Xaa is Leu, Ile, Nle, Val, Phe, Lys, Tyr, Trp
      or Arg
<220> FEATURE:
<221> NAME/KEY: MISC_FEATURE
<222> LOCATION: (7)..(7)
<223> OTHER INFORMATION: Xaa is D-Pro
<220> FEATURE:
<221> NAME/KEY: MISC_FEATURE
<222> LOCATION: (8)..(8)
<223> OTHER INFORMATION: Xaa is Pro, Sar, N-Me-Lys, N-Me-Lys(Ac);
      N-Me-amino acid refers to a group, wherein the alpha-amino group
      carries a methyl group; Lys(Ac) refers to a lysine residue,
      wherein the omega-amino group carries an acetyl group
<220> FEATURE:
<221> NAME/KEY: MISC_FEATURE
<222> LOCATION: (9)..(9)
<223> OTHER INFORMATION: Xaa is Ala, Phe, Tyr or Trp

<400> SEQUENCE: 29

Arg Xaa Asp Xaa Xaa Xaa Xaa Xaa Xaa
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Gly
<220> FEATURE:
<221> NAME/KEY: MISC_FEATURE
<222> LOCATION: (4)..(4)
<223> OTHER INFORMATION: Xaa is Leu, Nle
<220> FEATURE:
<221> NAME/KEY: MISC_FEATURE
<222> LOCATION: (5)..(5)
<223> OTHER INFORMATION: Xaa is Ala
<220> FEATURE:
<221> NAME/KEY: MISC_FEATURE
<222> LOCATION: (6)..(6)
<223> OTHER INFORMATION: Xaa is Leu, Ile, Nle, Val, Phe, Lys, Tyr, Trp
      or Arg
<220> FEATURE:
<221> NAME/KEY: MISC_FEATURE
<222> LOCATION: (7)..(7)
<223> OTHER INFORMATION: Xaa is D-Pro
<220> FEATURE:
<221> NAME/KEY: MISC_FEATURE
<222> LOCATION: (8)..(8)
<223> OTHER INFORMATION: Xaa is Pro, Sar, N-Me-Lys, N-Me-Lys(Ac);
      N-Me-amino acid refers to a group, wherein the alpha-amino group
      carries a methyl group; Lys(Ac) refers to a lysine residue,
      wherein the omega-amino group carries an acetyl group
<220> FEATURE:
<221> NAME/KEY: MISC_FEATURE
<222> LOCATION: (9)..(9)
<223> OTHER INFORMATION: Xaa is Ala, Phe, Tyr or Trp

<400> SEQUENCE: 30

Arg Xaa Asp Xaa Xaa Xaa Xaa Xaa Xaa
1               5

<210> SEQ ID NO 31
```

```
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Ser, Gly or Thr
<220> FEATURE:
<221> NAME/KEY: MISC_FEATURE
<222> LOCATION: (4)..(4)
<223> OTHER INFORMATION: Xaa is Leu, Nle
<220> FEATURE:
<221> NAME/KEY: MISC_FEATURE
<222> LOCATION: (5)..(5)
<223> OTHER INFORMATION: Xaa is Ala
<220> FEATURE:
<221> NAME/KEY: MISC_FEATURE
<222> LOCATION: (6)..(6)
<223> OTHER INFORMATION: Xaa is Leu, Phe, Lys, Tyr, Trp or Arg
<220> FEATURE:
<221> NAME/KEY: MISC_FEATURE
<222> LOCATION: (7)..(7)
<223> OTHER INFORMATION: Xaa is D-Pro or N-Me-D-lipophilic amino acids;
    N-Me-amino acid refers to a group, wherein the alpha-amino group
    carries a methyl group
<220> FEATURE:
<221> NAME/KEY: MISC_FEATURE
<222> LOCATION: (8)..(8)
<223> OTHER INFORMATION: Xaa is Pro, N-Me-amino acids, N-Me-Lys,
    N-Me-Lys(Ac); N-Me-amino acid refers to a group, wherein the
    alpha-amino group carries a methyl group; Lys(Ac) refers to a
    lysine residue, wherein the omega-amino group carries an acetyl
    group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 31

Arg Xaa Asp Xaa Xaa Xaa Xaa Xaa Xaa
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Ser, Gly or Thr
<220> FEATURE:
<221> NAME/KEY: MISC_FEATURE
<222> LOCATION: (4)..(4)
<223> OTHER INFORMATION: Xaa is Leu, Nle
<220> FEATURE:
<221> NAME/KEY: MISC_FEATURE
<222> LOCATION: (5)..(5)
<223> OTHER INFORMATION: Xaa is Ala
<220> FEATURE:
<221> NAME/KEY: MISC_FEATURE
<222> LOCATION: (6)..(6)
<223> OTHER INFORMATION: Xaa is Leu, Phe, Lys, Tyr, Trp or Arg
<220> FEATURE:
<221> NAME/KEY: MISC_FEATURE
<222> LOCATION: (7)..(7)
<223> OTHER INFORMATION: Xaa is D-Pro or N-Me-D-lipophilic amino acids;
    N-Me-amino acid refers to a group, wherein the alpha-amino group
    carries a methyl group
<220> FEATURE:
<221> NAME/KEY: MISC_FEATURE
<222> LOCATION: (8)..(8)
<223> OTHER INFORMATION: Xaa is Pro, N-Me-amino acids, N-Me-Lys,
    N-Me-Lys(Ac); N-Me-amino acid refers to a group, wherein the
```

```
       alpha-amino group carries a methyl group; Lys(Ac) refers to a
       lysine residue, wherein the omega-amino group carries an acetyl
       group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 32

Arg Xaa Asp Xaa Xaa Xaa Xaa Xaa Xaa
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Ser, Gly or Thr
<220> FEATURE:
<221> NAME/KEY: MISC_FEATURE
<222> LOCATION: (4)..(4)
<223> OTHER INFORMATION: Xaa is Leu, Nle
<220> FEATURE:
<221> NAME/KEY: MISC_FEATURE
<222> LOCATION: (5)..(5)
<223> OTHER INFORMATION: Xaa is Ala
<220> FEATURE:
<221> NAME/KEY: MISC_FEATURE
<222> LOCATION: (6)..(6)
<223> OTHER INFORMATION: Xaa is Leu, Phe, Lys, Tyr, Trp or Arg
<220> FEATURE:
<221> NAME/KEY: MISC_FEATURE
<222> LOCATION: (7)..(7)
<223> OTHER INFORMATION: Xaa is D-Pro
<220> FEATURE:
<221> NAME/KEY: MISC_FEATURE
<222> LOCATION: (8)..(8)
<223> OTHER INFORMATION: Xaa is Pro, N-Me-amino acids, N-Me-Lys,
       N-Me-Lys(Ac); N-Me-amino acid refers to a group, wherein the
       alpha-amino group carries a methyl group; Lys(Ac) refers to a
       lysine residue, wherein the omega-amino group carries an acetyl
       group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 33

Arg Xaa Asp Xaa Xaa Xaa Xaa Xaa Xaa
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Ser, Gly or Thr
<220> FEATURE:
<221> NAME/KEY: MISC_FEATURE
<222> LOCATION: (4)..(4)
<223> OTHER INFORMATION: Xaa is Leu, Nle
<220> FEATURE:
<221> NAME/KEY: MISC_FEATURE
<222> LOCATION: (5)..(5)
<223> OTHER INFORMATION: Xaa is Ala
<220> FEATURE:
<221> NAME/KEY: MISC_FEATURE
```

```
<222> LOCATION: (6)..(6)
<223> OTHER INFORMATION: Xaa is Leu, Phe, Lys, Tyr, Trp or Arg
<220> FEATURE:
<221> NAME/KEY: MISC_FEATURE
<222> LOCATION: (7)..(7)
<223> OTHER INFORMATION: Xaa is D-Pro
<220> FEATURE:
<221> NAME/KEY: MISC_FEATURE
<222> LOCATION: (8)..(8)
<223> OTHER INFORMATION: Xaa is Pro, Sar, N-Me-Lys, N-Me-Lys(Ac);
      N-Me-amino acid refers to a group, wherein the alpha-amino group
      carries a methyl group; Lys(Ac) refers to a lysine residue,
      wherein the omega-amino group carries an acetyl group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 34

Arg Xaa Asp Xaa Xaa Xaa Xaa Xaa Xaa
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Ser, Gly or Thr
<220> FEATURE:
<221> NAME/KEY: MISC_FEATURE
<222> LOCATION: (4)..(4)
<223> OTHER INFORMATION: Xaa is Leu, Nle
<220> FEATURE:
<221> NAME/KEY: MISC_FEATURE
<222> LOCATION: (5)..(5)
<223> OTHER INFORMATION: Xaa is Ala
<220> FEATURE:
<221> NAME/KEY: MISC_FEATURE
<222> LOCATION: (6)..(6)
<223> OTHER INFORMATION: Xaa is Leu, Phe, Lys, Tyr, Trp or Arg
<220> FEATURE:
<221> NAME/KEY: MISC_FEATURE
<222> LOCATION: (7)..(7)
<223> OTHER INFORMATION: Xaa is D-Pro
<220> FEATURE:
<221> NAME/KEY: MISC_FEATURE
<222> LOCATION: (8)..(8)
<223> OTHER INFORMATION: Xaa is Pro, Sar, N-Me-Lys, N-Me-Lys(Ac);
      N-Me-amino acid refers to a group, wherein the alpha-amino group
      carries a methyl group; Lys(Ac) refers to a lysine residue,
      wherein the omega-amino group carries an acetyl group
<220> FEATURE:
<221> NAME/KEY: MISC_FEATURE
<222> LOCATION: (9)..(9)
<223> OTHER INFORMATION: Xaa is Ala, Phe, Tyr or Trp

<400> SEQUENCE: 35

Arg Xaa Asp Xaa Xaa Xaa Xaa Xaa Xaa
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Ser, Gly or Thr
<220> FEATURE:
```

-continued

```
<221> NAME/KEY: MISC_FEATURE
<222> LOCATION: (4)..(4)
<223> OTHER INFORMATION: Xaa is Leu, Nle
<220> FEATURE:
<221> NAME/KEY: MISC_FEATURE
<222> LOCATION: (5)..(5)
<223> OTHER INFORMATION: Xaa is Ala
<220> FEATURE:
<221> NAME/KEY: MISC_FEATURE
<222> LOCATION: (6)..(6)
<223> OTHER INFORMATION: Xaa is Leu, Ile, Nle, Val, Phe, Lys, Tyr, Trp
      or Arg
<220> FEATURE:
<221> NAME/KEY: MISC_FEATURE
<222> LOCATION: (7)..(7)
<223> OTHER INFORMATION: Xaa is D-Pro
<220> FEATURE:
<221> NAME/KEY: MISC_FEATURE
<222> LOCATION: (8)..(8)
<223> OTHER INFORMATION: Xaa is Pro, N-Me-amino acids, N-Me-Lys,
      N-Me-Lys(Ac); N-Me-amino acid refers to a group, wherein the
      alpha-amino group carries a methyl group; Lys(Ac) refers to a
      lysine residue, wherein the omega-amino group carries an acetyl
      group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 36

Arg Xaa Asp Xaa Xaa Xaa Xaa Xaa Xaa
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Ser, Gly or Thr
<220> FEATURE:
<221> NAME/KEY: MISC_FEATURE
<222> LOCATION: (4)..(4)
<223> OTHER INFORMATION: Xaa is Leu, Nle
<220> FEATURE:
<221> NAME/KEY: MISC_FEATURE
<222> LOCATION: (5)..(5)
<223> OTHER INFORMATION: Xaa is Ala
<220> FEATURE:
<221> NAME/KEY: MISC_FEATURE
<222> LOCATION: (6)..(6)
<223> OTHER INFORMATION: Xaa is Leu, Ile, Nle, Val, Phe, Lys, Tyr, Trp
      or Arg
<220> FEATURE:
<221> NAME/KEY: MISC_FEATURE
<222> LOCATION: (7)..(7)
<223> OTHER INFORMATION: Xaa is D-Pro
<220> FEATURE:
<221> NAME/KEY: MISC_FEATURE
<222> LOCATION: (8)..(8)
<223> OTHER INFORMATION: Xaa is Pro, Sar, N-Me-Lys, N-Me-Lys(Ac);
      N-Me-amino acid refers to a group, wherein the alpha-amino group
      carries a methyl group; Lys(Ac) refers to a lysine residue,
      wherein the omega-amino group carries an acetyl group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 37

Arg Xaa Asp Xaa Xaa Xaa Xaa Xaa Xaa
1               5
```

```
<210> SEQ ID NO 38
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Ser, Gly or Thr
<220> FEATURE:
<221> NAME/KEY: MISC_FEATURE
<222> LOCATION: (4)..(4)
<223> OTHER INFORMATION: Xaa is Leu, Nle
<220> FEATURE:
<221> NAME/KEY: MISC_FEATURE
<222> LOCATION: (5)..(5)
<223> OTHER INFORMATION: Xaa is Ala
<220> FEATURE:
<221> NAME/KEY: MISC_FEATURE
<222> LOCATION: (6)..(6)
<223> OTHER INFORMATION: Xaa is Leu, Ile, Nle, Val, Phe, Lys, Tyr, Trp
      or Arg
<220> FEATURE:
<221> NAME/KEY: MISC_FEATURE
<222> LOCATION: (7)..(7)
<223> OTHER INFORMATION: Xaa is D-Pro
<220> FEATURE:
<221> NAME/KEY: MISC_FEATURE
<222> LOCATION: (8)..(8)
<223> OTHER INFORMATION: Xaa is Pro, Sar, N-Me-Lys, N-Me-Lys(Ac);
      N-Me-amino acid refers to a group, wherein the alpha-amino group
      carries a methyl group; Lys(Ac) refers to a lysine residue,
      wherein the omega-amino group carries an acetyl group
<220> FEATURE:
<221> NAME/KEY: MISC_FEATURE
<222> LOCATION: (9)..(9)
<223> OTHER INFORMATION: Xaa is Ala, Phe, Tyr or Trp

<400> SEQUENCE: 38

Arg Xaa Asp Xaa Xaa Xaa Xaa Xaa Xaa
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Ser, Gly or Thr
<220> FEATURE:
<221> NAME/KEY: MISC_FEATURE
<222> LOCATION: (4)..(4)
<223> OTHER INFORMATION: Xaa is Leu
<220> FEATURE:
<221> NAME/KEY: MISC_FEATURE
<222> LOCATION: (5)..(5)
<223> OTHER INFORMATION: Xaa is Ala
<220> FEATURE:
<221> NAME/KEY: MISC_FEATURE
<222> LOCATION: (6)..(6)
<223> OTHER INFORMATION: Xaa is Leu, Phe, Lys, Tyr, Trp or Arg
<220> FEATURE:
<221> NAME/KEY: MISC_FEATURE
<222> LOCATION: (7)..(7)
<223> OTHER INFORMATION: Xaa is D-Pro or N-Me-D-lipophilic amino acids;
      N-Me-amino acid refers to a group, wherein the alpha-amino group
      carries a methyl group
<220> FEATURE:
<221> NAME/KEY: MISC_FEATURE
<222> LOCATION: (8)..(8)
<223> OTHER INFORMATION: Xaa is Pro, N-Me-amino acids, N-Me-Lys,
      N-Me-Lys(Ac); N-Me-amino acid refers to a group, wherein the
```

```
      alpha-amino group carries a methyl group; Lys(Ac) refers to a
      lysine residue, wherein the omega-amino group carries an acetyl
      group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 39

Arg Xaa Asp Xaa Xaa Xaa Xaa Xaa Xaa
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Ser, Gly or Thr
<220> FEATURE:
<221> NAME/KEY: MISC_FEATURE
<222> LOCATION: (4)..(4)
<223> OTHER INFORMATION: Xaa is Leu
<220> FEATURE:
<221> NAME/KEY: MISC_FEATURE
<222> LOCATION: (5)..(5)
<223> OTHER INFORMATION: Xaa is Ala
<220> FEATURE:
<221> NAME/KEY: MISC_FEATURE
<222> LOCATION: (6)..(6)
<223> OTHER INFORMATION: Xaa is Leu, Phe, Lys, Tyr, Trp or Arg
<220> FEATURE:
<221> NAME/KEY: MISC_FEATURE
<222> LOCATION: (7)..(7)
<223> OTHER INFORMATION: Xaa is D-Pro or N-Me-D-lipophilic amino acids;
      N-Me-amino acid refers to a group, wherein the alpha-amino group
      carries a methyl group
<220> FEATURE:
<221> NAME/KEY: MISC_FEATURE
<222> LOCATION: (8)..(8)
<223> OTHER INFORMATION: Xaa is Pro, N-Me-amino acids, N-Me-Lys,
      N-Me-Lys(Ac); N-Me-amino acid refers to a group, wherein the
      alpha-amino group carries a methyl group; Lys(Ac) refers to a
      lysine residue, wherein the omega-amino group carries an acetyl
      group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 40

Arg Xaa Asp Xaa Xaa Xaa Xaa Xaa Xaa
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Ser, Gly or Thr
<220> FEATURE:
<221> NAME/KEY: MISC_FEATURE
<222> LOCATION: (4)..(4)
<223> OTHER INFORMATION: Xaa is Leu
<220> FEATURE:
<221> NAME/KEY: MISC_FEATURE
<222> LOCATION: (5)..(5)
<223> OTHER INFORMATION: Xaa is Ala
```

```
<220> FEATURE:
<221> NAME/KEY: MISC_FEATURE
<222> LOCATION: (6)..(6)
<223> OTHER INFORMATION: Xaa is Leu, Phe, Lys, Tyr, Trp or Arg
<220> FEATURE:
<221> NAME/KEY: MISC_FEATURE
<222> LOCATION: (7)..(7)
<223> OTHER INFORMATION: Xaa is D-Pro
<220> FEATURE:
<221> NAME/KEY: MISC_FEATURE
<222> LOCATION: (8)..(8)
<223> OTHER INFORMATION: Xaa is Pro, N-Me-amino acids, N-Me-Lys,
      N-Me-Lys(Ac); N-Me-amino acid refers to a group, wherein the
      alpha-amino group carries a methyl group; Lys(Ac) refers to a
      lysine residue, wherein the omega-amino group carries an acetyl
      group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 41

Arg Xaa Asp Xaa Xaa Xaa Xaa Xaa Xaa
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Ser, Gly or Thr
<220> FEATURE:
<221> NAME/KEY: MISC_FEATURE
<222> LOCATION: (4)..(4)
<223> OTHER INFORMATION: Xaa is Leu
<220> FEATURE:
<221> NAME/KEY: MISC_FEATURE
<222> LOCATION: (5)..(5)
<223> OTHER INFORMATION: Xaa is Ala
<220> FEATURE:
<221> NAME/KEY: MISC_FEATURE
<222> LOCATION: (6)..(6)
<223> OTHER INFORMATION: Xaa is Leu, Phe, Lys, Tyr, Trp or Arg
<220> FEATURE:
<221> NAME/KEY: MISC_FEATURE
<222> LOCATION: (7)..(7)
<223> OTHER INFORMATION: Xaa is D-Pro
<220> FEATURE:
<221> NAME/KEY: MISC_FEATURE
<222> LOCATION: (8)..(8)
<223> OTHER INFORMATION: Xaa is Pro, Sar, N-Me-Lys, N-Me-Lys(Ac);
      N-Me-amino acid refers to a group, wherein the alpha-amino group
      carries a methyl group; Lys(Ac) refers to a lysine residue,
      wherein the omega-amino group carries an acetyl group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 42

Arg Xaa Asp Xaa Xaa Xaa Xaa Xaa Xaa
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
```

```
<222> LOCATION: (2)..(2)
<223> OTHER INFORMATION: Xaa is Ser, Gly or Thr
<220> FEATURE:
<221> NAME/KEY: MISC_FEATURE
<222> LOCATION: (4)..(4)
<223> OTHER INFORMATION: Xaa is Leu
<220> FEATURE:
<221> NAME/KEY: MISC_FEATURE
<222> LOCATION: (5)..(5)
<223> OTHER INFORMATION: Xaa is Ala
<220> FEATURE:
<221> NAME/KEY: MISC_FEATURE
<222> LOCATION: (6)..(6)
<223> OTHER INFORMATION: Xaa is Leu, Phe, Lys, Tyr, Trp or Arg
<220> FEATURE:
<221> NAME/KEY: MISC_FEATURE
<222> LOCATION: (7)..(7)
<223> OTHER INFORMATION: Xaa is D-Pro
<220> FEATURE:
<221> NAME/KEY: MISC_FEATURE
<222> LOCATION: (8)..(8)
<223> OTHER INFORMATION: Xaa is Pro, Sar, N-Me-Lys, N-Me-Lys(Ac);
      N-Me-amino acid refers to a group, wherein the alpha-amino group
      carries a methyl group; Lys(Ac) refers to a lysine residue,
      wherein the omega-amino group carries an acetyl group
<220> FEATURE:
<221> NAME/KEY: MISC_FEATURE
<222> LOCATION: (9)..(9)
<223> OTHER INFORMATION: Xaa is Ala, Phe, Tyr or Trp

<400> SEQUENCE: 43

Arg Xaa Asp Xaa Xaa Xaa Xaa Xaa Xaa
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Ser, Gly or Thr
<220> FEATURE:
<221> NAME/KEY: MISC_FEATURE
<222> LOCATION: (4)..(4)
<223> OTHER INFORMATION: Xaa is Leu
<220> FEATURE:
<221> NAME/KEY: MISC_FEATURE
<222> LOCATION: (5)..(5)
<223> OTHER INFORMATION: Xaa is Ala
<220> FEATURE:
<221> NAME/KEY: MISC_FEATURE
<222> LOCATION: (6)..(6)
<223> OTHER INFORMATION: Xaa is Leu, Ile, Nle, Val, Phe, Lys, Tyr, Trp
      or Arg
<220> FEATURE:
<221> NAME/KEY: MISC_FEATURE
<222> LOCATION: (7)..(7)
<223> OTHER INFORMATION: Xaa is D-Pro
<220> FEATURE:
<221> NAME/KEY: MISC_FEATURE
<222> LOCATION: (8)..(8)
<223> OTHER INFORMATION: Xaa is Pro, N-Me-amino acids, N-Me-Lys,
      N-Me-Lys(Ac); N-Me-amino acid refers to a group, wherein the
      alpha-amino group carries a methyl group; Lys(Ac) refers to a
      lysine residue, wherein the omega-amino group carries an acetyl
      group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 44

Arg Xaa Asp Xaa Xaa Xaa Xaa Xaa Xaa
```

```
<210> SEQ ID NO 45
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Ser, Gly or Thr
<220> FEATURE:
<221> NAME/KEY: MISC_FEATURE
<222> LOCATION: (4)..(4)
<223> OTHER INFORMATION: Xaa is Leu
<220> FEATURE:
<221> NAME/KEY: MISC_FEATURE
<222> LOCATION: (5)..(5)
<223> OTHER INFORMATION: Xaa is Ala
<220> FEATURE:
<221> NAME/KEY: MISC_FEATURE
<222> LOCATION: (6)..(6)
<223> OTHER INFORMATION: Xaa is Leu, Ile, Nle, Val, Phe, Lys, Tyr, Trp
      or Arg
<220> FEATURE:
<221> NAME/KEY: MISC_FEATURE
<222> LOCATION: (7)..(7)
<223> OTHER INFORMATION: Xaa is D-Pro
<220> FEATURE:
<221> NAME/KEY: MISC_FEATURE
<222> LOCATION: (8)..(8)
<223> OTHER INFORMATION: Xaa is Pro, Sar, N-Me-Lys, N-Me-Lys(Ac);
      N-Me-amino acid refers to a group, wherein the alpha-amino group
      carries a methyl group; Lys(Ac) refers to a lysine residue,
      wherein the omega-amino group carries an acetyl group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 45

Arg Xaa Asp Xaa Xaa Xaa Xaa Xaa Xaa
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Ser, Gly or Thr
<220> FEATURE:
<221> NAME/KEY: MISC_FEATURE
<222> LOCATION: (4)..(4)
<223> OTHER INFORMATION: Xaa is Leu
<220> FEATURE:
<221> NAME/KEY: MISC_FEATURE
<222> LOCATION: (5)..(5)
<223> OTHER INFORMATION: Xaa is Ala
<220> FEATURE:
<221> NAME/KEY: MISC_FEATURE
<222> LOCATION: (6)..(6)
<223> OTHER INFORMATION: Xaa is Leu, Ile, Nle, Val, Phe, Lys, Tyr, Trp
      or Arg
<220> FEATURE:
<221> NAME/KEY: MISC_FEATURE
<222> LOCATION: (7)..(7)
<223> OTHER INFORMATION: Xaa is D-Pro
<220> FEATURE:
<221> NAME/KEY: MISC_FEATURE
<222> LOCATION: (8)..(8)
<223> OTHER INFORMATION: Xaa is Pro, Sar, N-Me-Lys, N-Me-Lys(Ac);
```

```
            N-Me-amino acid refers to a group, wherein the alpha-amino group
            carries a methyl group; Lys(Ac) refers to a lysine residue,
            wherein the omega-amino group carries an acetyl group
<220> FEATURE:
<221> NAME/KEY: MISC_FEATURE
<222> LOCATION: (9)..(9)
<223> OTHER INFORMATION: Xaa is Ala, Phe, Tyr or Trp

<400> SEQUENCE: 46

Arg Xaa Asp Xaa Xaa Xaa Xaa Xaa Xaa
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Ser, Gly or Thr
<220> FEATURE:
<221> NAME/KEY: MISC_FEATURE
<222> LOCATION: (4)..(4)
<223> OTHER INFORMATION: Xaa is Leu, Ile, Nle, Val or Phe
<220> FEATURE:
<221> NAME/KEY: MISC_FEATURE
<222> LOCATION: (5)..(5)
<223> OTHER INFORMATION: Xaa is Gly
<220> FEATURE:
<221> NAME/KEY: MISC_FEATURE
<222> LOCATION: (6)..(6)
<223> OTHER INFORMATION: Xaa is Leu, Phe, Lys, Tyr, Trp or Arg
<220> FEATURE:
<221> NAME/KEY: MISC_FEATURE
<222> LOCATION: (7)..(7)
<223> OTHER INFORMATION: Xaa is D-Pro or N-Me-D-lipophilic amino acids;
            N-Me-amino acid refers to a group, wherein the alpha-amino group
            carries a methyl group
<220> FEATURE:
<221> NAME/KEY: MISC_FEATURE
<222> LOCATION: (8)..(8)
<223> OTHER INFORMATION: Xaa is Pro, N-Me-amino acids, N-Me-Lys,
            N-Me-Lys(Ac); N-Me-amino acid refers to a group, wherein the
            alpha-amino group carries a methyl group; Lys(Ac) refers to a
            lysine residue, wherein the omega-amino group carries an acetyl
            group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 47

Arg Xaa Asp Xaa Xaa Xaa Xaa Xaa Xaa
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Ser, Gly or Thr
<220> FEATURE:
<221> NAME/KEY: MISC_FEATURE
<222> LOCATION: (4)..(4)
<223> OTHER INFORMATION: Xaa is Leu, Ile, Nle, Val or Phe
<220> FEATURE:
<221> NAME/KEY: MISC_FEATURE
<222> LOCATION: (5)..(5)
<223> OTHER INFORMATION: Xaa is Gly
```

```
<220> FEATURE:
<221> NAME/KEY: MISC_FEATURE
<222> LOCATION: (6)..(6)
<223> OTHER INFORMATION: Xaa is Leu, Phe, Lys, Tyr, Trp or Arg
<220> FEATURE:
<221> NAME/KEY: MISC_FEATURE
<222> LOCATION: (7)..(7)
<223> OTHER INFORMATION: Xaa is D-Pro
<220> FEATURE:
<221> NAME/KEY: MISC_FEATURE
<222> LOCATION: (8)..(8)
<223> OTHER INFORMATION: Xaa is Pro, N-Me-amino acids, N-Me-Lys,
      N-Me-Lys(Ac); N-Me-amino acid refers to a group, wherein the
      alpha-amino group carries a methyl group; Lys(Ac) refers to a
      lysine residue, wherein the omega-amino group carries an acetyl
      group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 48

Arg Xaa Asp Xaa Xaa Xaa Xaa Xaa Xaa
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Ser, Gly or Thr
<220> FEATURE:
<221> NAME/KEY: MISC_FEATURE
<222> LOCATION: (4)..(4)
<223> OTHER INFORMATION: Xaa is Leu, Ile, Nle, Val or Phe
<220> FEATURE:
<221> NAME/KEY: MISC_FEATURE
<222> LOCATION: (5)..(5)
<223> OTHER INFORMATION: Xaa is Gly
<220> FEATURE:
<221> NAME/KEY: MISC_FEATURE
<222> LOCATION: (6)..(6)
<223> OTHER INFORMATION: Xaa is Leu, Phe, Lys, Tyr, Trp or Arg
<220> FEATURE:
<221> NAME/KEY: MISC_FEATURE
<222> LOCATION: (7)..(7)
<223> OTHER INFORMATION: Xaa is D-Pro
<220> FEATURE:
<221> NAME/KEY: MISC_FEATURE
<222> LOCATION: (8)..(8)
<223> OTHER INFORMATION: Xaa is Pro, Sar, N-Me-Lys, N-Me-Lys(Ac);
      N-Me-amino acid refers to a group, wherein the alpha-amino group
      carries a methyl group; Lys(Ac) refers to a lysine residue,
      wherein the omega-amino group carries an acetyl group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 49

Arg Xaa Asp Xaa Xaa Xaa Xaa Xaa Xaa
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
```

```
<222> LOCATION: (2)..(2)
<223> OTHER INFORMATION: Xaa is Ser, Gly or Thr
<220> FEATURE:
<221> NAME/KEY: MISC_FEATURE
<222> LOCATION: (4)..(4)
<223> OTHER INFORMATION: Xaa is Leu, Ile, Nle, Val or Phe
<220> FEATURE:
<221> NAME/KEY: MISC_FEATURE
<222> LOCATION: (5)..(5)
<223> OTHER INFORMATION: Xaa is Gly
<220> FEATURE:
<221> NAME/KEY: MISC_FEATURE
<222> LOCATION: (6)..(6)
<223> OTHER INFORMATION: Xaa is Phe, Lys, Tyr, Trp or Arg
<220> FEATURE:
<221> NAME/KEY: MISC_FEATURE
<222> LOCATION: (7)..(7)
<223> OTHER INFORMATION: Xaa is D-Pro
<220> FEATURE:
<221> NAME/KEY: MISC_FEATURE
<222> LOCATION: (8)..(8)
<223> OTHER INFORMATION: Xaa is Pro, Sar, N-Me-Lys, N-Me-Lys(Ac);
      N-Me-amino acid refers to a group, wherein the alpha-amino group
      carries a methyl group; Lys(Ac) refers to a lysine residue,
      wherein the omega-amino group carries an acetyl group
<220> FEATURE:
<221> NAME/KEY: MISC_FEATURE
<222> LOCATION: (9)..(9)
<223> OTHER INFORMATION: Xaa is Ala, Phe, Tyr or Trp

<400> SEQUENCE: 50

Arg Xaa Asp Xaa Xaa Xaa Xaa Xaa Xaa
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Ser, Gly or Thr
<220> FEATURE:
<221> NAME/KEY: MISC_FEATURE
<222> LOCATION: (4)..(4)
<223> OTHER INFORMATION: Xaa is Leu, Ile, Nle, Val or Phe
<220> FEATURE:
<221> NAME/KEY: MISC_FEATURE
<222> LOCATION: (5)..(5)
<223> OTHER INFORMATION: Xaa is Gly
<220> FEATURE:
<221> NAME/KEY: MISC_FEATURE
<222> LOCATION: (6)..(6)
<223> OTHER INFORMATION: Xaa is Leu, Ile, Nle, Val, Phe, Lys, Tyr, Trp
      or Arg
<220> FEATURE:
<221> NAME/KEY: MISC_FEATURE
<222> LOCATION: (7)..(7)
<223> OTHER INFORMATION: Xaa is D-Pro
<220> FEATURE:
<221> NAME/KEY: MISC_FEATURE
<222> LOCATION: (8)..(8)
<223> OTHER INFORMATION: Xaa is Pro, N-Me-amino acids, N-Me-Lys,
      N-Me-Lys(Ac); N-Me-amino acid refers to a group, wherein the
      alpha-amino group carries a methyl group; Lys(Ac) refers to a
      lysine residue, wherein the omega-amino group carries an acetyl
      group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 51

Arg Xaa Asp Xaa Xaa Xaa Xaa Xaa Xaa
```

```
<210> SEQ ID NO 52
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Ser, Gly or Thr
<220> FEATURE:
<221> NAME/KEY: MISC_FEATURE
<222> LOCATION: (4)..(4)
<223> OTHER INFORMATION: Xaa is Leu, Ile, Nle, Val or Phe
<220> FEATURE:
<221> NAME/KEY: MISC_FEATURE
<222> LOCATION: (5)..(5)
<223> OTHER INFORMATION: Xaa is Gly
<220> FEATURE:
<221> NAME/KEY: MISC_FEATURE
<222> LOCATION: (6)..(6)
<223> OTHER INFORMATION: Xaa is Leu, Ile, Nle, Val, Phe, Lys, Tyr, Trp
      or Arg
<220> FEATURE:
<221> NAME/KEY: MISC_FEATURE
<222> LOCATION: (7)..(7)
<223> OTHER INFORMATION: Xaa is D-Pro
<220> FEATURE:
<221> NAME/KEY: MISC_FEATURE
<222> LOCATION: (8)..(8)
<223> OTHER INFORMATION: Xaa is Pro, Sar, N-Me-Lys, N-Me-Lys(Ac);
      N-Me-amino acid refers to a group, wherein the alpha-amino group
      carries a methyl group; Lys(Ac) refers to a lysine residue,
      wherein the omega-amino group carries an acetyl group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 52

Arg Xaa Asp Xaa Xaa Xaa Xaa Xaa Xaa
1               5

<210> SEQ ID NO 53
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Ser, Gly or Thr
<220> FEATURE:
<221> NAME/KEY: MISC_FEATURE
<222> LOCATION: (4)..(4)
<223> OTHER INFORMATION: Xaa is Leu, Ile, Nle, Val or Phe
<220> FEATURE:
<221> NAME/KEY: MISC_FEATURE
<222> LOCATION: (5)..(5)
<223> OTHER INFORMATION: Xaa is Gly
<220> FEATURE:
<221> NAME/KEY: MISC_FEATURE
<222> LOCATION: (6)..(6)
<223> OTHER INFORMATION: Xaa is Leu, Ile, Nle, Val, Phe, Lys, Tyr, Trp
      or Arg
<220> FEATURE:
<221> NAME/KEY: MISC_FEATURE
<222> LOCATION: (7)..(7)
<223> OTHER INFORMATION: Xaa is D-Pro
<220> FEATURE:
<221> NAME/KEY: MISC_FEATURE
<222> LOCATION: (8)..(8)
<223> OTHER INFORMATION: Xaa is Pro, Sar, N-Me-Lys, N-Me-Lys(Ac);
```

```
        N-Me-amino acid refers to a group, wherein the alpha-amino group
        carries a methyl group; Lys(Ac) refers to a lysine residue,
        wherein the omega-amino group carries an acetyl group
<220> FEATURE:
<221> NAME/KEY: MISC_FEATURE
<222> LOCATION: (9)..(9)
<223> OTHER INFORMATION: Xaa is Ala, Phe, Tyr or Trp

<400> SEQUENCE: 53

Arg Xaa Asp Xaa Xaa Xaa Xaa Xaa Xaa
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Ser, Gly or Thr
<220> FEATURE:
<221> NAME/KEY: MISC_FEATURE
<222> LOCATION: (4)..(4)
<223> OTHER INFORMATION: Xaa is Leu, Ile, Nle, Val or Phe
<220> FEATURE:
<221> NAME/KEY: MISC_FEATURE
<222> LOCATION: (5)..(5)
<223> OTHER INFORMATION: Xaa is Gly or Ala
<220> FEATURE:
<221> NAME/KEY: MISC_FEATURE
<222> LOCATION: (6)..(6)
<223> OTHER INFORMATION: Xaa is Leu, Phe, Lys, Tyr, Trp or Arg
<220> FEATURE:
<221> NAME/KEY: MISC_FEATURE
<222> LOCATION: (7)..(7)
<223> OTHER INFORMATION: Xaa is D-Pro
<220> FEATURE:
<221> NAME/KEY: MISC_FEATURE
<222> LOCATION: (8)..(8)
<223> OTHER INFORMATION: Xaa is Pro, N-Me-amino acids, N-Me-Lys,
        N-Me-Lys(Ac); N-Me-amino acid refers to a group, wherein the
        alpha-amino group carries a methyl group; Lys(Ac) refers to a
        lysine residue, wherein the omega-amino group carries an acetyl
        group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 54

Arg Xaa Asp Xaa Xaa Xaa Xaa Xaa Xaa
1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Ser, Gly or Thr
<220> FEATURE:
<221> NAME/KEY: MISC_FEATURE
<222> LOCATION: (4)..(4)
<223> OTHER INFORMATION: Xaa is Leu, Ile, Nle, Val or Phe
<220> FEATURE:
<221> NAME/KEY: MISC_FEATURE
<222> LOCATION: (5)..(5)
<223> OTHER INFORMATION: Xaa is Gly or Ala
<220> FEATURE:
<221> NAME/KEY: MISC_FEATURE
```

```
<222> LOCATION: (6)..(6)
<223> OTHER INFORMATION: Xaa is Leu, Phe, Lys, Tyr, Trp or Arg
<220> FEATURE:
<221> NAME/KEY: MISC_FEATURE
<222> LOCATION: (7)..(7)
<223> OTHER INFORMATION: Xaa is D-Pro
<220> FEATURE:
<221> NAME/KEY: MISC_FEATURE
<222> LOCATION: (8)..(8)
<223> OTHER INFORMATION: Xaa is Pro, Sar, N-Me-Lys, N-Me-Lys(Ac);
      N-Me-amino acid refers to a group, wherein the alpha-amino group
      carries a methyl group; Lys(Ac) refers to a lysine residue,
      wherein the omega-amino group carries an acetyl group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 55

Arg Xaa Asp Xaa Xaa Xaa Xaa Xaa Xaa
1               5

<210> SEQ ID NO 56
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Ser, Gly or Thr
<220> FEATURE:
<221> NAME/KEY: MISC_FEATURE
<222> LOCATION: (4)..(4)
<223> OTHER INFORMATION: Xaa is Leu, Ile, Nle, Val or Phe
<220> FEATURE:
<221> NAME/KEY: MISC_FEATURE
<222> LOCATION: (5)..(5)
<223> OTHER INFORMATION: Xaa is Gly or Ala
<220> FEATURE:
<221> NAME/KEY: MISC_FEATURE
<222> LOCATION: (6)..(6)
<223> OTHER INFORMATION: Xaa is Leu, Phe, Lys, Tyr, Trp or Arg
<220> FEATURE:
<221> NAME/KEY: MISC_FEATURE
<222> LOCATION: (7)..(7)
<223> OTHER INFORMATION: Xaa is D-Pro
<220> FEATURE:
<221> NAME/KEY: MISC_FEATURE
<222> LOCATION: (8)..(8)
<223> OTHER INFORMATION: Xaa is Pro, Sar, N-Me-Lys, N-Me-Lys(Ac);
      N-Me-amino acid refers to a group, wherein the alpha-amino group
      carries a methyl group; Lys(Ac) refers to a lysine residue,
      wherein the omega-amino group carries an acetyl group
<220> FEATURE:
<221> NAME/KEY: MISC_FEATURE
<222> LOCATION: (9)..(9)
<223> OTHER INFORMATION: Xaa is Ala, Phe, Tyr or Trp

<400> SEQUENCE: 56

Arg Xaa Asp Xaa Xaa Xaa Xaa Xaa Xaa
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Ser, Gly or Thr
<220> FEATURE:
```

```
<221> NAME/KEY: MISC_FEATURE
<222> LOCATION: (4)..(4)
<223> OTHER INFORMATION: Xaa is Leu, Ile, Nle, Val or Phe
<220> FEATURE:
<221> NAME/KEY: MISC_FEATURE
<222> LOCATION: (5)..(5)
<223> OTHER INFORMATION: Xaa is Gly or Ala
<220> FEATURE:
<221> NAME/KEY: MISC_FEATURE
<222> LOCATION: (6)..(6)
<223> OTHER INFORMATION: Xaa is Leu, Phe, Lys, Tyr, Trp or Arg
<220> FEATURE:
<221> NAME/KEY: MISC_FEATURE
<222> LOCATION: (7)..(7)
<223> OTHER INFORMATION: Xaa is D-Pro
<220> FEATURE:
<221> NAME/KEY: MISC_FEATURE
<222> LOCATION: (8)..(8)
<223> OTHER INFORMATION: Xaa is Pro, N-Me-amino acids, N-Me-Lys or
      N-Me-Lys(Ac); N-Me-amino acid refers to a group, wherein the
      alpha-amino group carries a methyl group; Lys(Ac) refers to a
      lysine residue, wherein the omega-amino group carries an acetyl
      group
<220> FEATURE:
<221> NAME/KEY: MISC_FEATURE
<222> LOCATION: (9)..(9)
<223> OTHER INFORMATION: Xaa is Ala, Phe, Tyr or Trp

<400> SEQUENCE: 57

Arg Xaa Asp Xaa Xaa Xaa Xaa Xaa Xaa
1               5

<210> SEQ ID NO 58
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Ser, Gly or Thr
<220> FEATURE:
<221> NAME/KEY: MISC_FEATURE
<222> LOCATION: (4)..(4)
<223> OTHER INFORMATION: Xaa is Leu, Ile, Nle, Val or Phe
<220> FEATURE:
<221> NAME/KEY: MISC_FEATURE
<222> LOCATION: (5)..(5)
<223> OTHER INFORMATION: Xaa is Gly or Ala
<220> FEATURE:
<221> NAME/KEY: MISC_FEATURE
<222> LOCATION: (6)..(6)
<223> OTHER INFORMATION: Xaa is Leu, Ile, Nle, Val, Phe, Lys, Tyr, Trp
      or Arg
<220> FEATURE:
<221> NAME/KEY: MISC_FEATURE
<222> LOCATION: (7)..(7)
<223> OTHER INFORMATION: Xaa is D-Pro
<220> FEATURE:
<221> NAME/KEY: MISC_FEATURE
<222> LOCATION: (8)..(8)
<223> OTHER INFORMATION: Xaa is Pro, Sar, N-Me-Lys, N-Me-Lys(Ac);
      N-Me-amino acid refers to a group, wherein the alpha-amino group
      carries a methyl group; Lys(Ac) refers to a lysine residue,
      wherein the omega-amino group carries an acetyl group
<220> FEATURE:
<221> NAME/KEY: MISC_FEATURE
<222> LOCATION: (9)..(9)
<223> OTHER INFORMATION: Xaa is Ala, Leu, Ile, Nle, Val, Phe, Tyr or Trp

<400> SEQUENCE: 58

Arg Xaa Asp Xaa Xaa Xaa Xaa Xaa Xaa
1               5
```

-continued

```
<210> SEQ ID NO 59
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Ser, Gly or Thr
<220> FEATURE:
<221> NAME/KEY: MISC_FEATURE
<222> LOCATION: (4)..(4)
<223> OTHER INFORMATION: Xaa is Leu, Ile, Nle, Val or Phe
<220> FEATURE:
<221> NAME/KEY: MISC_FEATURE
<222> LOCATION: (5)..(5)
<223> OTHER INFORMATION: Xaa is Gly or Ala
<220> FEATURE:
<221> NAME/KEY: MISC_FEATURE
<222> LOCATION: (6)..(6)
<223> OTHER INFORMATION: Xaa is Leu, Ile, Nle, Val, Phe, Lys, Tyr, Trp
      or Arg
<220> FEATURE:
<221> NAME/KEY: MISC_FEATURE
<222> LOCATION: (7)..(7)
<223> OTHER INFORMATION: Xaa is D-Pro
<220> FEATURE:
<221> NAME/KEY: MISC_FEATURE
<222> LOCATION: (8)..(8)
<223> OTHER INFORMATION: Xaa is Pro, Sar, N-Me-Lys or N-Me-Lys(Ac);
      N-Me-amino acid refers to a group, wherein the alpha-amino group
      carries a methyl group; Lys(Ac) refers to a lysine residue,
      wherein the omega-amino group carries an acetyl group
<220> FEATURE:
<221> NAME/KEY: MISC_FEATURE
<222> LOCATION: (9)..(9)
<223> OTHER INFORMATION: Xaa is Ala, Phe, Tyr or Trp

<400> SEQUENCE: 59

Arg Xaa Asp Xaa Xaa Xaa Xaa Xaa Xaa
1               5

<210> SEQ ID NO 60
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Ser, Gly or Thr
<220> FEATURE:
<221> NAME/KEY: MISC_FEATURE
<222> LOCATION: (4)..(4)
<223> OTHER INFORMATION: Xaa is Leu, Ile, Nle, Val or Phe
<220> FEATURE:
<221> NAME/KEY: MISC_FEATURE
<222> LOCATION: (5)..(5)
<223> OTHER INFORMATION: Xaa is Gly or Ala
<220> FEATURE:
<221> NAME/KEY: MISC_FEATURE
<222> LOCATION: (6)..(6)
<223> OTHER INFORMATION: Xaa is Leu, Ile, Nle, Val, Phe, Lys, Tyr, Trp
      or Arg
<220> FEATURE:
<221> NAME/KEY: MISC_FEATURE
<222> LOCATION: (7)..(7)
<223> OTHER INFORMATION: Xaa is D-Pro
<220> FEATURE:
<221> NAME/KEY: MISC_FEATURE
<222> LOCATION: (8)..(8)
<223> OTHER INFORMATION: Xaa is Pro, N-Me-amino acids, N-Me-Lys or
      N-Me-Lys(Ac); N-Me-amino acid refers to a group, wherein the
      alpha-amino group carries a methyl group; Lys(Ac) refers to a
      lysine residue, wherein the omega-amino group carries an acetyl
```

```
                    group
<220> FEATURE:
<221> NAME/KEY: MISC_FEATURE
<222> LOCATION: (9)..(9)
<223> OTHER INFORMATION: Xaa is Ala, Phe, Tyr or Trp

<400> SEQUENCE: 60

Arg Xaa Asp Xaa Xaa Xaa Xaa Xaa Xaa
1               5

<210> SEQ ID NO 61
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is Ser, Gly or Thr
<220> FEATURE:
<221> NAME/KEY: MISC_FEATURE
<222> LOCATION: (4)..(4)
<223> OTHER INFORMATION: Xaa is Leu, Ile, Nle, Val or Phe
<220> FEATURE:
<221> NAME/KEY: MISC_FEATURE
<222> LOCATION: (5)..(5)
<223> OTHER INFORMATION: Xaa is Gly or Ala
<220> FEATURE:
<221> NAME/KEY: MISC_FEATURE
<222> LOCATION: (6)..(6)
<223> OTHER INFORMATION: Xaa is Leu, Ile, Nle, Val, Phe, Lys, Tyr, Trp
      or Arg
<220> FEATURE:
<221> NAME/KEY: MISC_FEATURE
<222> LOCATION: (7)..(7)
<223> OTHER INFORMATION: Xaa is D-Pro or N-Me-D-lipophilic amino acids;
      N-Me-amino acid refers to a group, wherein the alpha-amino group
      carries a methyl group
<220> FEATURE:
<221> NAME/KEY: MISC_FEATURE
<222> LOCATION: (8)..(8)
<223> OTHER INFORMATION: Xaa is Pro, Sar, N-Me-Lys or N-Me-Lys(Ac);
      N-Me-amino acid refers to a group, wherein the alpha-amino group
      carries a methyl group; Lys(Ac) refers to a lysine residue,
      wherein the omega-amino group carries an acetyl group
<220> FEATURE:
<221> NAME/KEY: MISC_FEATURE
<222> LOCATION: (9)..(9)
<223> OTHER INFORMATION: Xaa is Ala, Phe, Tyr or Trp

<400> SEQUENCE: 61

Arg Xaa Asp Xaa Xaa Xaa Xaa Xaa Xaa
1               5

<210> SEQ ID NO 62
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (4)..(4)
<223> OTHER INFORMATION: Xaa is D-Phe
<220> FEATURE:
<221> NAME/KEY: MISC_FEATURE
<222> LOCATION: (5)..(5)
<223> OTHER INFORMATION: Xaa is N-Me-Val; N-Me-amino acid refers to a
      group, wherein the alpha-amino group carries a methyl group

<400> SEQUENCE: 62

Arg Gly Asp Xaa Xaa
1               5
```

<210> SEQ ID NO 63
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 63

Arg Thr Asp Leu Asp Ser Leu Arg Thr
1               5

<210> SEQ ID NO 64
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (9)..(9)
<223> OTHER INFORMATION: Xaa is D-Pro

<400> SEQUENCE: 64

Ala Arg Gly Asp Leu Ala Ala Leu Xaa Pro
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (9)..(9)
<223> OTHER INFORMATION: Xaa is D-Pro

<400> SEQUENCE: 65

Ala Arg Gly Asp Ala Ala Ala Leu Xaa Pro
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (9)..(9)
<223> OTHER INFORMATION: Xaa is D-Pro

<400> SEQUENCE: 66

Ala Arg Gly Asp Leu Ala Ala Ala Xaa Pro
1               5                   10

<210> SEQ ID NO 67
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (8)..(8)
<223> OTHER INFORMATION: Xaa is D-Pro

<400> SEQUENCE: 67

Ala Arg Gly Asp Leu Ala Leu Xaa Pro
1               5

<210> SEQ ID NO 68
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (7)..(7)
<223> OTHER INFORMATION: Xaa is D-Pro

<400> SEQUENCE: 68

Ala Arg Gly Asp Leu Leu Xaa Pro
1               5

<210> SEQ ID NO 69
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (6)..(6)
<223> OTHER INFORMATION: Xaa is D-Pro

<400> SEQUENCE: 69

Ala Arg Gly Asp Leu Xaa Pro
1               5

<210> SEQ ID NO 70
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (6)..(6)
<223> OTHER INFORMATION: Xaa is D-Asp
<220> FEATURE:
<221> NAME/KEY: MISC_FEATURE
<222> LOCATION: (8)..(8)
<223> OTHER INFORMATION: Xaa is D-Pro

<400> SEQUENCE: 70

Ala Arg Gly Asp Leu Xaa Leu Xaa Pro
1               5

<210> SEQ ID NO 71
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (8)..(8)
<223> OTHER INFORMATION: Xaa is D-Pro

<400> SEQUENCE: 71

Ala Arg Gly Asp Leu Asp Leu Xaa Pro
1               5

<210> SEQ ID NO 72
<211> LENGTH: 9
<212> TYPE: PRT

<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (8)..(8)
<223> OTHER INFORMATION: Xaa is D-Pro

<400> SEQUENCE: 72

Ala Arg Gly Asp Phe Ala Leu Xaa Pro
1               5

<210> SEQ ID NO 73
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (8)..(8)
<223> OTHER INFORMATION: Xaa is D-Pro

<400> SEQUENCE: 73

Ala Arg Gly Asp Leu Ala Phe Xaa Pro
1               5

<210> SEQ ID NO 74
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (8)..(8)
<223> OTHER INFORMATION: Xaa is D-Pro

<400> SEQUENCE: 74

Ala Arg Gly Asp Leu Ala Lys Xaa Pro
1               5

<210> SEQ ID NO 75
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (8)..(8)
<223> OTHER INFORMATION: Xaa is D-Pro

<400> SEQUENCE: 75

Phe Arg Gly Asp Leu Ala Leu Xaa Pro
1               5

<210> SEQ ID NO 76
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (8)..(8)
<223> OTHER INFORMATION: Xaa is D-Pro
<220> FEATURE:
<221> NAME/KEY: MISC_FEATURE
<222> LOCATION: (9)..(9)
<223> OTHER INFORMATION: Xaa is Sar

```
<400> SEQUENCE: 76

Ala Arg Gly Asp Leu Ala Leu Xaa Xaa
1               5

<210> SEQ ID NO 77
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (8)..(8)
<223> OTHER INFORMATION: Xaa is Sar

<400> SEQUENCE: 77

Ala Arg Gly Asp Leu Ala Leu Xaa Pro
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (8)..(8)
<223> OTHER INFORMATION: Xaa is D-Pro
<220> FEATURE:
<221> NAME/KEY: MISC_FEATURE
<222> LOCATION: (9)..(9)
<223> OTHER INFORMATION: Xaa is N-Me-Lys; N-Me-amino acid refers to a
      group, wherein the alpha-amino group carries a methyl group

<400> SEQUENCE: 78

Ala Arg Gly Asp Leu Ala Leu Xaa Xaa
1               5

<210> SEQ ID NO 79
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (8)..(8)
<223> OTHER INFORMATION: Xaa is N-Me-Lys; N-Me-amino acid refers to a
      group, wherein the alpha-amino group carries a methyl group

<400> SEQUENCE: 79

Ala Arg Gly Asp Leu Ala Leu Xaa Pro
1               5

<210> SEQ ID NO 80
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (8)..(8)
<223> OTHER INFORMATION: Xaa is D-Pro
<220> FEATURE:
<221> NAME/KEY: MISC_FEATURE
<222> LOCATION: (9)..(9)
<223> OTHER INFORMATION: Xaa is N-Me-Lys; N-Me-amino acid refers to a
      group, wherein the alpha-amino group carries a methyl group
```

<400> SEQUENCE: 80

Ala Arg Gly Asp Leu Ala Phe Xaa Xaa
1               5

<210> SEQ ID NO 81
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (8)..(8)
<223> OTHER INFORMATION: Xaa is D-Pro
<220> FEATURE:
<221> NAME/KEY: MISC_FEATURE
<222> LOCATION: (9)..(9)
<223> OTHER INFORMATION: Xaa is N-Me-Lys; N-Me-amino acid refers to a
      group, wherein the alpha-amino group carries a methyl group

<400> SEQUENCE: 81

Phe Arg Gly Asp Leu Ala Phe Xaa Xaa
1               5

<210> SEQ ID NO 82
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (8)..(8)
<223> OTHER INFORMATION: Xaa is D-Pro
<220> FEATURE:
<221> NAME/KEY: MISC_FEATURE
<222> LOCATION: (9)..(9)
<223> OTHER INFORMATION: Xaa is N-Me-Lys; N-Me-amino acid refers to a
      group, wherein the alpha-amino group carries a methyl group

<400> SEQUENCE: 82

Phe Arg Gly Asp Leu Ala Tyr Xaa Xaa
1               5

<210> SEQ ID NO 83
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (8)..(8)
<223> OTHER INFORMATION: Xaa is D-Pro
<220> FEATURE:
<221> NAME/KEY: MISC_FEATURE
<222> LOCATION: (9)..(9)
<223> OTHER INFORMATION: Xaa is N-Me-Lys; N-Me-amino acid refers to a
      group, wherein the alpha-amino group carries a methyl group

<400> SEQUENCE: 83

Phe Arg Gly Asp Leu Ala Trp Xaa Xaa
1               5

<210> SEQ ID NO 84
<211> LENGTH: 9
<212> TYPE: PRT
<213> ORGANISM: Artificial Sequence
<220> FEATURE:
<223> OTHER INFORMATION: Synthetic Polypeptide

```
<220> FEATURE:
<221> NAME/KEY: MISC_FEATURE
<222> LOCATION: (8)..(8)
<223> OTHER INFORMATION: Xaa is D-Pro
<220> FEATURE:
<221> NAME/KEY: MISC_FEATURE
<222> LOCATION: (9)..(9)
<223> OTHER INFORMATION: Xaa is N-Me-Lys; N-Me-amino acid refers to a
      group, wherein the alpha-amino group carries a methyl group

<400> SEQUENCE: 84

Tyr Arg Gly Asp Leu Ala Phe Xaa Xaa
1               5

<210> SEQ ID NO 85
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (8)..(8)
<223> OTHER INFORMATION: Xaa is D-Pro
<220> FEATURE:
<221> NAME/KEY: MISC_FEATURE
<222> LOCATION: (9)..(9)
<223> OTHER INFORMATION: Xaa is N-Me-Lys; N-Me-amino acid refers to a
      group, wherein the alpha-amino group carries a methyl group

<400> SEQUENCE: 85

Trp Arg Gly Asp Leu Ala Phe Xaa Xaa
1               5

<210> SEQ ID NO 86
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (8)..(8)
<223> OTHER INFORMATION: Xaa is D-Pro
<220> FEATURE:
<221> NAME/KEY: MISC_FEATURE
<222> LOCATION: (9)..(9)
<223> OTHER INFORMATION: Xaa is N-Me-Lys(Ac); N-Me-amino acid refers to
      a group, wherein the alpha-amino group carries a methyl group;
      Lys(Ac) refers to a lysine residue, wherein the omega-amino group
      carries an acetyl group

<400> SEQUENCE: 86

Phe Arg Gly Asp Leu Ala Phe Xaa Xaa
1               5

<210> SEQ ID NO 87
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (8)..(8)
<223> OTHER INFORMATION: Xaa is D-Pro
<220> FEATURE:
<221> NAME/KEY: MISC_FEATURE
<222> LOCATION: (9)..(9)
```

<223> OTHER INFORMATION: Xaa is N-Me-Lys; N-Me-amino acid refers to a
      group, wherein the alpha-amino group carries a methyl group

<400> SEQUENCE: 87

Phe Arg Gly Asp Leu Ala Arg Xaa Xaa
1               5